(12) United States Patent
Kassab et al.

(10) Patent No.: US 8,979,876 B2
(45) Date of Patent: Mar. 17, 2015

(54) DEVICES AND METHODS FOR TISSUE RESTORATION

(75) Inventors: Ghassan S. Kassab, Zionsville, IN (US); Jose A. Navia, Sr., Buenos Aires (AR)

(73) Assignee: CVDevices, LLC, San Diego, CA (US)

( * ) Notice: Subject to any disclaimer, the term of this patent is extended or adjusted under 35 U.S.C. 154(b) by 710 days.

(21) Appl. No.: 13/080,586

(22) Filed: Apr. 5, 2011

(65) Prior Publication Data

US 2011/0245593 A1      Oct. 6, 2011

Related U.S. Application Data

(63) Continuation-in-part of application No. 12/861,251, filed on Aug. 23, 2010, which is a continuation-in-part of application No. 12/546,139, filed on Aug. 24, 2009.

(51) Int. Cl.
*A61B 17/08*      (2006.01)
*A61F 5/00*      (2006.01)
*A61B 17/122*      (2006.01)

(52) U.S. Cl.
CPC ............. *A61F 5/0013* (2013.01); *A61F 5/0086* (2013.01); *A61B 17/122* (2013.01); *A61B 17/1227* (2013.01)
USPC .......................................... 606/157; 606/151

(58) Field of Classification Search
USPC .......... 606/151, 153, 157–158; 24/63.7, 67.5, 24/558, 565, 567
See application file for complete search history.

(56) References Cited

U.S. PATENT DOCUMENTS

| | | | |
|---|---|---|---|
| 2005/0119674 A1* | 6/2005 | Gingras | 606/151 |
| 2007/0213585 A1* | 9/2007 | Monassevitch et al. | 600/104 |
| 2008/0132915 A1* | 6/2008 | Buckman et al. | 606/138 |
| 2008/0177292 A1* | 7/2008 | Jacobs et al. | 606/157 |
| 2010/0174295 A1* | 7/2010 | Kassab et al. | 606/142 |

OTHER PUBLICATIONS

PCT/US2010/046479, PCT International Preliminary Report on Patentability, dated Mar. 8, 2012.

* cited by examiner

*Primary Examiner* — Diane Dornbusch
(74) *Attorney, Agent, or Firm* — Reichel IP LLP; Mark C. Reichel; Natalie J. Dean

(57) ABSTRACT

Devices and methods for tissue restoration. In an exemplary embodiment of an implantable restraining device of the present disclosure, the device comprises a first engaging component and a second engaging component at least substantially parallel to one another, a first swivel arm, comprising a first fixed arm, a first expandable arm, and a first hub, and a second swivel arm, comprising a second fixed arm, a second expandable arm, and a second hub.

20 Claims, 47 Drawing Sheets

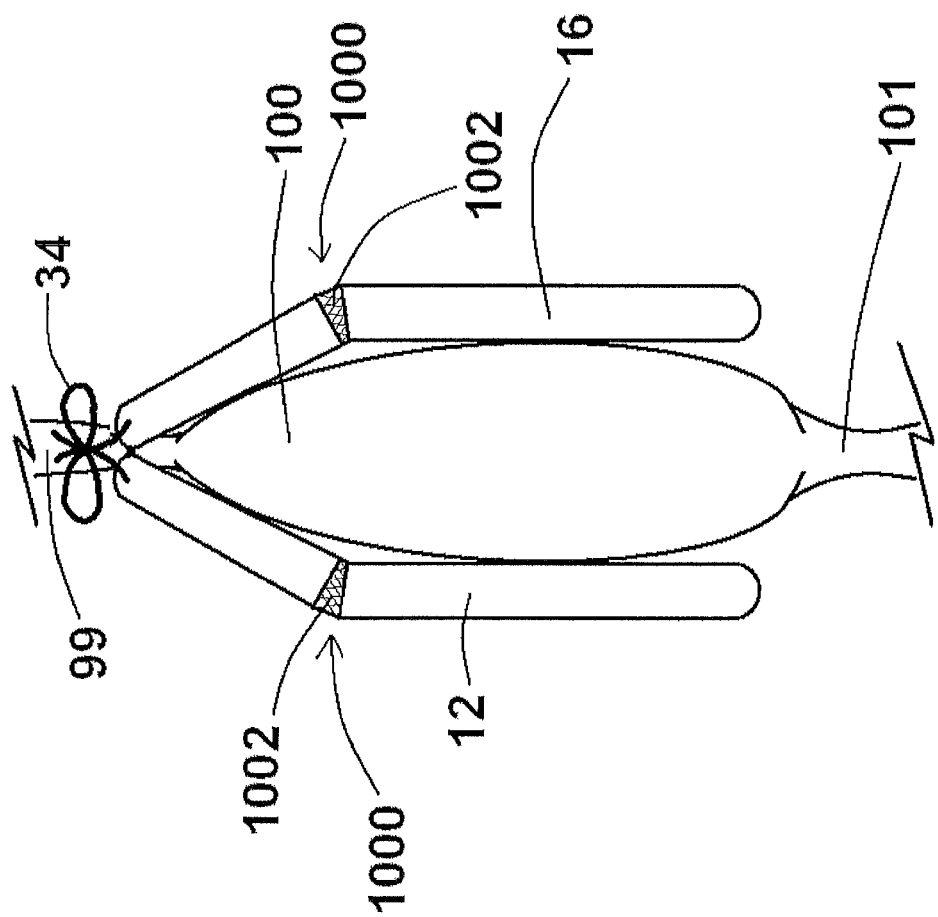

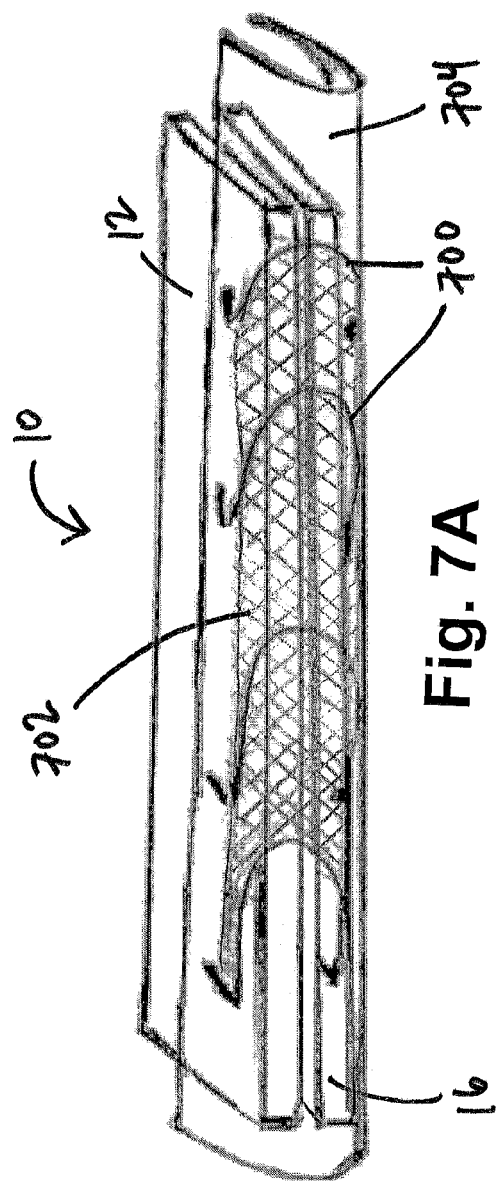
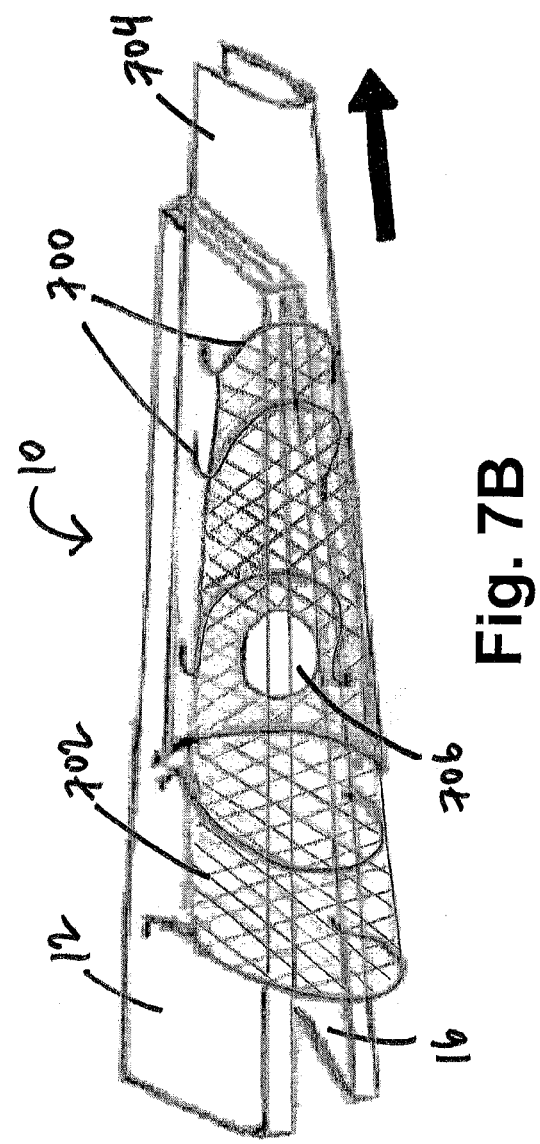
Fig. 7A
Fig. 7B

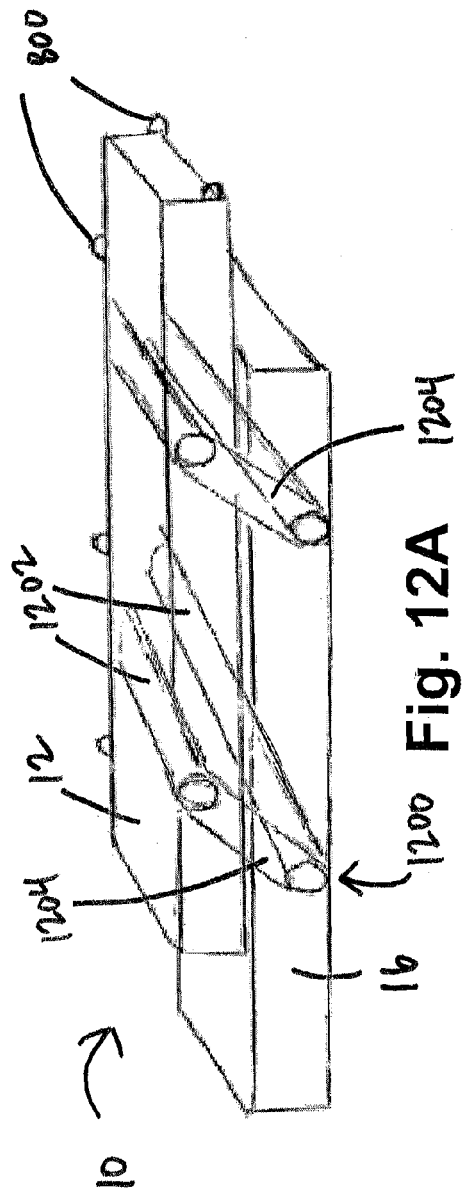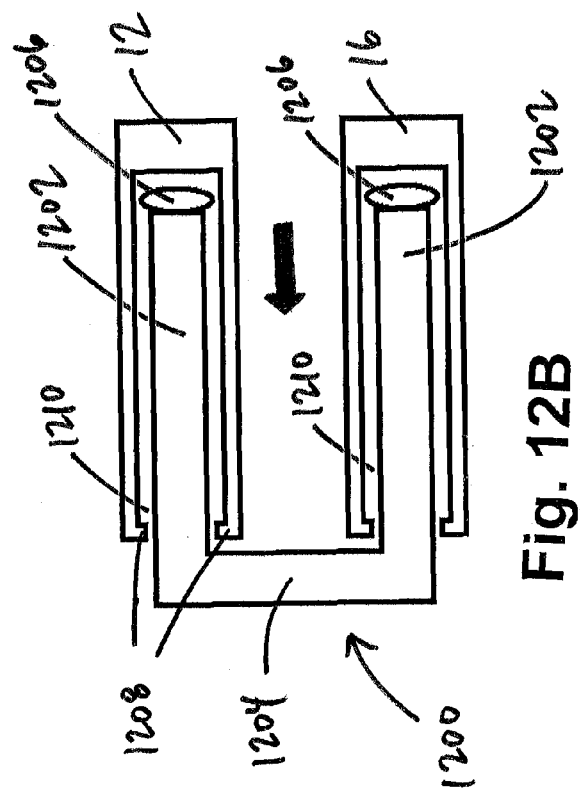
Fig. 12A
Fig. 12B

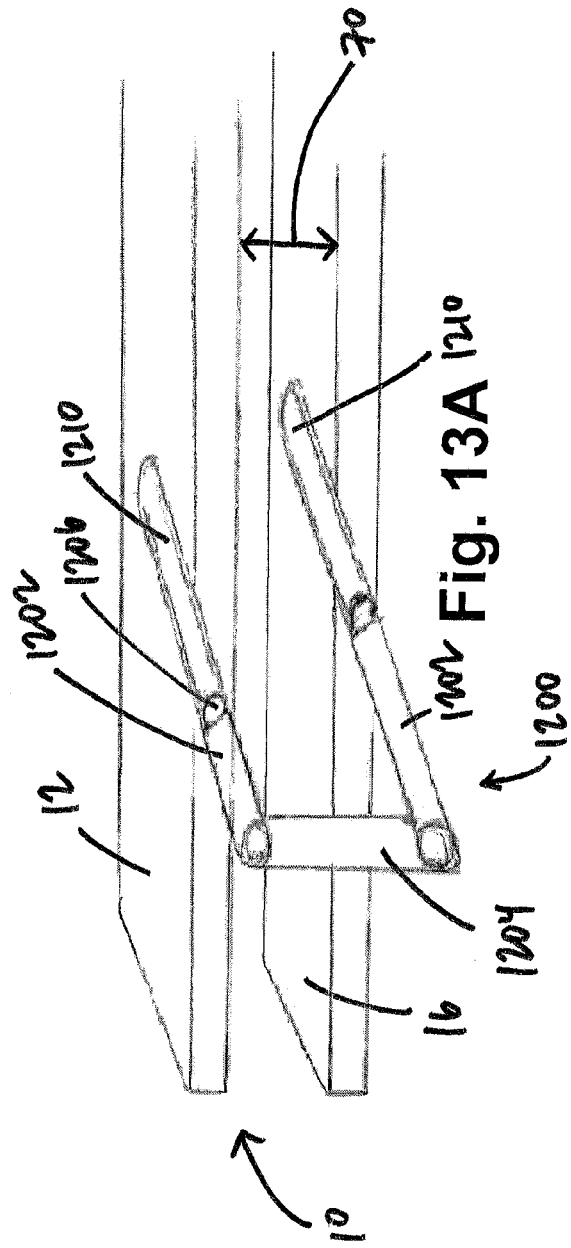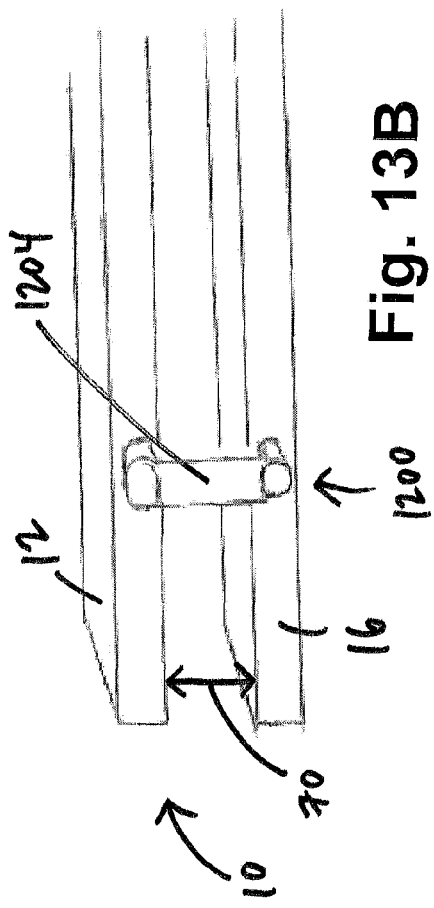

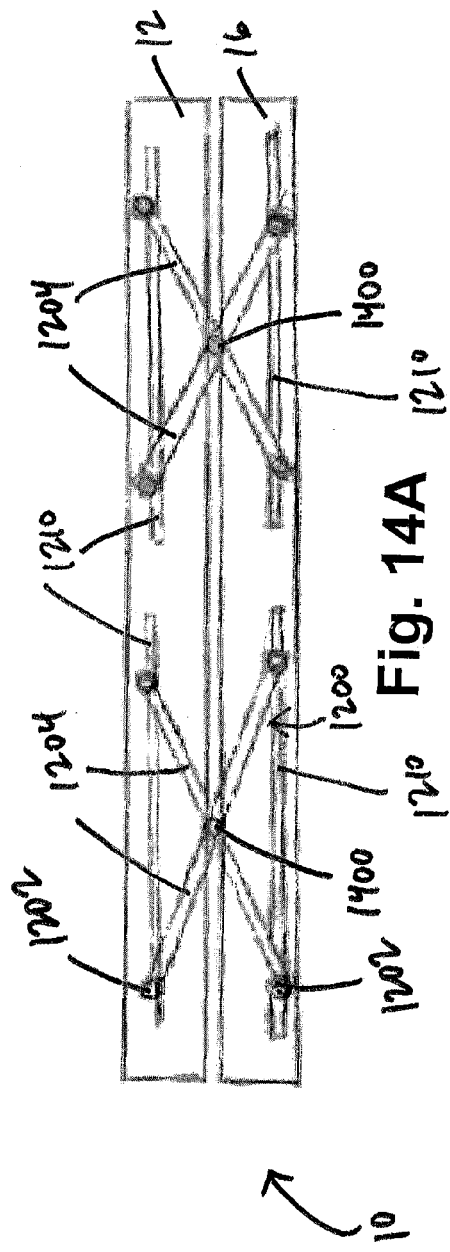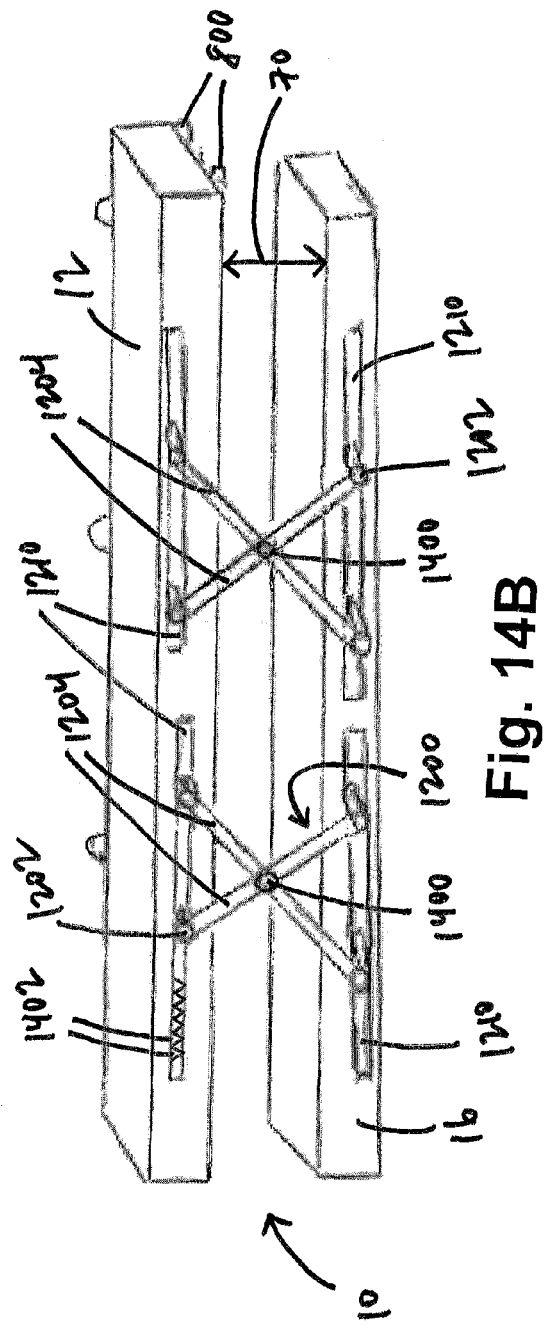
Fig. 14A
Fig. 14B

DEVICES AND METHODS FOR TISSUE RESTORATION

PRIORITY

The present U.S. continuation-in-part patent application is related to, and claims the priority benefit of, U.S. patent application Ser. No. 12/861,251 filed Aug. 23, 2010, which is related to, claims the priority benefit of, and is a U.S. continuation-in-part application of, U.S. patent application Ser. No. 12/546,139, filed Aug. 24, 2009. The contents of each of these applications are hereby incorporated by reference in their entirety into this disclosure.

BACKGROUND

Organ and tissue surgical restoration are clinical techniques that may be applied to numerous different body tissues, ranging from blood vessels to whole organs. Conventionally, such surgical techniques require the use of incisions, pins, staples and/or significant sutures in order to alter the tissue's anatomy. For example, surgical gastric restoration often employed to treat obesity and typically involves the reorganization of the digestive tract. Conventional examples of such procedures involve attempts to either 1) restrict food intake into the body via a restrictive bariatric procedure (a "Restrictive Procedure"), or 2) alter the anatomy of the small intestine or divert the peristalsis of a person's normal food intake past the small intestine to decrease caloric absorption via a malabsorptive bariatric procedure, which is commonly known as a gastric bypass (a "Malabsorptive Procedure"). It is also known to combine the two procedures such that both of the aforementioned techniques are employed jointly.

Malabsorptive Procedures entail an intestinal bypass that results in the exclusion of almost all of the small intestine from the digestive tract. In most Malabsorbptive Procedures, a portion of the stomach or small intestine is removed from the digestive tract through a surgical procedure that requires cutting the digestive tissue and thereafter closing any holes or securing the newly formed anatomy with staples and/or sutures. Conversely, Restrictive Procedures generally involve the creation of a passageway extending from the upper portion of the stomach to the lower portion of the stomach in order to decrease the size of the organ and thus prevent the stomach from storing large amounts of food. Conventional Restrictive Procedures rely on the banding, suturing and/or stapling of the stomach to create a small pouch on the superior portion of the stomach near the gastroesophageal junction.

Combined operations consisting of Malabsorptive and Restrictive Procedures are the most common bariatric procedures performed today. An example of a combined procedure is the Extended (Distal) Roux-en-Y Gastric Bypass in which a stapling creates a small stomach pouch (approximately 15 to 20 cc) completely separated from the remainder of the stomach. In addition, the small intestine is divided just beyond the duodenum (the hollow tube connecting the stomach to the jejunum), re-arranged into a Y-configuration, and sutured to the small upper stomach pouch to enable the outflow of food therefrom through the newly formed "Roux limb."

Accordingly, most digestive tract restoration procedures require that the stomach and/or tissue of the intestine is cut and thereafter sutured or stapled back together. As the digestive tract contains numerous enzymes, strong acids and multiple species of bacteria that assist with digestion, the perforation of an organ and/or tissue thereof is particularly problematic due to the likelihood of leakage therefrom and/or increased risk of serious infection. As such, conventional gastric surgical restoration procedures have high rates of post-operative complications that may require prolonged hospitalization and even additional operations, and are often irreversible and/or permanently affect the restored tissue and/or organ. Accordingly, a need exists for safe and effective devices and methods for restoring organs and tissue that are reversible and do not require cutting or penetrating the underlying tissue with significant sutures, staples and/or pins.

It will be appreciated that the foregoing examples are only provided as examples and that there are numerous other indications where intervention is necessary either to restore the underlying organ or tissue and/or to provide support thereto.

BRIEF SUMMARY

In at least one exemplary embodiment of an implantable restraining device of the present disclosure, the device comprises a first engaging component and a second engaging component at least substantially parallel to one another, a first swivel arm, comprising a first fixed arm, a first expandable arm, and a first hub, wherein the first fixed arm is pivotally connected to the first engaging component at or near a first fixed arm first end and is coupled to the first hub at or near a first fixed arm second end, and wherein the first expandable arm is pivotally connected to the second engaging component at or near a first expandable arm first end and is connected to the first hub at or near a first expandable arm second end by way of a first hub bracket, a second swivel arm, comprising a second fixed arm, a second expandable arm, and a second hub, wherein the second fixed arm is pivotally connected to the first engaging component at or near a second fixed arm first end and is coupled to the second hub at or near a second fixed arm second end, and wherein the second expandable arm is pivotally connected to the second engaging component at or near a second expandable arm first end and is connected to the second hub at or near a second expandable arm second end by way of a second hub bracket, and wherein the first expandable arm and the second expandable are capable of movement relative to the first hub and the second hub respectively so that a distance between the first engaging component and the second engaging component may change relative to movement of the first expandable arm and the second expandable arm. In another embodiment, the first swivel arm is capable of rotation in a first direction, and wherein the second swivel arm is capable of rotation in an opposing second direction. In yet another embodiment, the first swivel arm and the second swivel arm are capable of rotation so that the first swivel arm, the second swivel arm, the first engaging component, and the second engaging component share a common linear axis. In an additional embodiment, the first swivel arm and the second swivel arm are capable of rotation so that the first swivel arm and the second swivel arm are substantially or fully perpendicular to the first engaging component and the second engaging component. In yet an additional embodiment, the first fixed arm is relatively shorter than the second fixed arm, and wherein the first expandable arm is relatively shorter than the second expandable arm.

In at least one exemplary embodiment of an implantable restraining device of the present disclosure, the device further comprises a first arm flange at or near the first expandable arm second end, the first arm flange configured to limit expansion of the first expandable arm relative to the first fixed arm, and a second arm flange at or near the second expandable arm second end, the second arm flange configured to limit expansion of the second expandable arm relative to the second fixed arm. In an additional embodiment, the device is sized and shaped to fit within a laparoscopic bodily port.

In at least one exemplary embodiment of an implantable restraining device of the present disclosure, the device further comprises a first strap positioned at a first end of the first engaging component and at a first end of the second engaging component, the first strap configured to limit movement of the first engaging component and the second engaging component when the first strap is coupled to the first engaging component and the second engaging component. In an additional embodiment, the first strap is fixedly coupled to one of the first end of the first engaging component or the first end of the second engaging component. In yet an additional embodiment, the first strap is coupled to one of the first end of the first engaging component or the first end of the second engaging component by way of at least one suture. In another embodiment, the first strap has at least one suture aperture defined therethrough, and wherein at least one of the first engaging component and the second engaging component has at least one plate aperture defined therethrough, the at least one suture aperture and the at least one plate aperture configured to permit a suture to be placed therethrough to couple the first strap to either the first engaging component or the second engaging component.

In at least one exemplary embodiment of an implantable restraining device of the present disclosure, the device further comprises a first pad coupled to one or both of the first fixed arm and the first expandable arm, and a second pad coupled to one or both of the second fixed arm and the second expandable arm, wherein the first pad and the second pad are configured to engage at least a portion of a mammalian bodily organ positioned therebetween. In another embodiment, the first engaging component and the second engaging component are configured to engage a targeted tissue therebetween when the first swivel arm and the second swivel arm are in a configuration relatively perpendicular to the first engaging component and the second engaging component. In yet another embodiment, the first engaging component, the second engaging component, the first swivel arm, and the second swivel arm each comprise a material suitable to resist corrosion selected from the group consisting of polyurethane, polyethylene, polytetrafluoroethylene, polyaryletherketone, carbothane, tecothane, nitinol, silastic, titanium, and stainless steel.

In at least one exemplary embodiment of an implantable restraining device of the present disclosure, each of the first engaging component and the second engaging component define one or more facets along at least part of a length of said engaging components, said facets providing a generally arcuate profile of said engaging components. In an additional embodiment, each of the first engaging component and the second engaging component comprise a configuration chosen from a straight bar configuration, a curved configuration, or a circular configuration. In yet an additional embodiment, the first engaging component and the second engaging component are flexible or semi-flexible.

In at least one exemplary embodiment of an implantable restraining device of the present disclosure, the device comprises a first engaging component and a second engaging component at least substantially parallel to one another, a first swivel arm, comprising a first fixed arm, a first expandable arm, and a first hub, wherein the first fixed arm is pivotally connected to the first engaging component at or near a first fixed arm first end and is coupled to the first hub at or near a first fixed arm second end, and wherein the first expandable arm is pivotally connected to the second engaging component at or near a first expandable arm first end and is connected to the first hub at or near a first expandable arm second end by way of a first hub bracket, a second swivel arm, comprising a second fixed arm, a second expandable arm, and a second hub, wherein the second fixed arm is pivotally connected to the first engaging component at or near a second fixed arm first end and is coupled to the second hub at or near a second fixed arm second end, and wherein the second expandable arm is pivotally connected to the second engaging component at or near a second expandable arm first end and is connected to the second hub at or near a second expandable arm second end by way of a second hub bracket, and a first strap positioned at one or both of a first end of the first engaging component and at a first end of the second engaging component, the first strap configured to limit movement of the first engaging component and the second engaging component when the first strap is coupled to the first engaging component and the second engaging component. wherein the first expandable arm and the second expandable are capable of movement relative to the first hub and the second hub respectively so that a distance between the first engaging component and the second engaging component may change relative to movement of the first expandable arm and the second expandable arm, and wherein the first swivel arm is capable of rotation in a first direction so that the first swivel arm, the second swivel arm, the first engaging component, and the second engaging component share a common linear axis, and wherein the second swivel arm is capable of rotation in an opposing second direction so that the first swivel arm and the second swivel arm are substantially or fully perpendicular to the first engaging component and the second engaging component.

In at least one embodiment of a method for restoring a targeted tissue of the present disclosure, the method comprises the steps of inserting an implantable restraining device into a body cavity of a mammalian body, the implantable restraining device comprising a first engaging component and a second engaging component at least substantially parallel to one another, a first swivel arm, comprising a first fixed arm, a first expandable arm, and a first hub, wherein the first fixed arm is pivotally connected to the first engaging component at or near a first fixed arm first end and is coupled to the first hub at or near a first fixed arm second end, and wherein the first expandable arm is pivotally connected to the second engaging component at or near a first expandable arm first end and is connected to the first hub at or near a first expandable arm second end by way of a first hub bracket, a second swivel arm, comprising a second fixed arm, a second expandable arm, and a second hub, wherein the second fixed arm is pivotally connected to the first engaging component at or near a second fixed arm first end and is coupled to the second hub at or near a second fixed arm second end, and wherein the second expandable arm is pivotally connected to the second engaging component at or near a second expandable arm first end and is connected to the second hub at or near a second expandable arm second end by way of a second hub bracket, advancing the implantable restraining device to a location within the mammalian body adjacent to a targeted tissue, swiveling the first swivel arm and the second swivel arm so that the first swivel arm and the second swivel arm are substantially perpendicular to the first engaging component and the second engaging component, and positioning the first engaging component and the second engaging component over the targeted tissue such that at least a portion of the targeted tissue is positioned therebetween, wherein when the targeted tissue expands in a direction between the first engaging component and the second engaging component, the targeted tissue exerts a force upon the first engaging component and the second engaging component so that the first expandable arm moves relative to the first hub and so that the second expandable arm moves relative to the second hub. In another embodiment, the targeted tissue is a stomach, and wherein expansion of the stomach, with said device positioned thereon, functionally divides the stomach into a first stomach portion and a second stomach portion.

BRIEF DESCRIPTION OF THE DRAWINGS

FIGS. 5A through 5D show various embodiments of restraining devices positioned about a stomach according to the present disclosure;

FIGS. 7A, 7B, and 8 show various embodiments of a restraining device comprising one or more struts according to the present disclosure;

FIGS. 12A, 12B, 13A, and 13B show various embodiments of a restraining device comprising a coupler according to the present disclosure;

FIGS. 14A and 14B show exemplary embodiments of a restraining device comprising a coupler and a coupler pivot according to the present disclosure;

DETAILED DESCRIPTION

Figure 1:
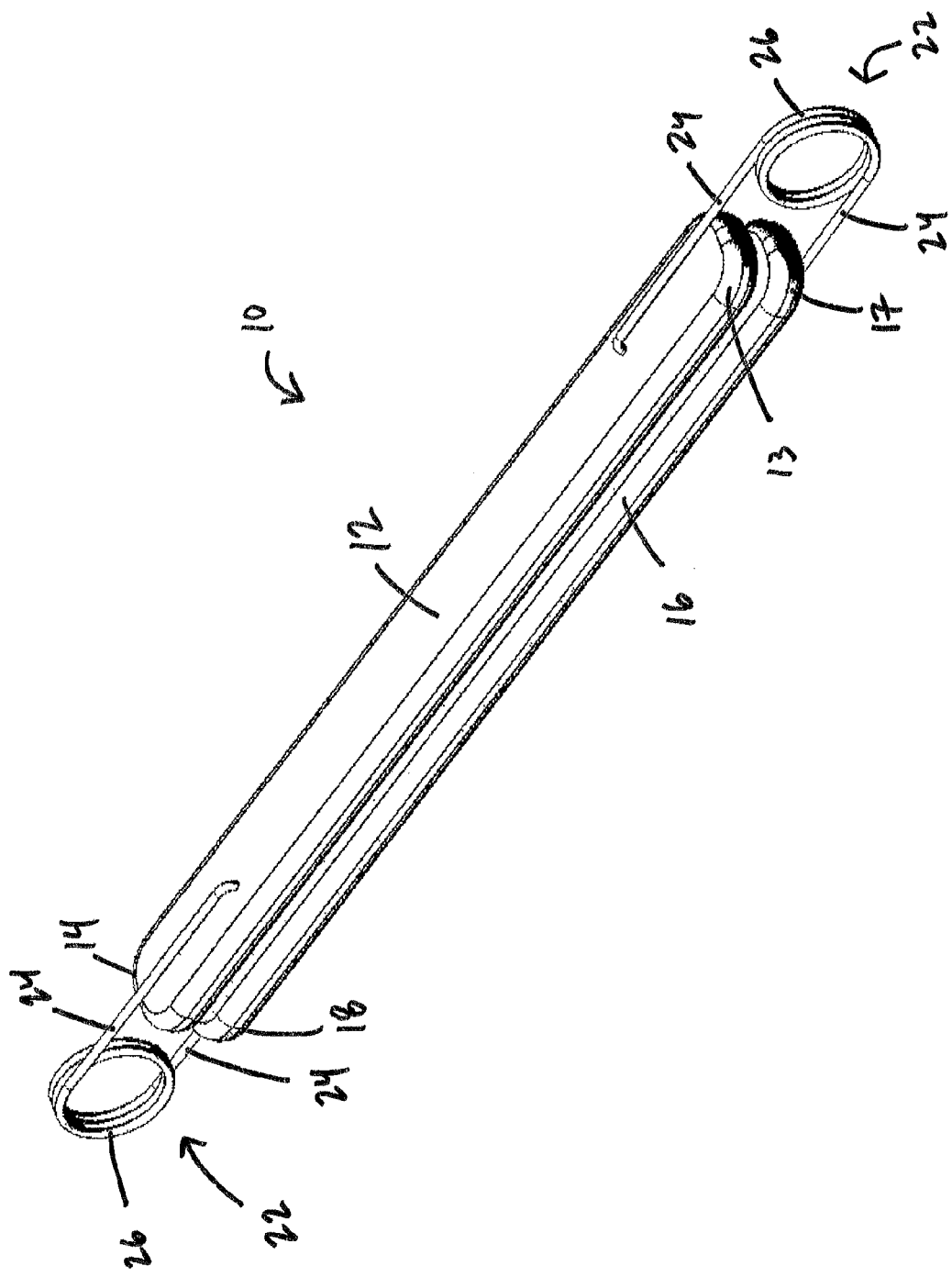
FIGS. 1 and 2 show perspective views of at least one embodiment of a restraining device for restoring and/or supporting a tissue or organ of the present disclosure.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

Figure 2:
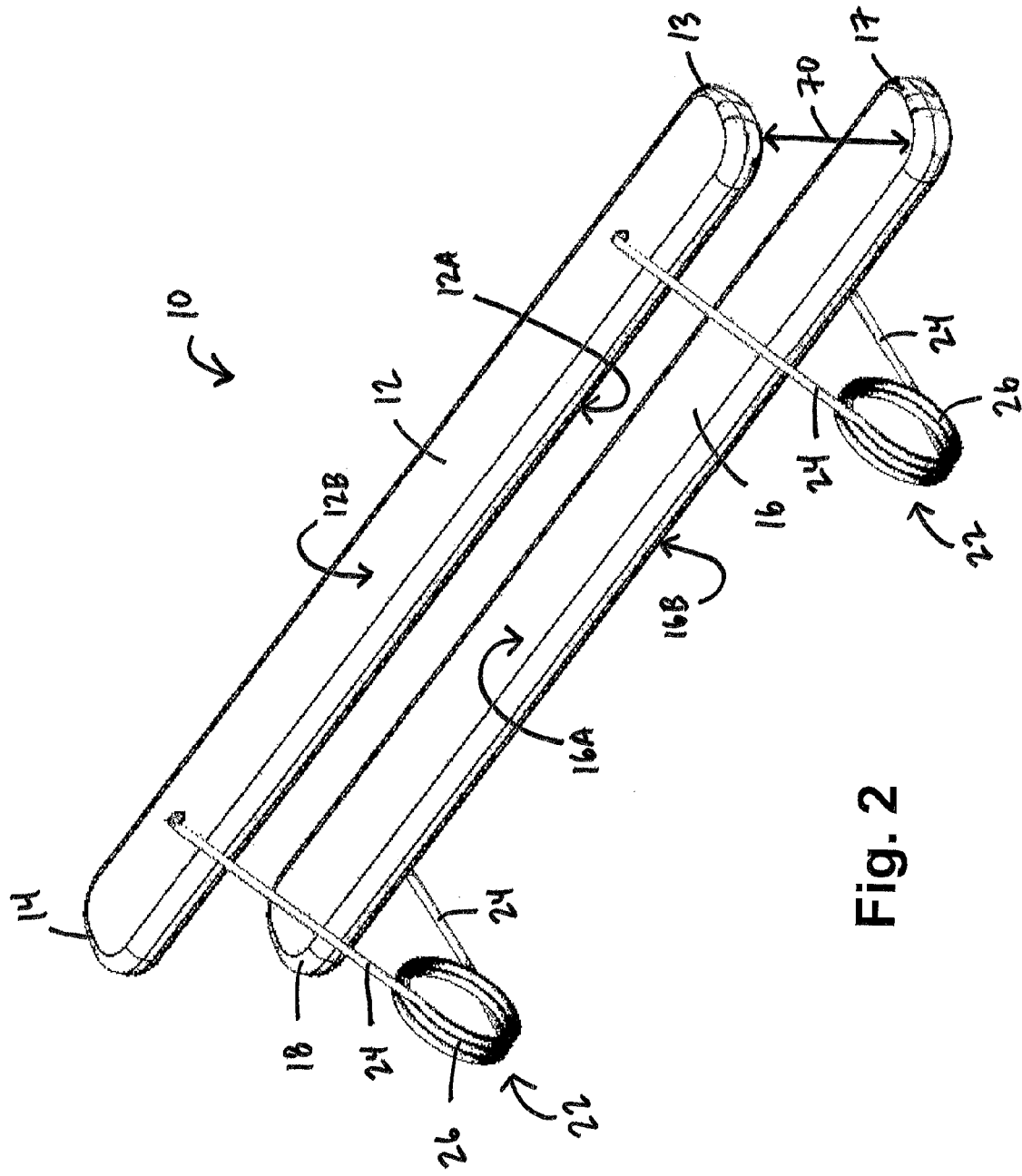

FIGS. 1 and 2 show perspective views of at least one embodiment of a restraining device 10 for restoring a tissue or organ. In at least one embodiment of the restraining device 10, the restraining device 10 comprises an implantable device and does not require substantial sutures, staples or pins to be secured on the targeted tissue or organ of interest. Further, the restraining device 10 described herein is configured to loosely, albeit securely, engage to the targeted tissue such that the underlying tissue is either uncompressed or only loosely compressed. The various embodiments of the restraining device 10 described herein may be available for temporary or chronic placement within a patient's body, and the restoration procedures performed through the use of an exemplary device 10 are reversible through minimally invasive procedures.

As shown in FIGS. 1 and 2, at least one embodiment of the restraining device 10 comprises a first engaging component 12 and a second engaging component 16. The first engaging component 12 may comprise a first shape and the second engaging component 16 may comprise a second shape that corresponds to at least a portion of the first shape of the first engaging component 12. For example, and without limitation, the first and second engaging components 12, 16 may be configured in a bar configuration as shown in FIGS. 1 and 2. Alternatively, the first and second engaging components 12, 16 may be configured in a contoured, circular or any other configuration suitable for use as referenced herein. Additionally, the first and second engaging components 12, 16 may be configured such that the shape of each of the components 12, 16 defines an interior area (not shown). It will be understood that the first and second engaging components 12, 16 of an exemplary restraining device 10 may be configured in any shape and may also be flexible, semi-flexible, or articulated. Furthermore, it is contemplated that a clinician may select the desired configuration of the components 12, 16 of the restraining device 10 based on the particular patient to be treated and/or pursuant to the specific application for which the restraining device 10 will be used to ensure that the restraining device 10 appropriately conforms to the tissue or organ of interest. For example, an exemplary embodiment of a restraining device 10 of the present disclosure may comprise first and second engaging components 12, 16 having a width of approximately 14 mm and a length of approximately 120 mm. In at least one additional embodiment, the first and second engaging components 12, 16 may have a width between 5 mm and 15 mm, and may have a length between 30 mm and 200 mm, with any number of potential widths and lengths contemplated by the present disclosure suitable for use with an exemplary restraining device 10 of the present disclosure.

In at least one embodiment of a restraining device 10 of the present disclosure, and as shown in FIG. 2, the first engaging component 12 of the restraining device 10 comprises a proximal end 13, a body having a first side 12A and a second side 12B, and a distal end 14. The first side 12A of the first engaging component 12 is configured to be positioned adjacent to or in contact with a tissue or organ of interest. Likewise, the second engaging component 16 comprises a proximal end 17, a body having a first side 16A and a second side 16B, and a distal end 18. The first side 16A of the second engaging component 16 is configured to be positioned adjacent to or in contact with the tissue or organ of interest.

The first engaging component 12 and the second engaging component 16 each comprise a material suitable to resist corrosion, such as and without limitation polyurethane, polyethylene, polytetrafluoroethylene ("PTFE"), nitinol, silastic, titanium, stainless steel or any other material suitable for use in the medical arts that is corrosion resistant. Accordingly, the restraining device 10 can withstand chronic placement within a body without the risk of deterioration. In at least one embodiment, the first and second engaging components 12, 16 of the restraining device 10 are comprised of ultra high density polyethylene.

The first and second engaging components 12, 16 of the restraining device 10 may be coupled to one or more springs 22, wherein the one or more springs 22 engage the first and second engaging components 12, 16 at their distal ends 14, 18 and proximal ends 13, 17. Springs 22, as well as struts 700 (as shown in FIGS. 7A and 7B) and couplers 1200 (as shown in FIGS. 14A through 16B), as referenced herein, may be generally referred to as "connector(s)" as they connect, in various embodiments, first engaging components 12 and second engaging components 16 of various restraining devices 10 of the present disclosure. The springs 22 may comprise torsion springs or any other type of spring known or developed that is capable of supporting the first and second engaging components 12, 16 a prescribed distance apart from each other, which may vary depending upon the orientation of the springs 22 about the first and second engaging components 12, 16. As described in more detail herein, due to the configuration and resistance of the springs 22, the first and second engaging components 12, 16 of the restraining device may be held such that little or no space is defined between the first sides 12A, 16A of the first and second engaging components 12, 16 based upon a first orientation of springs 22, and the first and second engaging components 12, 16 of the restraining device 10 may be held such that an interior space 70 is defined between the first sides 12A, 16A of the first and second engaging components 12, 16 based upon a second orientation of springs 22.

Further, each of the one or more springs 22 may have any number of coils configured in any fashion, provided the spring configuration and stiffness are suitable for the desired application of the restraining device 10. For example, and without limitation, in at least one embodiment each of the one or more springs 22 comprises a torsion, resistance spring having three (3) closely-coiled coils. It will be appreciated that, in practice, a clinician may alter the number of coils and/or configuration of each spring 22 to achieve to a desired flexibility or rigidity of the springs 22 and, in this manner, the restraining device 10 may be customized for a particular patient and/or application for which the restraining device 10 is to be applied.

Each of the springs 22 of the restraining device 10 may comprise at least one rod 24 extending from each of the ends of its coils. The length of each rod 24 may be selected depending on the particular application for which the restraining device 10 is to be applied. As shown in the exemplary embodiments of a restraining device 10 in FIGS. 1 and 2, each rod 24 is coupled with either the first or second engaging component 12, 16. For example, as shown in FIG. 2, the first rod 24 of one of the springs 22 may be coupled with the second side 12B of the first engaging component 12 at or near a location on the distal end 14 of the first engaging component 12, and the second rod 24 of the same spring 22 may be coupled with the second side 16B of the second engaging component 16 at or near a location on the distal end 18 of the second engaging component 16. Furthermore, the rods 24 facilitate the formation of the interior space 70 (as shown in FIG. 2) between the first and second engaging components 12, 16 by holding the first and second engaging components 12, 16 in accordance with the tension of the springs 22.

The springs 22 of the restraining device 10 may comprise any dimensions so long as the restraining device 10 is of a sufficient size to move through a laparoscopic port and the springs 22 are capable of holding the first side 12A of the first engaging component 12 and the second side 16A of the second engaging component 16 a distance apart when the restraining device 10 has a configuration whereby the springs 22 are positioned about the first and second engaging components 12, 16. For example, springs 22 may have a "first" configuration as shown in FIG. 1, whereby springs 22 and the first and second engaging components 12, 16 are oriented in the same or substantially the same direction/plane so that the restraining device 10 may pass through a laparoscopic port. In such a first configuration, springs 22 engage the first and second engaging components 12, 16 so that the first and second engaging components 12, 16 either engage one another or have a relatively small space between them. Springs 22 may have a "second" configuration, for example and as shown in FIG. 2, when springs 22 are rotated about first and second engaging components 12, 16 and are not in the same direction/plane as the configuration of restraining device shown in FIG. 1. In such a second configuration, the first and second engaging components 12, 16 may define an interior space 70 when the restraining device 10 is "at rest," with the interior space 70 increasing upon positioning the restraining device 10 around a stomach 100 (as shown in FIGS. 4A through 5A) for example, and potentially increasing only slightly further upon introduction of food, for example, into the stomach 100.

Accordingly, the dimensions of the springs 22 may dictate the native value of the interior space 70 between the first and second engaging components 12, 16. In at least one embodiment, the springs 22 may comprise a maximum outside diameter that is less than about 14 millimeters to allow a "collapsed" or "compressed" restraining device 10 to pass within a 15 mm diameter abdominal port. Furthermore, each of the springs 22 may comprise any material having a strength that is consonant with the application for which the restraining device 10 will be employed. In at least one embodiment, the springs 22 are comprised of a rigid or semi-rigid material that is suitable to resist corrosion, such as and without limitation, polyurethane, PTFE, nitinol, silastic, titanium, stainless steel or any other material suitable for use in the medical arts that is corrosion resistant.

Referring back to FIG. 2, and as previously described, the springs 22 of the restraining device 10 are biased to maintain the first and second engaging components 12, 16 at a prescribed distance apart under a native, and as described above, "second" configuration. In this manner, when no pressure is applied to an exemplary restraining device 10—or when the restraining device 10 is "at rest"—the interior space 70 having a prescribed value is formed between the first and second engaging components 12, 16. The value of the interior space 70 may, in at least one embodiment, correlate with the outside diameter of the springs 22, minus the thickness of the first and second engaging components 12, 16. It will be understood that the value of the interior space 70 can be manipulated by a clinician depending on the thickness of tissue and/or organ to be treated or other factors. For example, to achieve an interior space 70 having a larger prescribed value, the outer diameter of the spring 22 may be increased and/or the thickness of the first and/or second engaging components 12, 16 may be adjusted. Accordingly, a clinician can easily modify the restraining device 10 such that it may be optimally configured for a particular application on a particular tissue.

Due to the nature of the springs 22 (depending on the material and rigidity selected), the first and second engaging components 12, 16 may exhibit some degree of "give" such that the first and second engaging components 12, 16 are capable of moving relative to each other when pressure is applied. While the first and second engaging components 12, 16 are biased to return to their resting position such that the interior space 70 is substantially equivalent to its prescribed/native value when no pressure is applied to the springs 22, the springs 22 of the restraining device 10 are also capable of allowing the first and second engaging components 12, 16 to move in response to force applied thereto. For example, and without limitation, if a force is applied against the first sides 12A, 16A of the first and second engaging components 12, 16, this force is translated to the springs 22 which enables the components 12, 16 of the restraining device 10 to move apart such that the interior space 70 is increased. Furthermore, if a force is applied directly to the springs 22 such that the coils are twisted about their axis in a direction counter to the coil configuration, similar to the above-listed example, the resultant effect on the restraining device 10 is that the first and second engaging components 12, 16 are moved apart and the interior space 70 is increased. However, due to the inherent bias provided by the springs 22 of the restraining device 10, after the pressure affecting the springs 22 is released, the springs 22—and thus the components 12, 16—return to their resting positions such that the interior space 70 reverts to its original prescribed value. It will be appreciated that the specific configuration and/or materials comprising each of the springs 22 may be selected to achieve the desired degree of elasticity depending on the application for which the restraining device 10 is to be applied.

As shown in FIG. 2, each rod 24 of spring 22 is rotatably coupled with the relevant component 12, 16 of the restraining device 10 such that each of the rods 24 is capable of pivotal movement with respect to the relevant component 12, 16 of the restraining device 10. The rotational coupling of the rods 24 with the first and second engaging components 12, 16 may be achieved through any means known in the art. For example and without limitation, the end of each rod 24 may comprise a pin that is capable of insertion into and rotation within a hole formed within the respective second side 12B, 16B of the applicable component 12, 16.

As each of the rods 24 is coupled with a spring 22, when the rods 24 rotate with respect to the components 12, 16, this effectively enables the respective spring 22 to move in an orbital manner with respect to the proximal or distal end of the restraining device 10. Accordingly, the springs 22 are capable of rotating between a position that is substantially parallel with the first and second engaging components 12, 16 (as shown in FIG. 1, referred to as a "first" configuration herein) and a position that is substantially perpendicular to the first and second engaging components 12, 16 (as shown in FIG. 2, referred to as a "second" configuration).

The position of the springs 22 relative to the first and second engaging components 12, 16 has the potential to significantly affect the overall width of the restraining device 10. For example and without limitation, when the springs 22 are positioned in the substantially perpendicular position (i.e., a "second" configuration), the restraining device 10 may have a width that is more than twice the width of the same restraining device 10 when its springs 22 are positioned in the substantially parallel position. Accordingly, the rotational coupling of the rods 24 with the first and second engaging components 12, 16 provides a clinician with the ability to manipulate the overall width of the restraining device 10 during laparoscopic delivery and/or implantation and further enables the restraining device 10 to be applied to tissues and/or organs having a length that is longer than the length of the restraining device 10 (as the proximal ends 13, 17 and the distal ends 14, 18 of the first and second engaging components 12, 16 of the restraining device 10 are not obstructed by the springs 22). In at least one embodiment, the widest part of the restraining device 10 is less than about 15 millimeters when the springs 22 are in the substantially parallel position such that the restraining device 10 can be easily inserted into a body cavity through a 15 millimeter trocar or port.

Figure 3A:
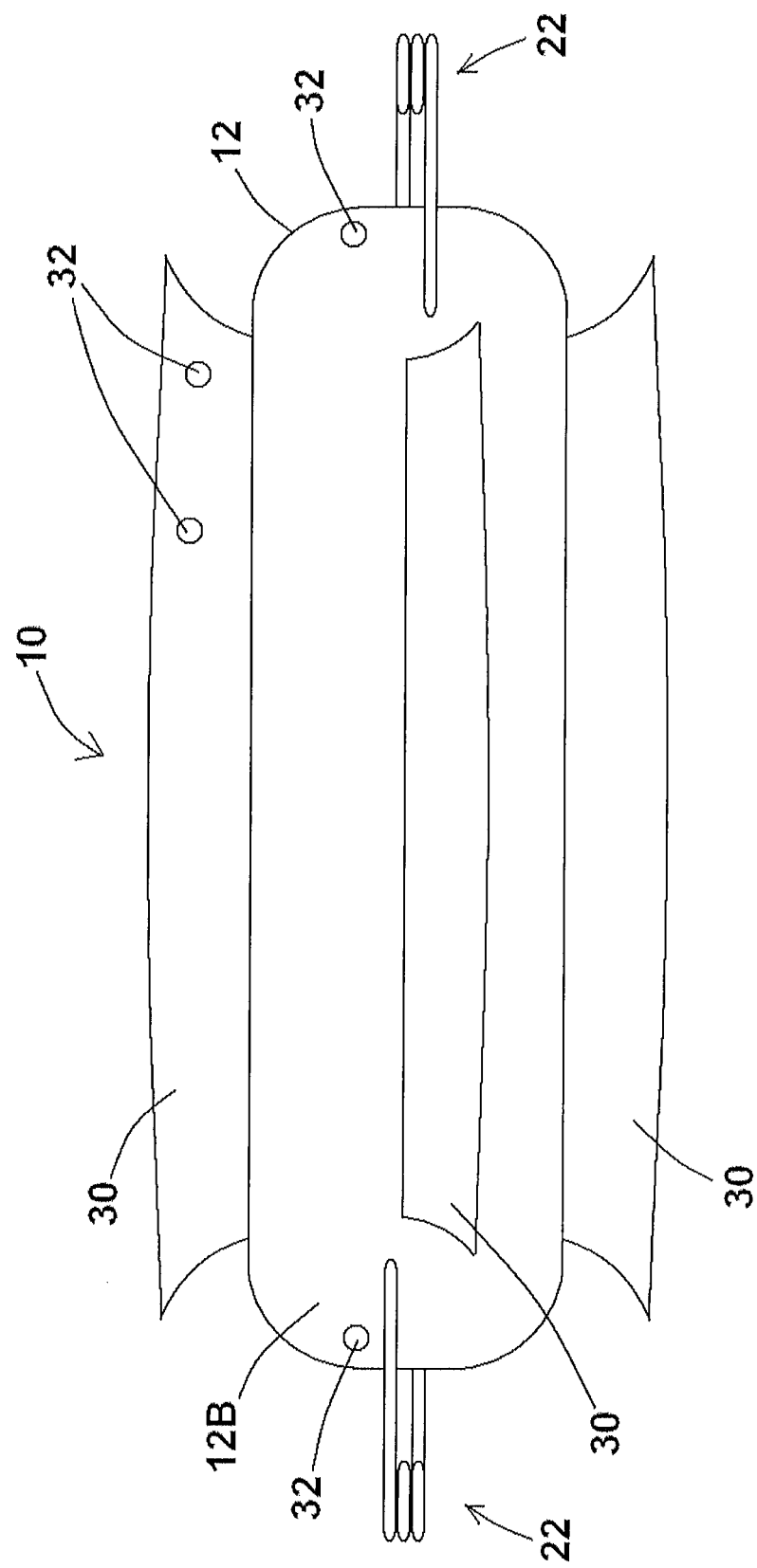
FIG. 3A shows a top view of at least one embodiment of a restraining device for restoring and/or supporting a tissue or organ according to the present disclosure.

Now referring to FIG. 3A, a top view of at least one embodiment of a restraining device 10 of the present disclosure is shown. Here, the first and/or second engaging components 12, 16 of the restraining device 10 further comprise one or more pads 30 extending therefrom. As shown in FIG. 3A, the one or more pads 30 may extend in a perpendicular fashion from the second side(s) 12B, 16B of the components 12, 16 and/or in a lateral fashion from the components 12, 16. Each of the pads 30 are comprised of a flexible material and configured to provide an anchor through which sutures or any other type of anchoring device may be inserted. For example, and in at least one embodiment, one or more pads 30 may be comprised of polyurethane or any other material that is capable of securely holding sutures or another type of anchoring device therein. One or more sutures may be placed within suture apertures 32 as shown in FIG. 3A, whereby said suture apertures 32 may be positioned along pads 30 and/or one or both of components 12, 16 as shown in FIG. 3A. Accordingly, after the first and second engaging components 12, 16 are properly positioned about a targeted tissue or organ, sutures may be inserted through suture apertures 32 and secured to a superficial layer of the underlying targeted tissue or organ to assist in anchoring the restraining device 10 in the proper location thereon.

Figure 3B:
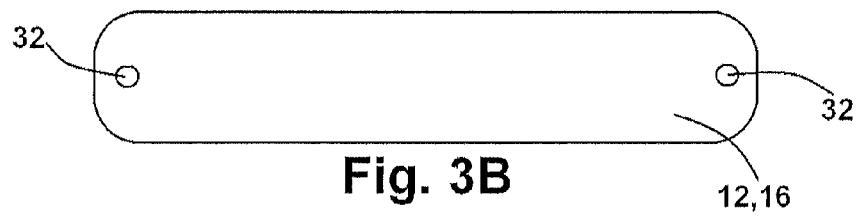
FIGS. 3B through 3E show various embodiments of engaging components according to the present disclosure.

FIGS. 3B-3E show various embodiments of first engaging component 12 and/or second engaging component 16 with various features to facilitate suturing and/or connection of first engaging component 12 to second engaging component 16. FIG. 3B shows an exemplary embodiment if a first and/or second engaging component 12, 16 comprising suture apertures 32 positioned therethrough. Suture apertures 32 are not limited to positioning near one or more of the ends of said first and/or second engaging component 12, 16, as such suture apertures 32 may be positioned along first and/or second engaging component 12, 16 as desired.

Figure 3C:
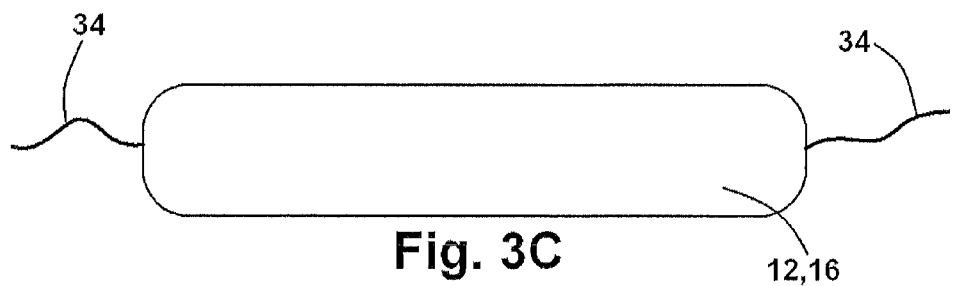
Figure 4A:
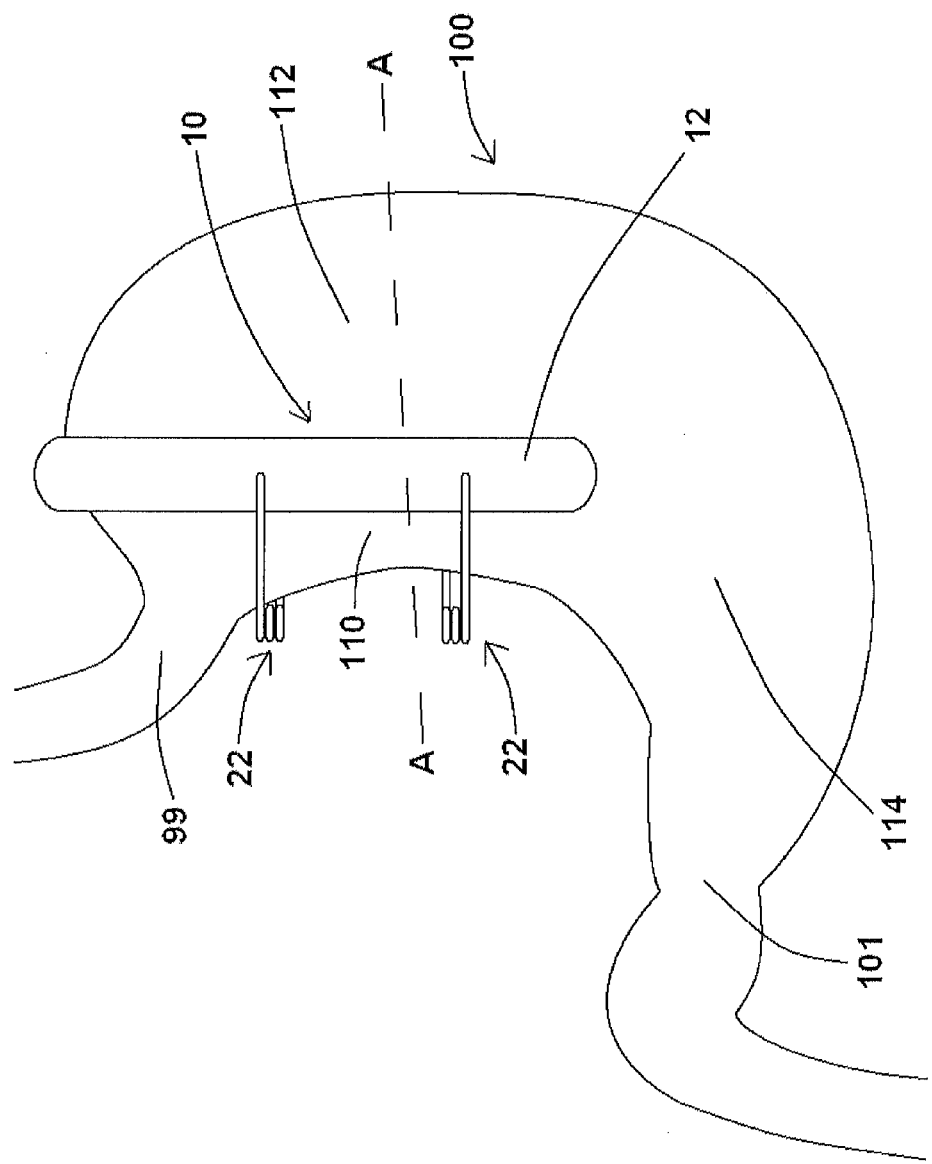
FIG. 4A shows a side view of the restraining device of FIGS. 1A and 1B applied in a longitudinal fashion to a stomach according to the present disclosure.
Figure 4B:
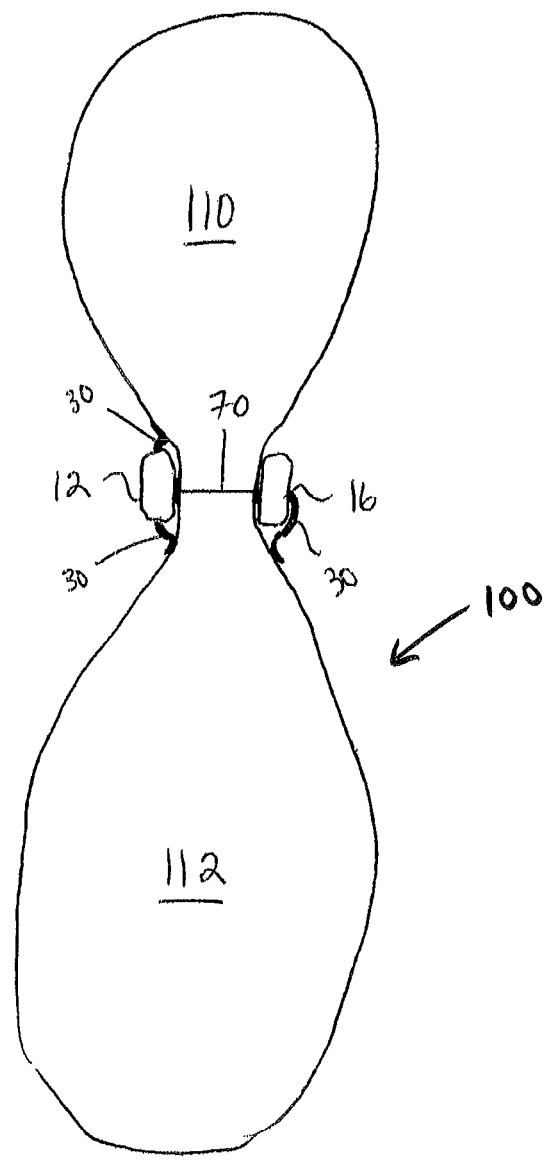
FIG. 4B shows a cross-sectional view of a restored stomach along line A-A of FIG. 4.

FIG. 3C shows an exemplary embodiment of a first and/or second engaging component 12, 16 comprising one or more strings 34 affixed thereto. In the exemplary embodiment shown in FIG. 3C, two strings 34 are shown at or near the ends of first and/or second engaging component 12, 16, noting, however, that one, two, or more strings 34 may be affixed thereto and positioned as desired. In an exemplary embodiment of a restraining device 10, and as shown in FIG. 4B, the first engaging component 12 and the second engaging component 16 may each comprise at least one string 34, whereby said strings 34 may be connected to one another to facilitate a desired placement of restraining device 10 about a stomach 100.

Figure 3D:
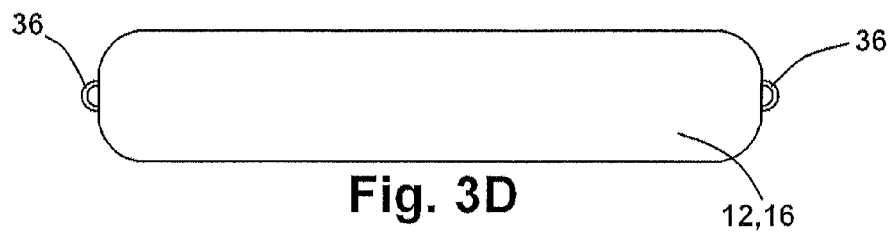
Figure 3E:
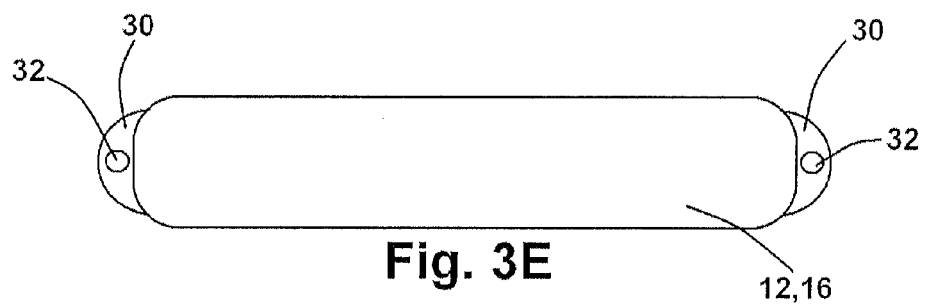

Additional embodiments of exemplary first and/or second engaging components 12, 16 are shown in FIGS. 3D and 3E. As shown in FIG. 3D, first and/or second engaging component 12, 16 comprises one or more suture members 36 affixed thereto, with said suture members defining an aperture to which a suture (not shown) or other restraining component may be affixed thereto. FIG. 3E shows an exemplary first and/or second engaging component 12, 16 of the present disclosure comprising pads 30 positioned at or near each end of the first and/or second engaging component 12, 16 with each pad 30 defining a suture aperture 32 therethrough. Additional embodiments of first and/or second engaging component 12, 16 comprising features to allow for a suture or other restraining component to be positioned therethrough are also contemplated by the present disclosure. For purposes of the present disclosure, the term "suturing elements" shall mean any number of elements for introducing a suture into the first and/or second engaging component 12, 16 and/or one or more pads 30 affixed thereto, including, but not limited to, one or more apertures 32, strings, 34, and/or suture members 36. In addition, any number of the features of the various exemplary first and/or second engaging components 12, 16 shown in FIGS. 3A-3E may appear in any number of embodiments of restraining devices 10 of the present disclosure.

In operation, the restraining device 10 may be applied to an organ or tissue of interest in order to restore the underlying tissue or organ into a desired configuration and/or provide support to the same. As discussed in further detail below, the restraining device 10 may be used for temporary or chronic implantation within a body without the risk of the first and second engaging components 12, 16 migrating through or damaging the underlying tissue. Furthermore, because the restraining device 10 does not require that the underlying tissue be punctured in any significant manner to achieve restoration and/or provide support thereto, implantation of the restraining device 10 is entirely reversible and, if desired, the restraining device 10 may be easily removed from the organ or tissue of interest through a laparoscopic procedure.

As previously described, the specifications of the restraining device 10 may be modified to achieve a desired result. For example, and without limitation, the dimensions of the components 12, 16 and/or the springs 22 may be chosen for a particular application and/or based on the patient. Accordingly, while certain embodiments of the restraining device 10 may be described in connection with particular tissues or organs, it will be appreciated that any of the embodiments of the restraining device 10 described herein may also be applied to any tissue or organ of interest in a similar manner and use of the particular embodiments of the restraining device 10 in lieu of others may be determined based on the patient's specifications, the specific application, and/or the tissue or organ in question.

In practice, an exemplary restraining device 10 is capable of restoring and/or supporting an underlying tissue while avoiding constriction and the excessive compression thereof. For example, the restraining device 10 may be applied to a stomach 100 as shown in FIGS. 4A and 4B. In at least one embodiment, and as shown in FIG. 4A, the springs 22 of the restraining device 10 are rotated to the substantially perpendicular position such that the interior space 70 is increased between the first and second engaging components 12, 16. Thereafter, the restraining device 10 may be advanced over the stomach 100 such that, for example, the first side 12A of the first engaging component 12 is positioned adjacent to the anterior wall of the stomach 100 and the first side 16A of the second bar 16 is positioned adjacent to the posterior wall of the stomach 100. While the restraining device 10 is shown in FIG. 4A in a longitudinal placement with respect to the stomach 100, it will be understood that the restraining device 10 may alternatively be positioned in a horizontal configuration or an angular configuration with respect to the stomach 100.

After the first and second engaging components 12, 16 are positioned in the desired location with respect to the stomach 100, the overall interior space 70 may either comprise its original native interior space 70 or a relatively larger interior space 70 due to the positioning of the restraining device 10 about the stomach 100. Therefore, various embodiments of restraining device 10 do not operate to "clamp" the stomach 100 or any other tissue or organ, as restraining device 10 merely operates, when positioned around a stomach 100, to provide a limited pressure, if any, to maintain a native size/shape of at least a portion of the stomach 100. For example, and depending upon the prescribed value of the interior space 70 as desired by a clinician, the configuration of the springs 22 can be modified to achieve a restraining device 10 that either does not compress, or only loosely compresses, the sandwiched tissue between the first and second engaging components 12, 16. In a preferred embodiment, restraining device 10, when positioned about a stomach 100, does not provide any meaningful compressive pressure upon the stomach 100, and may be held in place, for example, using one or more sutures as referenced herein. In this manner, the restraining device 10 can be employed to reversibly restore an organ or tissue without forming adhesions thereon and/or permanently restoring the same.

In at least one embodiment, and depending on the configuration of the springs 22, the springs 22 may exhibit enough elasticity to enable the first and second engaging components 12, 16 to move to some degree in conjunction with any movement of a tissue or organ positioned between the first and second engaging components 12, 16 of the restraining device 10. In this manner, the springs 22 can allow, for example, the restraining device 10 to accommodate any inherent movement in the stomach 100 such that application of the restraining device 10 does not completely inhibit the normal digestive function of the same. For example, the introduction of food into the stomach 100 may cause the outer dimensions of the stomach 100 to expand, whereby stomach 100 exerts a pressure upon restraining device 100. Furthermore, the restraining device's 10 ability to accommodate any inherent movement in the underlying organ and/or tissue increases the likelihood that the restraining device 10 will remain in its desired location on the tissue and/or organ without sheering off or sliding therefrom.

In the event it is desired that the restraining device 10 is further secured to the underlying tissue, and as previously referenced herein, a clinician can employ sutures to assist with the secure implantation of the restraining device 10 in the desired location. In the at least one embodiment of the restraining device 10 comprising the one or more pads 30, a clinician can secure the one or more pads 30 of the first and second engaging components 12, 16 to the underlying tissue through the use of superficial sutures. In this manner, the superficial sutures can be affixed through the one or more pads 30 and the surface of the underlying tissue such that the one or more pads 30 assist with anchoring the restraining device 10 in position on the tissue of interest. Conversely, and in at least one embodiment, sutures may be introduced directly to the first and/or second engaging components 12, 16 to secure a restraining device to a tissue or organ of interest as shown in FIGS. 3A-3E.

Figure 5A:
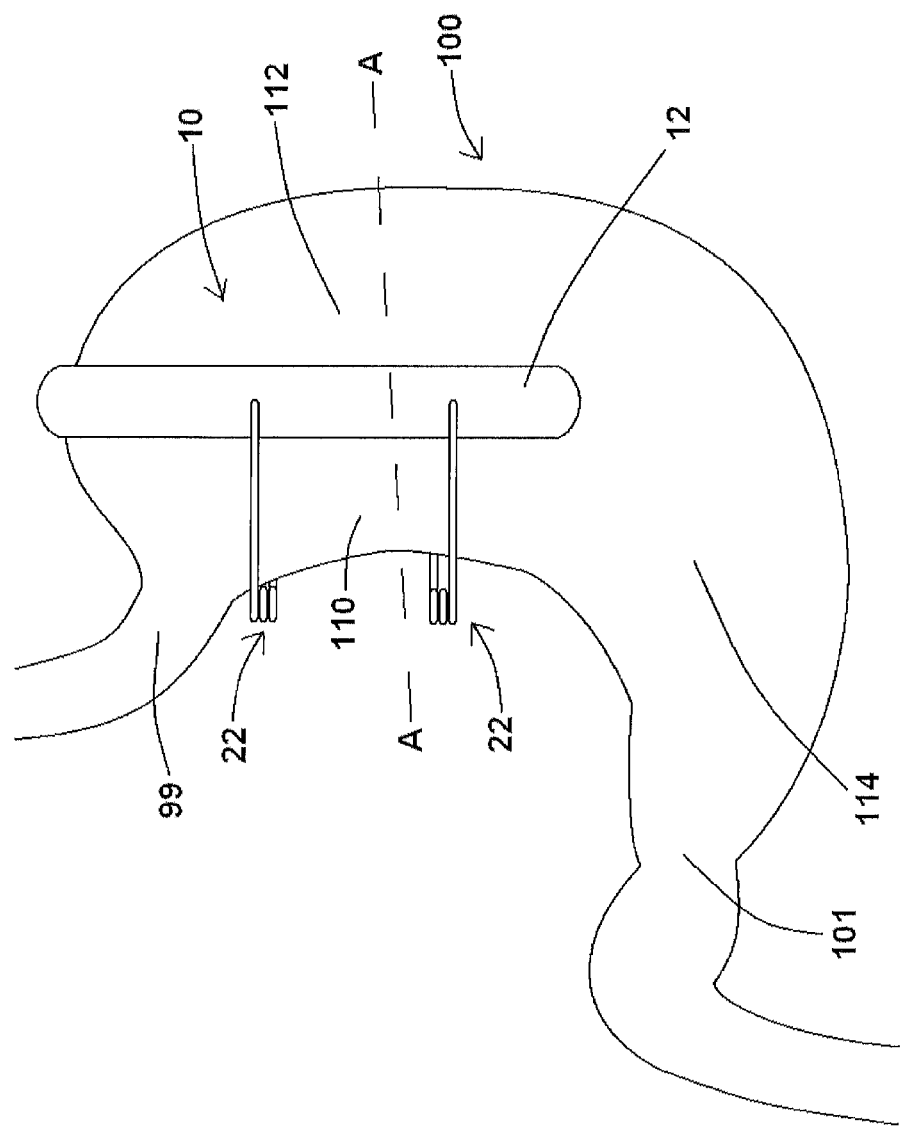

FIG. 4B shows a cross-sectional view of the stomach 100 of FIG. 4A taken along A-A. As shown in FIG. 4B, when the first and second engaging components 12, 16 of the restraining device 10 are longitudinally positioned on the stomach 100, the stomach 100 is "divided" into two portions—a first stomach portion 110 and a second stomach portion 112 as shown in FIGS. 4A and 4B. In the embodiment shown in FIGS. 4A and 4B, the first stomach portion 110 is relatively smaller than the second stomach portion 112. However, and as shown in FIG. 5A, the first stomach portion 110 and the second stomach portion 112 may be approximately the same size.

As the first stomach portion 110 receives ingested matter directly from the gastroesophageal junction 99 as shown in FIG. 4A, the placement of the restraining device 10 as shown in FIG. 4B thus inhibits the majority of ingested matter from moving into the second stomach portion 112. Instead, and in at least one embodiment, such ingested matter is directed through the smaller, first stomach portion 110 and into the pyloric canal 101 (as shown in FIG. 4A) where a significant portion of the ingested matter is evacuated from the stomach 100. Due to the size of the first stomach portion 110, the amount of food that the patient can consume at one time is significantly reduced and satiety is more quickly achieved.

While the delineation formed by the restraining device 10 between the first stomach portion 110 and the second stomach portion 112 is not leak-proof, the interior space 70 created between the first and second engaging components 12, 16 comprises an area that is less than the diameter of a fully extended stomach 100 (as shown in FIG. 4B). Accordingly, when the restraining device 10 is applied in a longitudinal fashion to a stomach 100, restraining device 10 provides support to the anterior and posterior walls of the stomach 100, with the expansion of stomach 100 exerting a force onto the first and second engaging components 12, 16 of restraining device 10, this preventing stomach 100 distension in that area. In this manner, most of the food matter received into the first stomach portion 110 through the gastroesophageal junction 99 is maintained therein and the patient exhibits the sensation of satiety earlier.

Referring back to FIG. 4A, and in at least one exemplary embodiment, because the restraining device 10 does not extend along the entire length of the stomach 100, an outflow tract 114 is formed caudally of the restraining device 10. This outflow tract 114 allows the portion of ingested matter that flows from the gastroesophageal junction 99 into the second stomach portion 112 to be evacuated from the stomach 100 in a controlled manner and to proceed through normal digestion. In addition, the outflow tract 114 allows any food matter or enzymes residing within the second stomach portion 112 to evacuate the stomach 100.

Figure 5B:
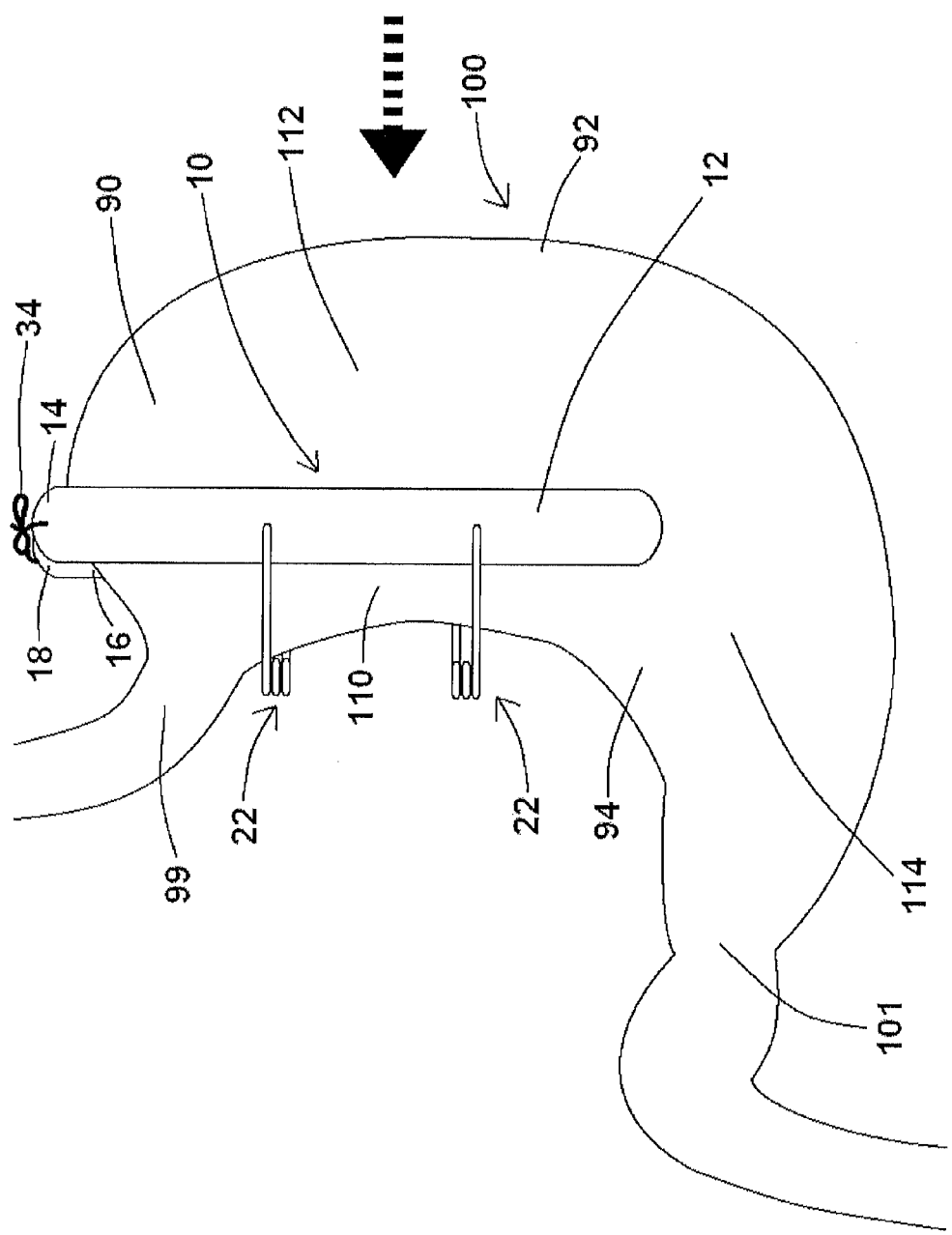
Figure 5C:
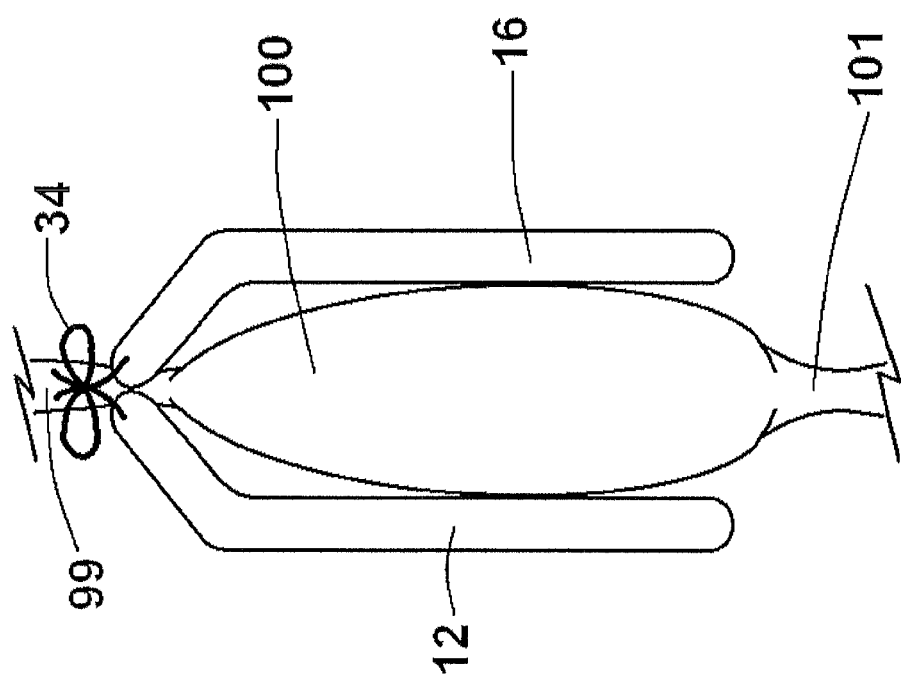

Additional embodiments of restraining devices 10 of the disclosure of the present application positioned about a stomach 100 are shown in FIGS. 5B and 5C. In the exemplary embodiment shown in FIG. 5B, restraining device 10 comprises first and second engaging components 12, 16 which are "longer" than those shown in FIG. 5A, whereby distal end 14 of first engaging component 12 and distal end 18 of second engaging component 16 extend past stomach 100. In this exemplary embodiment, strings 34 affixed to first and second engaging components 12, 16 may be connected/tied to each other after restraining device 10 has been positioned about a stomach, maintaining restraining device 10 in place.

FIG. 5C shows restraining device 10 positioned about stomach 100 viewed in the direction of the arrow shown in FIG. 5B. As shown in FIG. 5B, the tying/coupling together of strings 34 at the distal ends 14, 18 of first and second engaging components 12, 16 may cause portions of the first and second engaging components 12, 16 to angle towards one another as shown in FIG. 5C. In this particular embodiment, first and second engaging components 12, 16 are flexible or semi-flexible, and the positioning of restraining device 10 about stomach 100 serves to isolate the first stomach portion 110 from fundus 90 and greater curvature 92. This "funnel" effect, in addition to the embodiment of a restraining device 10 shown in FIG. 5D below, may also be accomplished by having springs 22 with relatively shorter rods 24 (or relatively smaller struts 700 as referenced in various embodiments herein) at one end of restraining device 10, and by having springs 22 with relatively longer rods 24 (or relatively larger struts 700 as referenced in various embodiments herein) at the other end of restraining device 10. In addition as to being substantially rigid as shown in FIGS. 1 and 2, and as shown in FIG. 5C, first and second engaging components 12, 16 may have substantially rigid center portions and one or more flexible or semi-flexible ends, or first and second engaging components 12, 16 may be flexible or semi-flexible along the entirety of said components 12, 16.

An additional embodiment of a restraining device 10 of the present disclosure positioned about stomach 100 is shown in FIG. 5D. As shown in FIG. 5D, and as also discussed herein regarding FIG. 10, restraining device 10 further comprises a pliable junction 1000 positioned within the first engaging component 12 and second engaging component 16, effectively "splitting" each component, whereby each "split" component is connected to one another by way of a flexible structure 1002. As shown in FIG. 5D, flexible structure 1002 may comprise a PTFE band or a PTFE mesh, for example, whereby any potential embodiment of flexible structure 1002, using one or more pliable materials disclosed herein or otherwise known in the art, allows the relatively or fully rigid first engaging component 12 and second engaging component 16 to better fit the stomach, allowing the patient, for example, to bend the stomach when restraining device 10 is positioned thereon.

Approximating first and second engaging components 12, 16, as shown in FIGS. 5B, 5C, and 5D, and as identified during internal testing of exemplary restraining devices 10 of the present disclosure, leads to reduced food intake (65-70% of normal food intake) as compared to positioning restraining device 10 about stomach 100 without approximating first and second engaging components 12, 16 toward one another as shown in FIG. 4A (80-85% of normal food intake). This approximation also assists with the prevention of a fistula so that the food may move down the pouch (first stomach portion 110) along antrum 94 as opposed to shunted to the fundus 90 of stomach 100.

As described herein, application of the restraining device 10 allows a clinician to restore a targeted tissue, such as a stomach 100, while avoiding constriction and excessive compression of the same. Further, the various embodiments described herein allow a clinician to tailor the restraining device 10 to multiple restoration applications and various different types of tissues. Permanent restoration of the tissue is avoided, which prevents adhesions from developing in the underlying targeted tissue and allow for the complete reversal of the restoration procedure. Additionally, the restraining device 10 is simple to deliver and, as such, the device 10 may be used in conjunction with other techniques or surgical procedures.

Regarding the application of the restraining device 10 to the stomach 100, use of the restraining device 10 in the treatment of obesity avoids the nutritional and metabolic deficiencies observed after Malabsorptive Procedures because the digestive process may continue within the stomach as with a native stomach 100. In addition, the restraining device 10 does not require more than superficial punctures to the underlying tissue, nor does it employ pins, staples or significant sutures which may lead to dehiscence or fistula formation, or produce the degree of regurgitation and vomiting observed in connection with conventional methods used to treat obesity. Moreover, each of the embodiments described herein may be inserted into the body cavity laparoscopically, thereby decreasing the patient's stress associated with the procedure and the patient's recovery time. It will be recognized that any of the devices described herein may be employed in combination with other conventional bariatric procedures.

Figure 6:
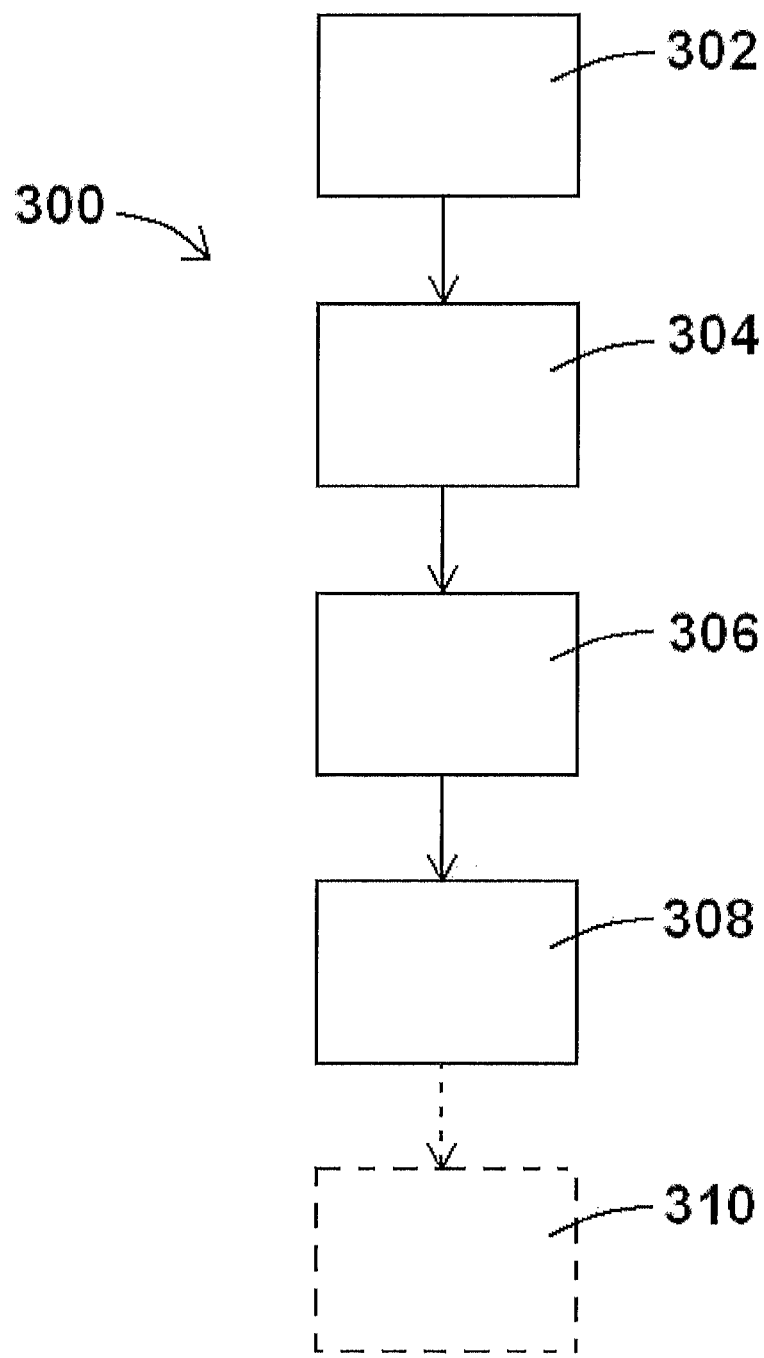
FIG. 6 shows a flow chart of a method for laparoscopically delivering embodiments of the restraining device disclosed herein to a targeted tissue according to the present disclosure.

Now referring to FIG. 6, a flow chart of a method 300 for laparoscopically delivering the restraining device 10 is shown. For ease of understanding, the steps of the related methods described herein will be discussed relative to the components of an exemplary restraining device 10. Furthermore, while the methods described herein are described in connection with embodiments of the restraining device 10 and an exemplary delivery device, it will be appreciated that various additional devices may be used to facilitate the laparoscopic delivery of the restraining device 10 such as a camera, light and/or a device for delivering a gas to a targeted area.

At step 302, the first and second engaging components 12, 16 of restraining device 10 are advanced laparoscopically into the patient's body. In at least one embodiment, the restraining device 10 may be inserted through a 15 millimeter cannula under insufflation into the appropriate cavity of the patient's body. This may be achieved through use of an exemplary delivery device known in the art. At this step 302, the springs 22 of the restraining device 10 are positioned in the substantially parallel position such that the overall diameter of the restraining device 10 is sufficiently narrow for insertion into the body.

At step 304 the restraining device 10 is advanced to a location adjacent to a targeted tissue. In the at least one embodiment of the method 300 where an exemplary delivery device is employed to facilitate delivery of the restraining device 10 to the targeted tissue, at step 304 the restraining device 10 is advanced out of the delivery device and into the body cavity. After the restraining device 10 is no longer positioned within an exemplary delivery device, the delivery device may be withdrawn from the body cavity at this step 304 or as desired by the clinician.

At step 306, the springs 22 of the restraining device 10 are rotated from the substantially parallel position to the substantially perpendicular position, separating the first and second engaging components 12, 16 from one another to a native interior space 70. Step 306 may be performed using any number of standard laparoscopic tools known in the art useful to pull and grasp portions of a tissue or a device. In this manner, neither the proximal ends 13, 17 nor distal ends 14, 18 of the first and second engaging components 12, 16 of the restraining device 10 are blocked by the springs 22 and/or rods 24, and the first and second engaging components 12, 16 may be advanced over a targeted tissue having a length that is greater than the overall length of the first and second engaging components 12, 16.

At step 308, under fluoroscopic, direct camera control or otherwise, the restraining device 10 is advanced over the targeted tissue. In at least one embodiment, and at step 308, the first side 12A of the first engaging component 12 is positioned adjacent to the desired surface of the targeted tissue and the first side 16A of the second engaging component 16 is positioned adjacent to an opposite side of the targeted tissue. As the first and second engaging components 12, 16 of the restraining device 10 are positioned adjacent to opposite sides of the targeted tissue, at this step 308 the targeted tissue is positioned within the interior space 70 formed between the first and second engaging components 12, 16. Accordingly, while the targeted tissue may experience some compressional force exerted by the first and second engaging components 12, 16 of the restraining device 10, the majority of the pressure upon the first and second engaging components 12, 16 is provided by distension/expansion of the targeted tissue (for example, expansion of a stomach 100 when food is introduced therein). Further, due to the configuration and composition of the restraining device 10, the restraining device 10 can remain within the patient's body for as long as the restoration or support treatment delivered thereby is desired.

If preferred, in at least one embodiment of the restraining device 10 that further comprises one or more pads 30 coupled with the first and/or second engaging components 12, 16, the method 300 may advance from step 308 to step 310. At step 310, a clinician can employ sutures to further anchor and secure the restraining device 10 in the desired position on the targeted tissue. These sutures need only superficially puncture the underlying tissue and therefore are not associated with the negative effects associated with suturing, stapling and/or the insertion of pins used in conventional methods.

Additional embodiments of restraining devices 10 of the disclosure of the present application is shown in FIGS. 7A and 7B. As shown in FIGS. 7A and 7B, restraining device 10 comprises a first engaging component 12 and a second engaging component 16, whereby the first engaging component 12 and second engaging component 16 are coupled to one another by way of one or more struts 700. In the exemplary embodiment shown in FIGS. 7A and 7B, four struts 700 and five struts 700 are used, respectively, but any number of struts 700 may be used as desired for a particular application. Struts 700 may comprise any number of suitable materials as otherwise described herein, including, but not limited to, nitinol and stainless steel. Struts 700, in an exemplary application, would have a pre-established "open" size and a pre-established "strength", so that restraining device, in a native "rest" configuration, would be "open" (by way of, for example, the "memory" of struts 700) and would require some sort of pressure/force to open even further. The "open" configuration would keep first engaging component 12 and second engaging component 16 a fixed distance apart to avoid gastric tissue compression when positioned about a stomach.

An exemplary restraining device 10 may further comprise a mesh curtain 702 coupled to struts 700 as shown in FIGS. 7A and 7B. Mesh curtain 702 may prevent or limit potential organ distension or remodeling when restraining device 10 is positioned about an organ of interest. A demi shaft 704, as shown in FIGS. 7A and 7B, may be positioned around at least part of struts 700 and/or mesh curtain 702 to facilitate insertion of restraining device 10 within a body. For example, and as shown in FIG. 7A, restraining device 10 may be seen as inserted within a body, noting that restraining device is somewhat compressed by demi shaft 704, to facilitate insertion through, for example, a laparoscopic port. After insertion, and as shown in FIG. 7B, demi shaft 704 may be withdrawn in the direction of the arrow (shown as partially withdrawn in the figure) to allow restraining device 10 to obtain its original, uncompressed configuration, and ultimately removed from the body. Struts 702 may have a first configuration when positioned within demi shaft 704, as shown in FIG. 7A, and may have a second configuration when demi shaft 704 is removed, as shown on the left side of FIG. 7B.

Figure 8:
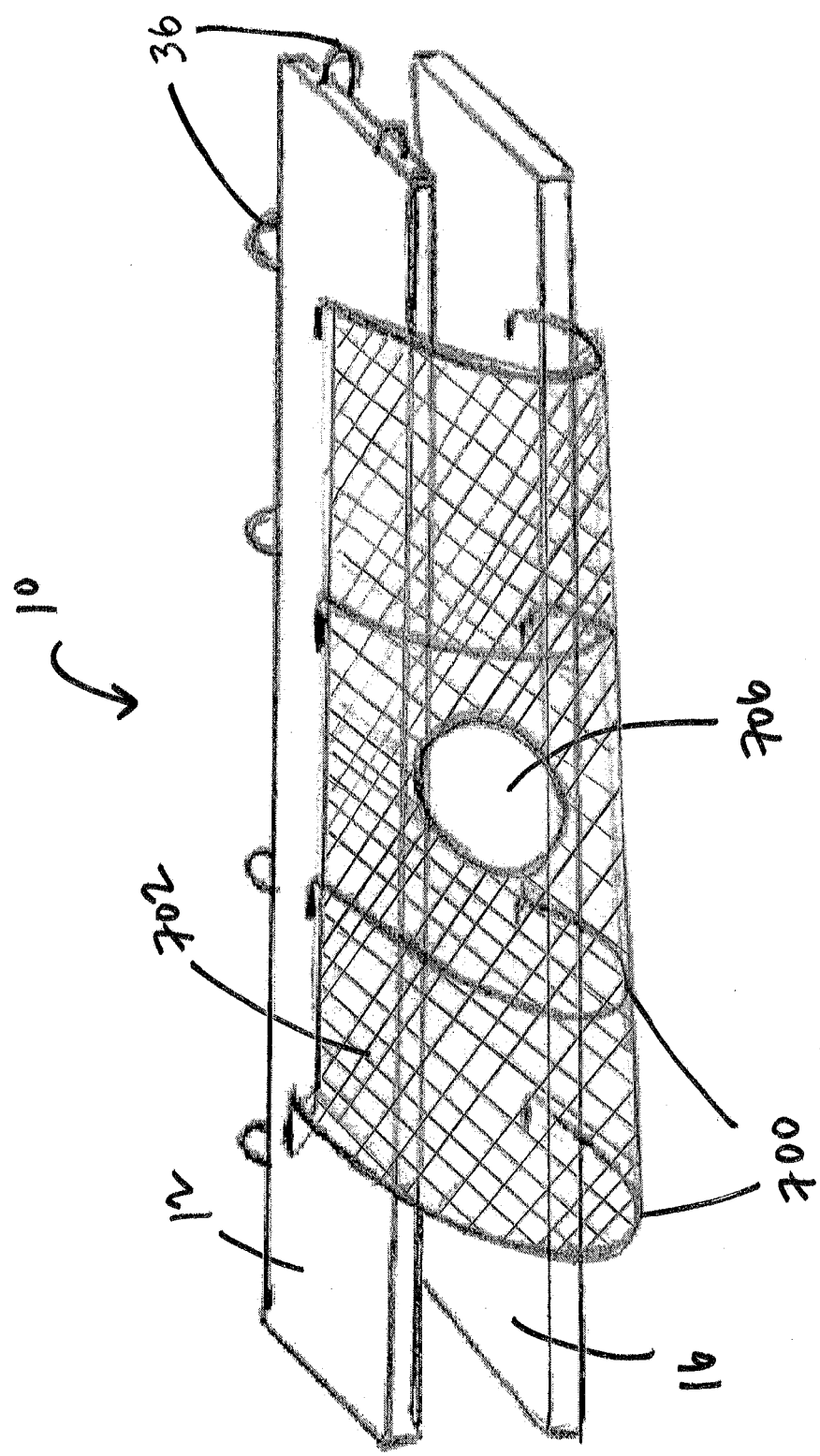

When restraining device 10 is in its native configuration, it may then be positioned about a stomach, for example, and the user positioning restraining device 10 may grasp stomach tissue using any number of laparoscopic tools through mesh aperture 706 as shown in FIGS. 7B and 8. As shown in FIG. 8, an exemplary restraining device 10 may also comprise one or more suture members 36 to allow one or more sutures (not shown) to be used to secure restraining device 10 to, for example, an anterior gastric wall.

Figure 9:
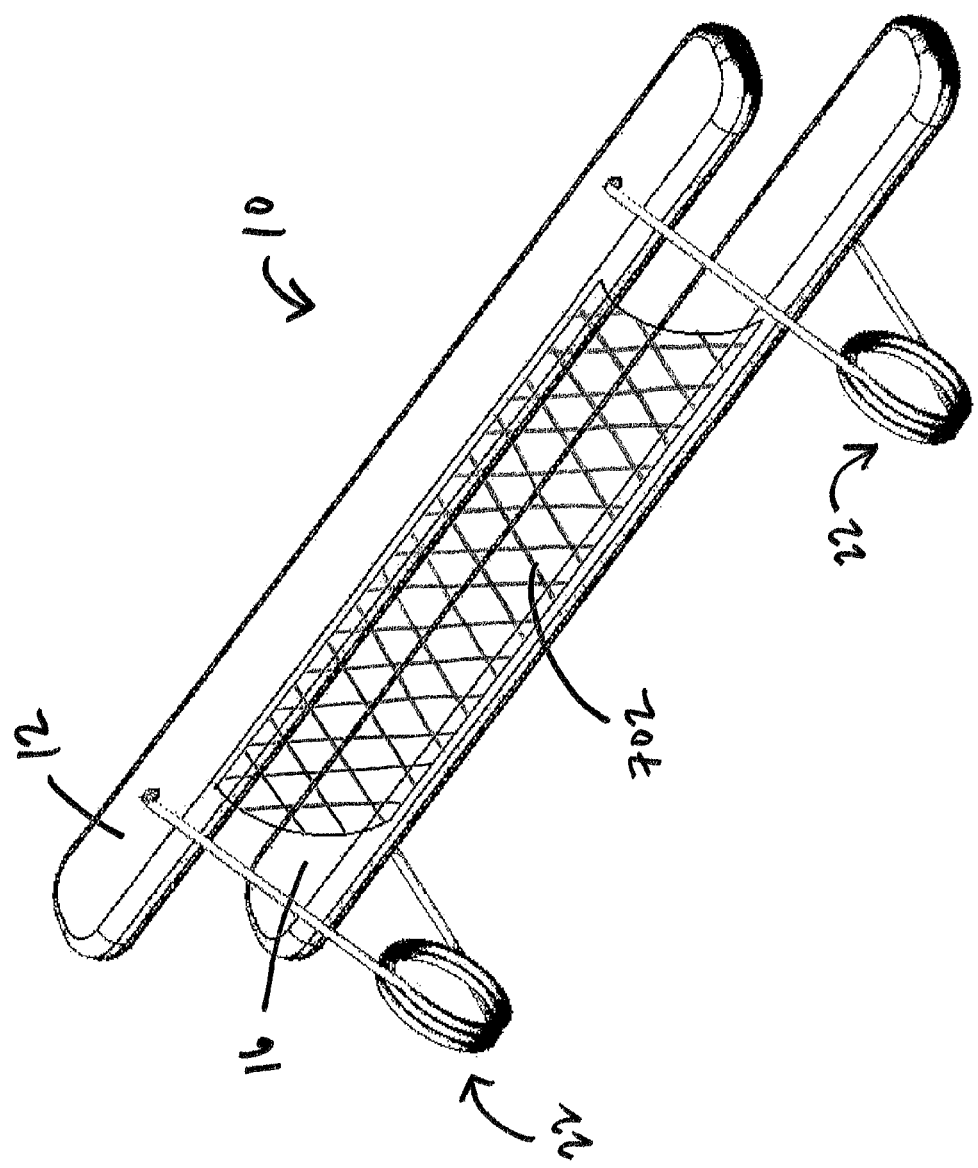
FIG. 9 shows an exemplary embodiment of a restraining device comprising two springs and a mesh curtain according to the present disclosure.

An additional embodiment of a restraining device 10 of the disclosure of the present application is shown in FIG. 9. As shown in FIG. 9, restraining device 10 comprises a first engaging component 12 and a second engaging component 16, whereby first engaging component 12 and second engaging component 16 are coupled to one another by way of one or more springs 22. In this exemplary embodiment, restraining device 10 further comprises a mesh curtain 702 coupled to first engaging component 12 and second engaging component 16, whereby mesh curtain 702 may prevent or reduce organ distension or remodeling when restraining device 10 is positioned about an organ. The flexibility/pliability of mesh curtain 702 would allow mesh curtain 702 to be closely positioned first engaging component 12 and second engaging component 16 upon insertion of restraining device 10 within a body, and may further allow mesh curtain 702 to expand in a direction of springs 22 as shown in FIG. 9, for example, to prevent organ distention.

Figure 10:
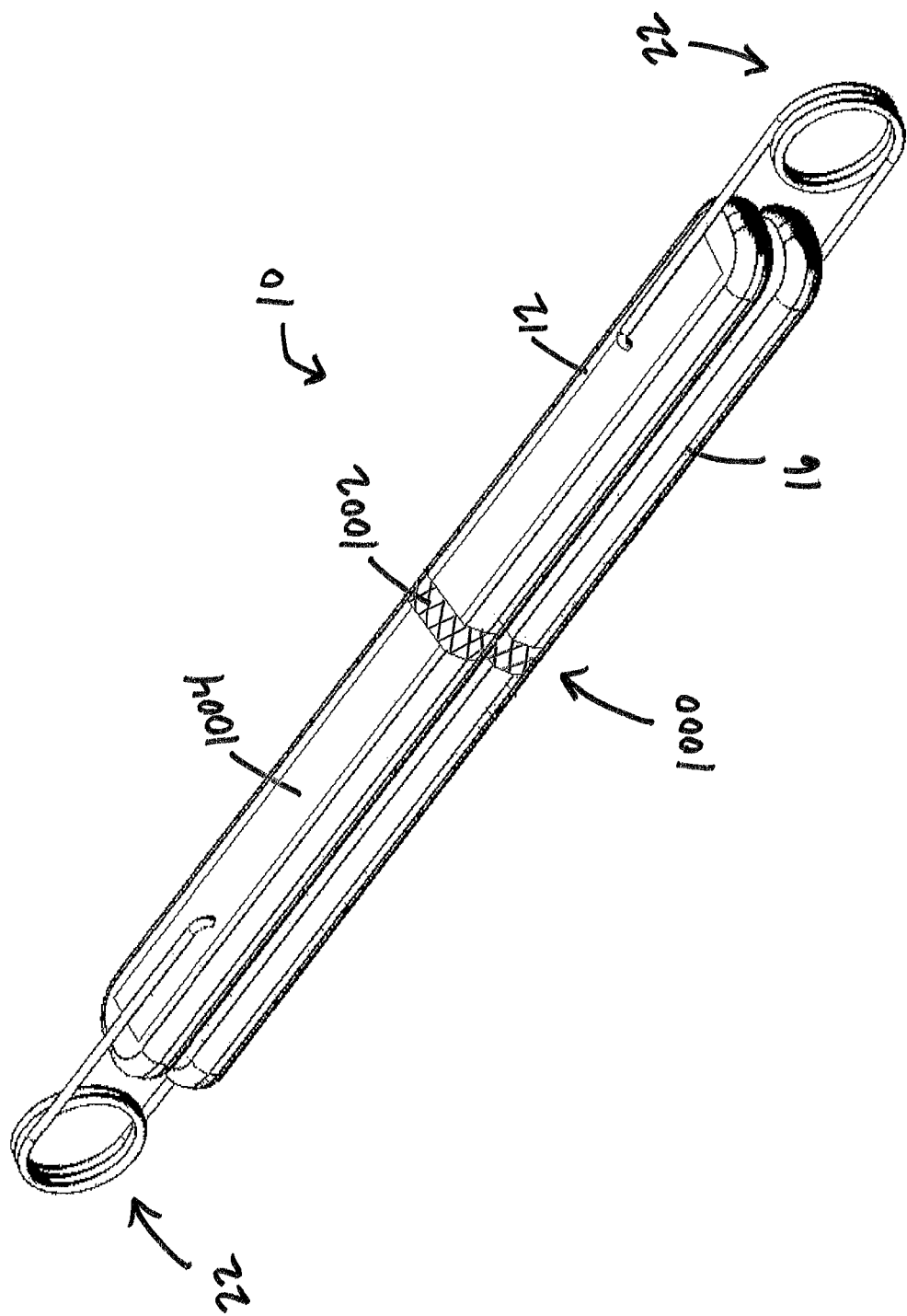
FIG. 10 shows an exemplary embodiment of a restraining device comprising a pliable junction according to the present disclosure.

FIG. 10 shows yet another embodiment of a restraining device 10 of the present application. As shown in FIG. 10, restraining device comprises a first engaging component 12 and a second engaging component 16, whereby first engaging component 12 and second engaging component 16 are coupled to one another by way of one or more springs 22. However, in this exemplary embodiment, restraining device 10 further comprises a pliable junction 1000 positioned within the first engaging component 12 and second engaging component 16, effectively "splitting" each component, whereby each "split" component is connected to one another by way of a flexible structure 1002. As shown in FIG. 10, flexible structure 1002 may comprise a PTFE band or a PTFE mesh, for example, whereby any potential embodiment of flexible structure 1002, using one or more pliable materials disclosed herein or otherwise known in the art, allows the relatively or fully rigid first engaging component 12 and second engaging component 16 to better fit the stomach, allowing the patient, for example, to bend the stomach when restraining device 10 is positioned thereon. In addition, and as shown in the exemplary embodiment in FIG. 10, restraining device 10 may further comprise a tissue cover 1004 positioned either partially or fully around either or both of first engaging component 12 and second engaging component 16.

Figure 11:
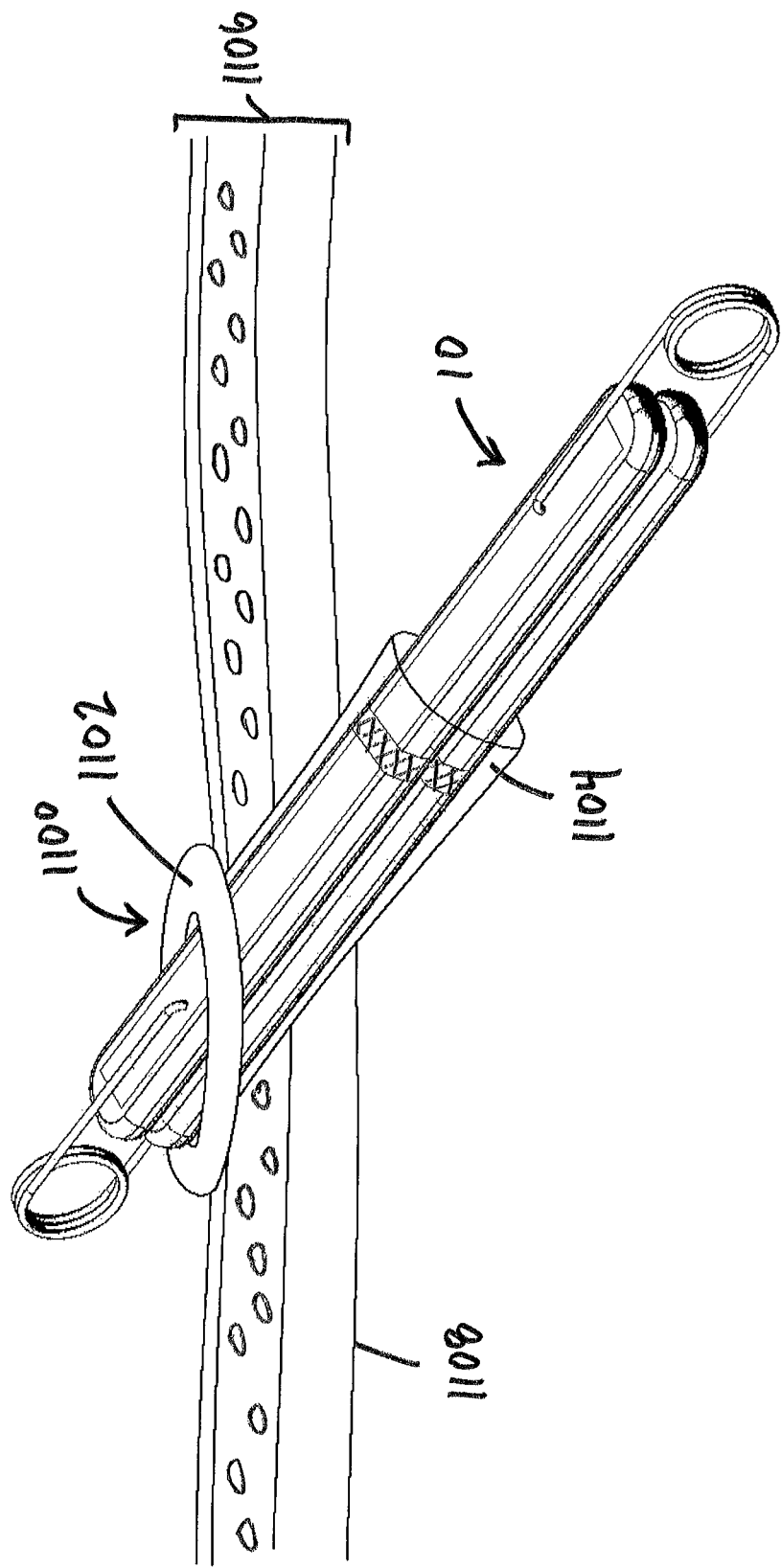
FIG. 11 shows a restraining device positioned within a laparoscopic port according to the present disclosure.

FIG. 11 shows an exemplary embodiment of a restraining device 10 of the present application positioned within a laparoscopic port. As shown in FIG. 11, restraining device 10 is shown as being inserted into a body portion by way of laparoscopic port 1100, with the exemplary laparoscopic port 1100 shown as comprising a ring 1102 and a port sleeve 1104 to facilitate introduction of restraining device 10 through an abdominal wall 1106. Viewing the figure from the outside-in, restraining device 10 is shown as being introduced into an abdomen through abdominal wall 1106, with peritoneum 1108 shown as being an innermost layer of the abdominal wall.

An additional embodiment of a restraining device 10 of the disclosure of the present application is shown in FIG. 12A. As shown in FIG. 12A, restraining device 10 comprises a first engaging component 12 and a second engaging component 16, whereby first engaging component 12 and second engaging component 16 are coupled to one another by way of one or more couplers 1200. In this exemplary embodiment, restraining device comprises two couplers 1200, shown in further detail in FIG. 12B. Couplers 1200 may comprise coupler arms 1202 connected to one another by way of a coupler bar 1204, and may comprise any number of suitable materials as described herein for various components of the present disclosure. As shown in FIG. 12A, coupler arms 1202 may be positioned within first engaging component 12 and second engaging component 16 by way of apertures 1210 (as shown in FIG. 12B) defined therein, allowing first engaging component 12 and second engaging component 16 to move relative to one another as couplers 1200 swivel when positioned at least partially within said apertures 1210.

As shown in FIG. 12B, an exemplary embodiment of a coupler 1200 may comprise a coupler protrusion 1206 at or near the end of each coupler arm 1202, whereby coupler protrusions either prevent or restrict the removal of coupler 1200 from the either first engaging component 12 or the second engaging component 16 by way of stops 1208 positioned about the first engaging component 12 and the second engaging component 16 at or near the apertures 1210 defined therein. As coupler 1200 moves in the direction of the arrow shown in FIG. 12B, coupler protrusions 1206 would engage stops 1208, thus preventing or restricting the removal of coupler 1200 from the first engaging component 12 and/or the second engaging component 16.

Insertion of the exemplary embodiment of the restraining device 10 shown in FIG. 12A into a body portion may be performed by inserting said restraining device 10 through a laparoscopic port with first engaging component 12 and second engaging component 16 either touching or nearly touching one another, and with couplers 1200 either mostly or fully inserted within apertures 1210 of restraining device 10. When restraining device has been inserted into a body portion, first engaging component 12 and second engaging component 16 may be separated a pre-established distance from one another my way of turning/swiveling couplers 1200. As such, couplers 1200, as well as first engaging component 12 and second engaging component 16, may be sized and shaped as desired for a particular application.

FIGS. 13A and 13B show an exemplary embodiment of a restraining device 10 with a coupler 1200 positioned therein in a configuration to maximize the interior space 70 between first engaging component 12 and second engaging component 16. As such, the configuration of coupler 1200 shown in FIG. 12A may be viewed as "closed," while the configuration shown in FIG. 13A may be viewed as "open." In addition, and as described above and shown in FIG. 13A, coupler 1200 may be withdrawn from apertures of first engaging component 12 and second engaging component 16 to facilitate placement of restraining device about an organ of interest, Such withdrawal may be performed using any number of laparoscopic tools, for example, whereby coupler 1200 is withdrawn up to a point where protrusions 1206 would engage stops 1208 as shown in FIG. 12B.

Another exemplary embodiment of a restraining device 10 of the disclosure of the present application is shown in FIGS. 14A and 14B. As shown in FIGS. 14A and 14B, restraining device 10 comprises a first engaging component 12 and a second engaging component 16, whereby first engaging component 12 and second engaging component 16 are coupled to one another by way of one or more couplers 1200. In the embodiments shown in FIGS. 14A and 14B, couplers 1200 comprise "scissor" couplers 1200, whereby at least two coupler bars 1204 are connected to one another via a pivot member 1400 so that coupler bars 1204 may pivot about one another at pivot member 1400. As coupler 1200 shifts from a "closed" configuration, as shown in FIG. 14A, to an "open" configuration, as shown in FIG. 14B, coupler bars 1204 pivot about pivot member 1400 causing coupler bars 1204 to move closer to one another in a direction opposite the direction of the length of first engaging component 12 and second engaging component 16.

Couplers 1200, as shown in FIGS. 14A and 14B, may "open" and "close" by way of movement of coupler arms 1202 (ends shown in the two figures) within apertures 1210 defined within first engaging component 12 and second engaging component 16. Apertures 1210, as shown in these exemplary embodiments, are configured as horizontal grooves to allow coupler arms 1202 to move closer to one another within the same aperture 1210 while coupler 1200 is "opening" and to allow coupler arms 1202 to move away from one another within the same aperture 1210 while coupler 1200 is "closing." As shown in FIG. 14B, restraining device 10, in a fully open position, would maximize the interior space 70 between first engaging component 12 and second engaging component 16. Protrusions 1402, such as teeth, indentations, and the like, may be positioned at or near apertures 1210, as shown in FIG. 14B, to facilitate fixation of coupler arms 1202 in a desired position, allowing a user positioning restraining device 10 within a body to measure the exact the interior space 70 between first engaging component 12 and second engaging component 16.

Upon insertion of the exemplary embodiment of restraining device 10 shown in FIGS. 14A and 14B within an abdominal cavity (through a laparoscopic port, for example), any number of laparoscopic tools may be used to grasp couplers 1200 to withdraw them from first engaging component 12 and second engaging component 16 as referenced herein regarding various other embodiments of restraining devices 10.

Figure 15A:
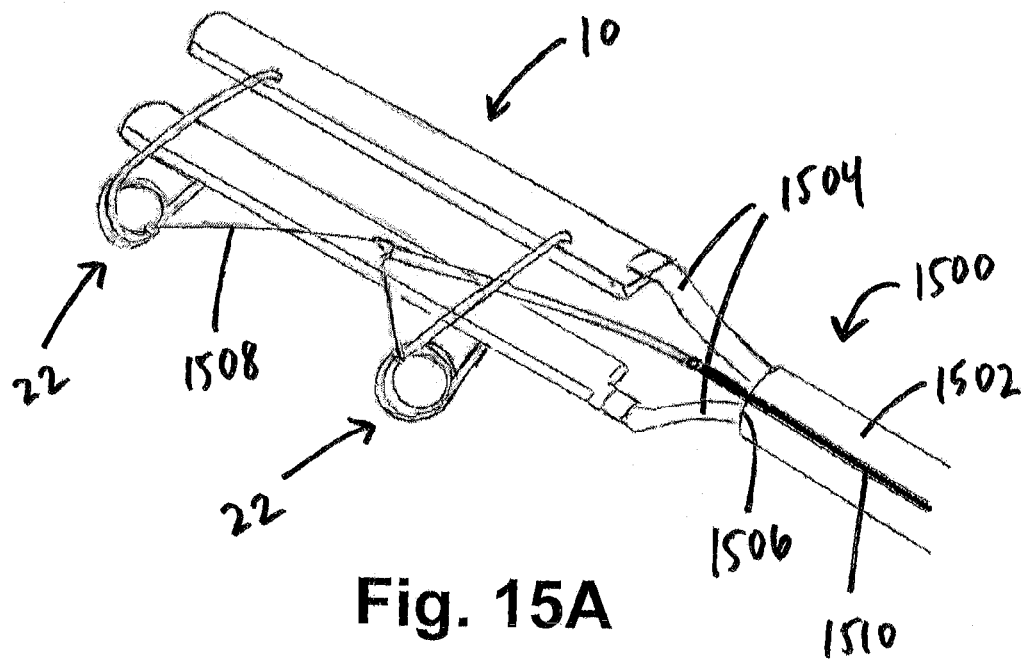
FIGS. 15A and 15B show exemplary embodiments of an apparatus for delivering a restraining device according to the present disclosure.
Figure 15B:
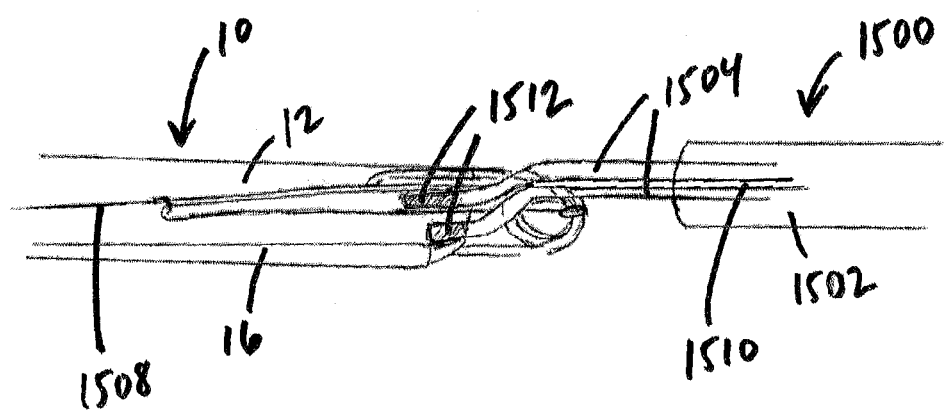

An exemplary delivery apparatus for delivering a restraining device 10 of the present application is shown in FIGS. 15A and 15B. As shown in FIG. 15A, an exemplary delivery apparatus 1500 comprises a shaft 1502 and arms 1504 at or near a distal end 1506 of shaft 1502. Apparatus 1500 may further comprise string 1508, whereby string 1508 may either be coupled to or engaged by a pull bar 1510 (an exemplary "puller" of the present disclosure) positioned within the lumen of apparatus 1500. Arms 1504 may engage an outer surface of first engaging component 12 and second engaging component 16, a protrusion (not shown) extending from said components, or by way of a groove 1512 (shown in FIG. 15B) positioned within said components.

As shown in FIG. 15A, string 1508 is coupled to springs 22 of restraining device 10, whereby a "pulling" motion of pull bar may effectively pull springs 22 from a first configuration (not shown in FIG. 15A) to a second configuration as shown in FIG. 15A so that restraining device may be positioned about an organ of interest. In an additional embodiment, string 1508 may be positioned at least partially within the lumen of apparatus 1500, whereby a user of apparatus may pull string 1508 instead of pulling pull bar 1510 to operate apparatus 1500. Various components of apparatus 1500 may comprise any number of suitable materials, including, but not limited to, the various materials referenced herein in connection with components of restraining device 10. For example, string 1508 may comprise, for example, plastic or metal thread.

For example, and in an abdominal cavity with the epiplon lesser curvature dissected, arms 1504 of apparatus 1500 may position restraining device 10 to a desired location, springs 22 of restraining device 10 may be widely opened, thus separating the first engaging component 12 and the second engaging component 16 by using pull bar 1510 to pull the strings 1508 and move springs 22 from an axial position to a 90° position relative to first engaging component 12 and the second engaging component. An "opened" restraining device 10 may then be introduced through the dissected lesser curvature space in parallel position to the intragastric mannequin tube, thus creating a desired pouch size. First engaging component 12 and second engaging component 16, upon positioning restraining device 10 about a stomach, would occupy the anterior and posterior wall of the stomach. When the first engaging component 12 and the second engaging component 16 are located in the desired position, spring 22 approximates the first engaging component 12 and the second engaging component 16 to each other gradually without producing any ischemic or tissue damage. Upon moving springs 22 to their desired location and/or positioning restraining device 10 about the stomach, restraining device 10 is separated from apparatus 1500, strings 1508 are cut and apparatus 1500 is pulled out of the abdominal cavity through the port. Restraining device 10 may then be secured in the gastric tissue with superficial stitches.

FIG. 15B shows an exemplary embodiment of at least a portion of apparatus 1500 engaging a "closed" restraining device 10. As shown in FIG. 15B, arms 1504 of apparatus 1500 are shown engaging first engaging component 12 and second engaging component 16 of restraining device 10 by way of grooves 1512 positioned within said components, permitting apparatus 1500 to deliver restraining device 10 through an abdominal port.

Figure 16A:
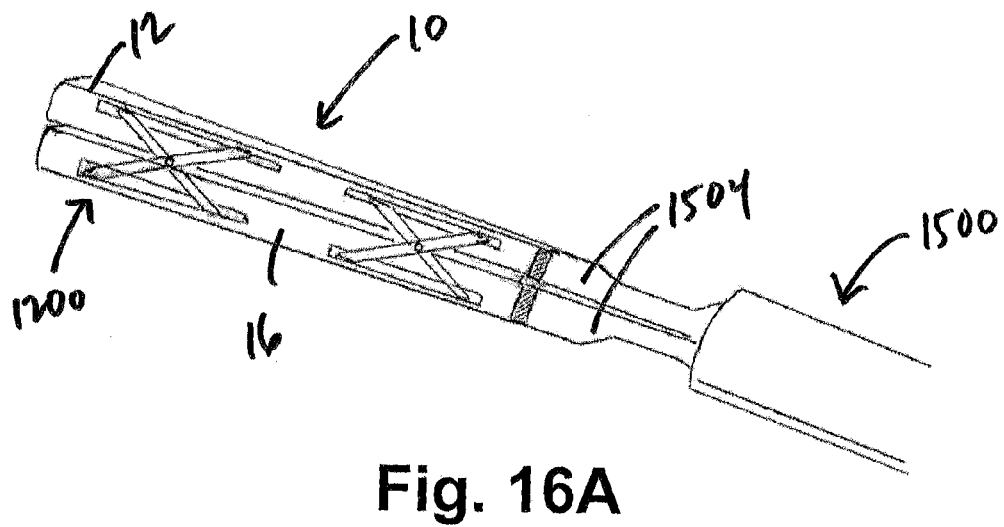
FIGS. 16A and 16B show exemplary embodiments of an apparatus for delivering a restraining device comprising a coupler according to the present disclosure.
Figure 16B:
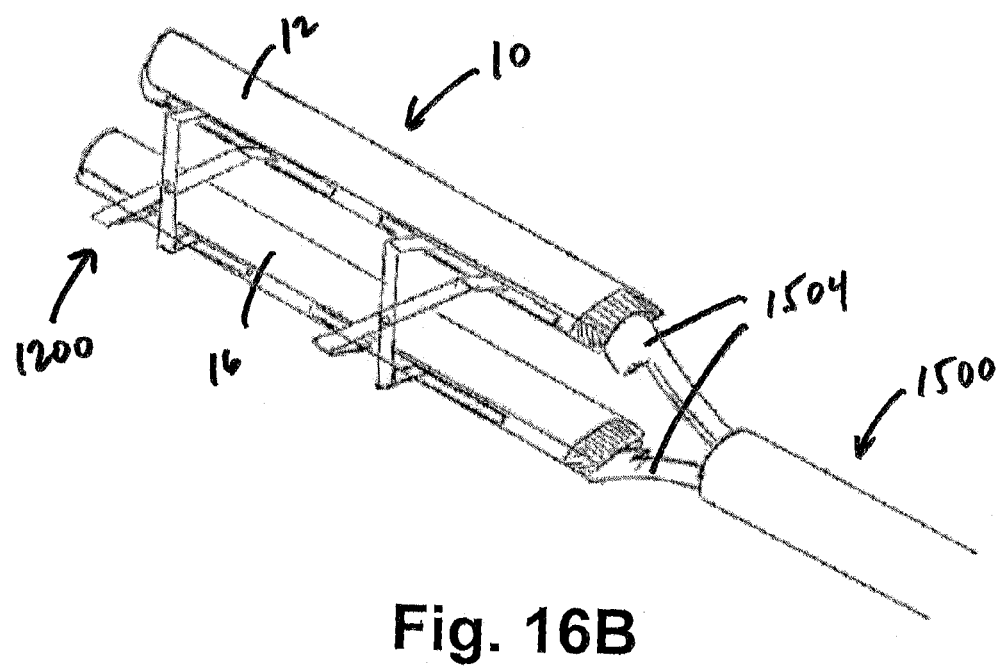

FIGS. 16A and 16B show an exemplary embodiment of an apparatus 1500 engaging/positioning an exemplary restraining device 10 of the disclosure of the present application. As shown in FIGS. 16A and 16B, arms 1504 of apparatus 1500 may engage the first engaging component 12 and the second engaging component 16 of restraining device 10, whereby the "opening" of arms 1504 would facilitate the "opening" of restraining device from a "closed" configuration (as shown in FIG. 16A) to an "open" configuration (as shown in FIG. 16B).

"Opening" restraining device 10, as shown in FIG. 16B, may be performed as follows. In the abdominal cavity with the epiplon lesser curvature dissected, the arms 1504 of apparatus 1500 may be widely opened, thus separating the first engaging component 12 and the second engaging component 16 of restraining device 10. A surgeon, for example and with the aid of laparoscopic graspers, may then "pull" out couplers 1200, placing couplers 1200 in a withdrawn configuration as shown in FIG. 16B. Restraining device 10, in an "open" configuration, may be introduced through the dissected lesser curvature space in parallel position to the intragastric mannequin tube, thus creating the desired stomach pouch size. First engaging component 12 and second engaging component 16, when positioned about a stomach, would occupy the anterior and posterior wall of the stomach. When the first engaging component 12 and the second engaging component 16 are located in the desired position, the user/operator may then approximate the plates to each other gradually (millimetrically) using apparatus 1500 device without producing any ischemic or tissue damage. When the user/operator has positioned restraining device 10, apparatus 1500 would then be separated from restraining device and pulled out of the abdominal cavity through the port. If desired, restraining device may also be secured in the gastric tissue with superficial stitches.

Figure 17A:
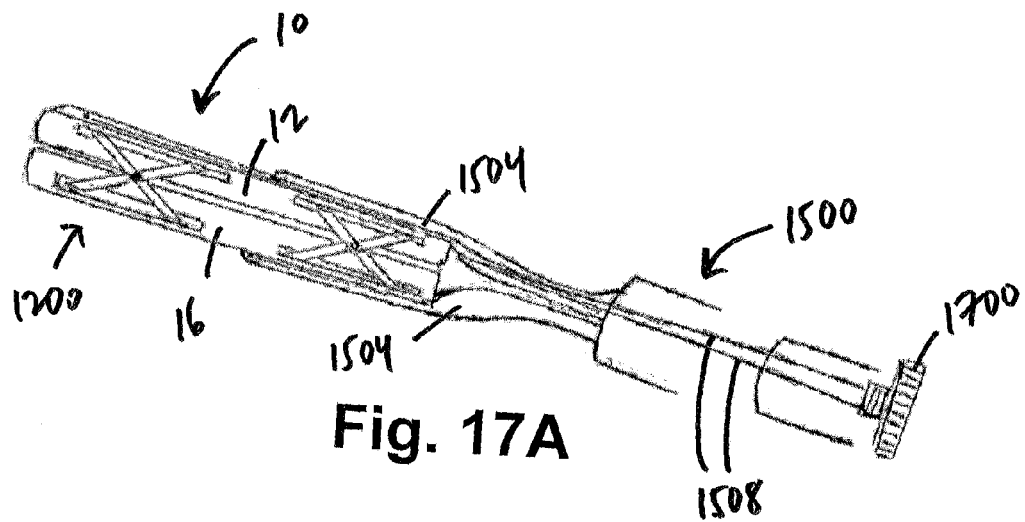
FIGS. 17A and 17B show additional exemplary embodiments of an apparatus for delivering a restraining device according to the present disclosure.
Figure 17B:
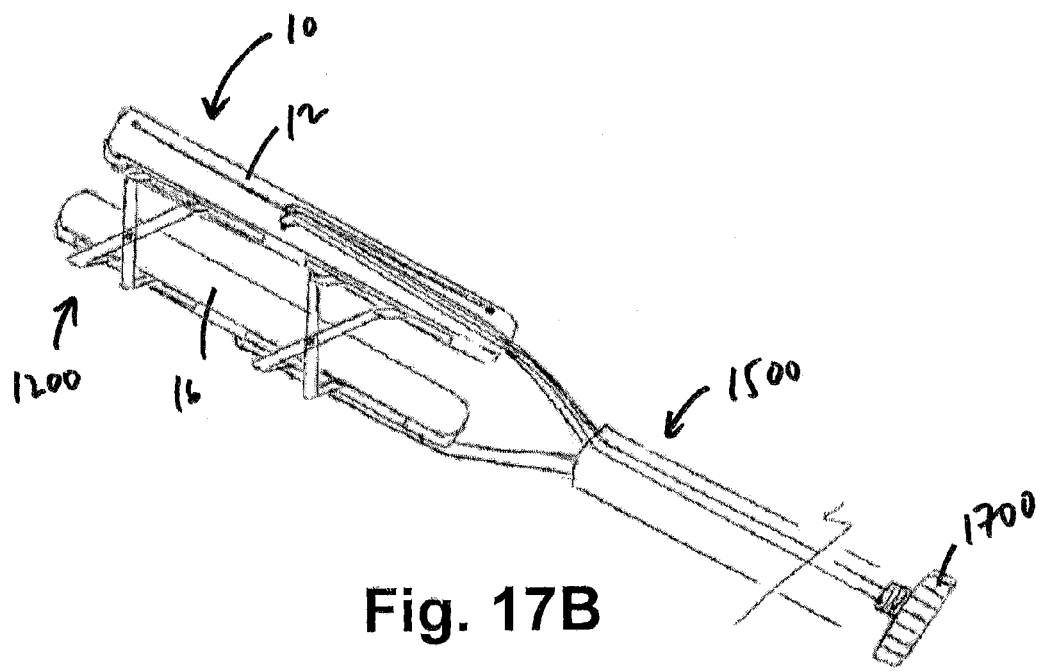

FIGS. 17A and 17B show another exemplary embodiment of an apparatus 1500 engaging/positioning an exemplary restraining device 10 of the disclosure of the present application. As shown in FIGS. 17A and 17B, arms 1504 of apparatus 1500 may engage the first engaging component 12 and the second engaging component 16 of restraining device 10, whereby the use of string 1508 connected to the first engaging component 12 and the second engaging component 16 may be used by an operator of apparatus 1500 to "open" and/or "close" said components. One or more strings 1508, in such exemplary embodiments, may be coupled at their first ends to the first engaging component 12 and/or the second engaging component 16, and may be coupled at their second ends to a string rotator 1700 (another exemplary "puller" of the present disclosure) as shown in FIGS. 17A and 17B. Operation/rotation of string rotator 1700 may then facilitate the "opening" of restraining device 10 from a "closed" configuration (as shown in FIG. 17A) to an "open" configuration (as shown in FIG. 17B). In such an embodiment, arms 1504 may also be positioned upon the first engaging component 12 and/or the second engaging component 16 at or near the center of said components (forming a "pivot" area), and the string rotator 1700 and strings 1504 affixed thereto may operate to keep said components in their axial position. Ultimate restraining device 10 delivery may be performed using one or more methods described herein.

Figure 18:
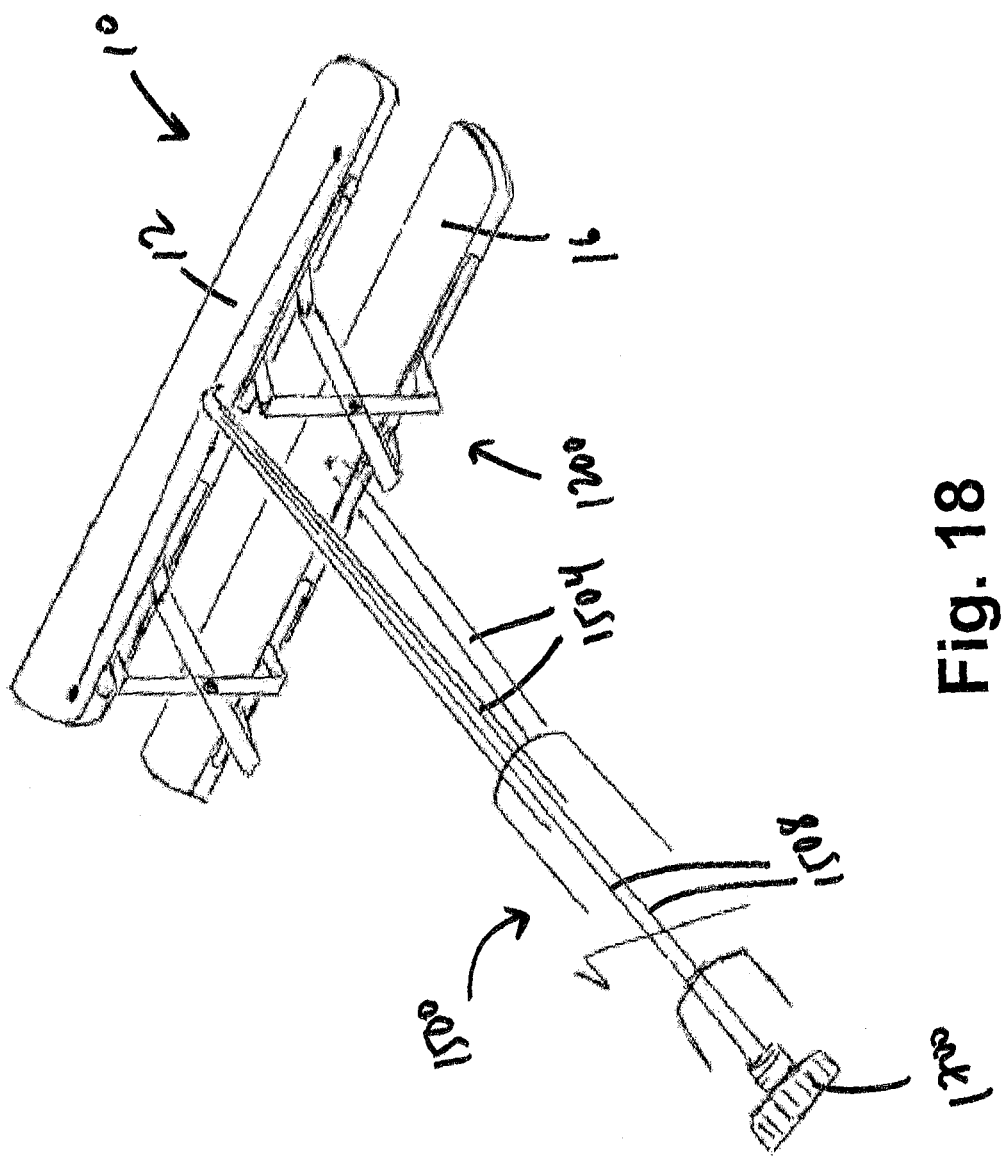
FIG. 18 shows an exemplary embodiment of an apparatus perpendicularly engaging a restraining device according to the present disclosure.

Restraining device 10 may also be positioned "perpendicularly" using apparatus 1500 as shown in FIG. 18. As shown in FIG. 18, arms 1504 and strings 1508 are shown positioned about the first engaging component 12 and the second engaging component 16 "perpendicularly" so that restraining device 10 and apparatus 1500 are not aligned with one another. Rotation of string rotator 1700, as described above, may facilitate the opening and/or closing of restraining device 10.

The various embodiments of restraining devices 10 of the present disclosure may be introduced into a body cavity through, for example, a laparoscopic port. Such restraining devices 10 would be inserted while "compressed" (as shown in FIGS. 1, 7A, 10, 11, 12A, and 14A, for example), and when inserted, would be "opened" or "deployed" (as shown in FIGS. 2, 7B, 8, 9, 13A, 13B, and 14B, for example) prior to being positioned about a stomach 100. In addition, a user of such a restraining device 10 may adjust the opening/deployed dimensions of restraining device 10 prior to positioning it about a stomach, and may further tailor the open/deployed dimensions of restraining device 10 after it has been positioned as desired.

Furthermore, any number of exemplary embodiments of restraining devices 10 of the present application may be wholly or partially resorbable by the body. For example, and using the exemplary restraining device 10 shown in FIGS. 1 and 2 as an example, first and second engaging components 12, 16 may not be resorbable by the body, while springs 22 may be resorbable. In such an embodiment, restraining device 10, once positioned about a stomach 100, may slowly begin the process of total or partial resorption. Resorbable materials suitable for one or more portions of restraining devices 10 may include, but are not limited to, polyglycolide (PGA), polylactide (PLA), 1-lactide (LPLA), poly(dl-lactide) (DL-PLA), poly(ε-caprolactone) (PCL), poly(dioxanone) (PDO), polylglycolide-trimethylene carbonate (PGA-TMC), poly(d,l-lactide-co-glycolide) (DLPLG), or combinations thereof.

In a situation where it is desired to have restraining device 10 serve as a reversible bariatric device, and if it is desired not to engage in a subsequent procedure to, for example, laparoscopically remove some or all of restraining device 10 from a body, some or all of restraining device 10 may be resorbed. By way of example, an exemplary restraining device comprising resorbable springs 22 may be positioned about a stomach, and first and second engaging components 12, 16 may slowly become coated with various fibrotic tissue. As springs 22 resorb, springs 22 will eventually no longer operate to connect first and second engaging components 12, 16 to one another, which will effectively cause the various portions of restraining device 10 to no longer serve as a restraining mechanism. Springs 22 may also become coated, in part or in their entirety, by fibrotic tissue, so that when springs 22 resorb, first and second engaging components 12, 16 remain positioned about stomach 100, but the introduction of food into a stomach 100, for example, does not exert any pressure on springs 22 by way of first and second engaging components 12, 16 as first and second engaging components 12, 16 are no longer connected to one another by way of springs 22. Furthermore, first and second engaging components 12, 16 may be resorbable and springs 22 may not, so as first and second engaging components 12, 16 resorb within the body, springs 22 no longer serve to connect first and second engaging components 12, 16 to each other, and restraining device 10 no longer performs any restraining function. Additional embodiments of restraining devices 10 may be resorbable, including, but not limited to, struts 700 and mesh curtain 702.

Regarding removal of exemplary embodiments of restraining devices 10 of the present application, said restraining devices 10 may be removed in whole or in part, for example, by way of a laparoscopic procedure. Reversibility of restraining devices 10, as referenced in the present application, pertains to the ability to position a restraining device 10 about a tissue or organ, and at some time thereafter, have some or all of restraining device 10 resorb within a body or remove some or all of restraining device from the body so that restraining device 10 no longer functions to restrain a tissue or organ. For example, and referencing the exemplary embodiments shown in FIGS. 1 and 2, a laparoscopic procedure to remove springs 22 from the restraining device 10 and the body, but not to remove first and second engaging components 12, 16 from the body, would have the effect of "reversing" the procedure of placing said restraining device 10 about a tissue or organ. Similarly, and as shown in FIGS. 7A, 7B, and 8, removal of struts 700 from restraining device 10 would also have the effect of "reversing" the placement of restraining device 10 about a tissue or organ.

Figure 19:
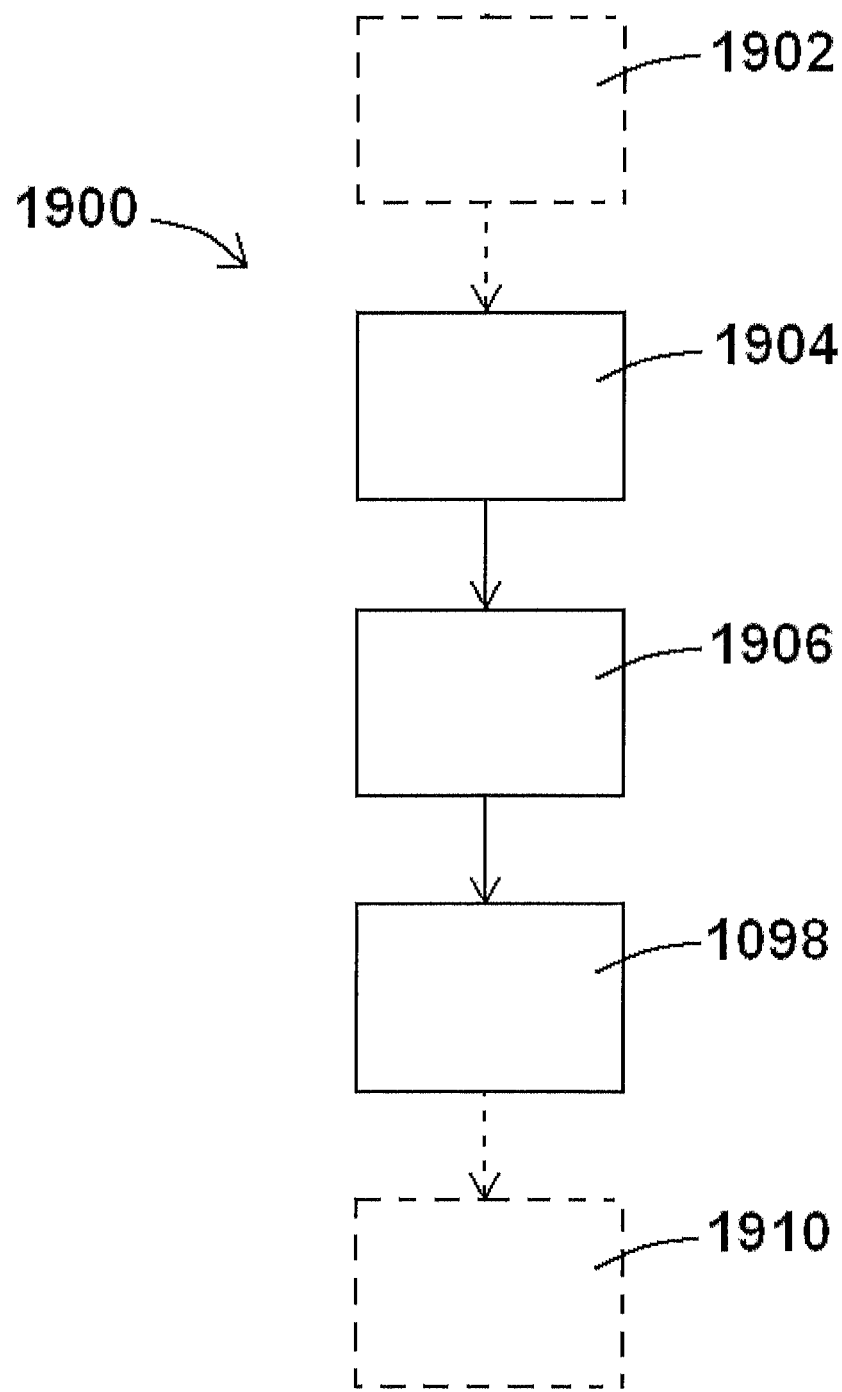
FIG. 19 shows a flow chart of a method for laparoscopically removing embodiments of the restraining device disclosed herein from a targeted tissue according to the present disclosure.

Furthermore, and if desired, the entirety of restraining device 10 may be removed laparoscopically by, for example, reversing the steps used to insert said restraining device 10 within a body. For example, a method 1900 for removing a restraining device 10 from a body as shown in FIG. 19 may comprise the steps of withdrawing restraining device 10 from a tissue or organ (withdrawal step 1904), configuring restraining device 10 to fit within a laparoscopic port (configuration step 1906), and removing restraining device 10 from the body through a laparoscopic port (removal step 1908). Such an exemplary method may be preceded by positioning a laparoscopic port within a body to facilitate removal of restraining device 10 (port insertion step 1902), and may be followed by removing said laparoscopic port from the body after removal step 1908 (port removal step 1910).

Figure 20:
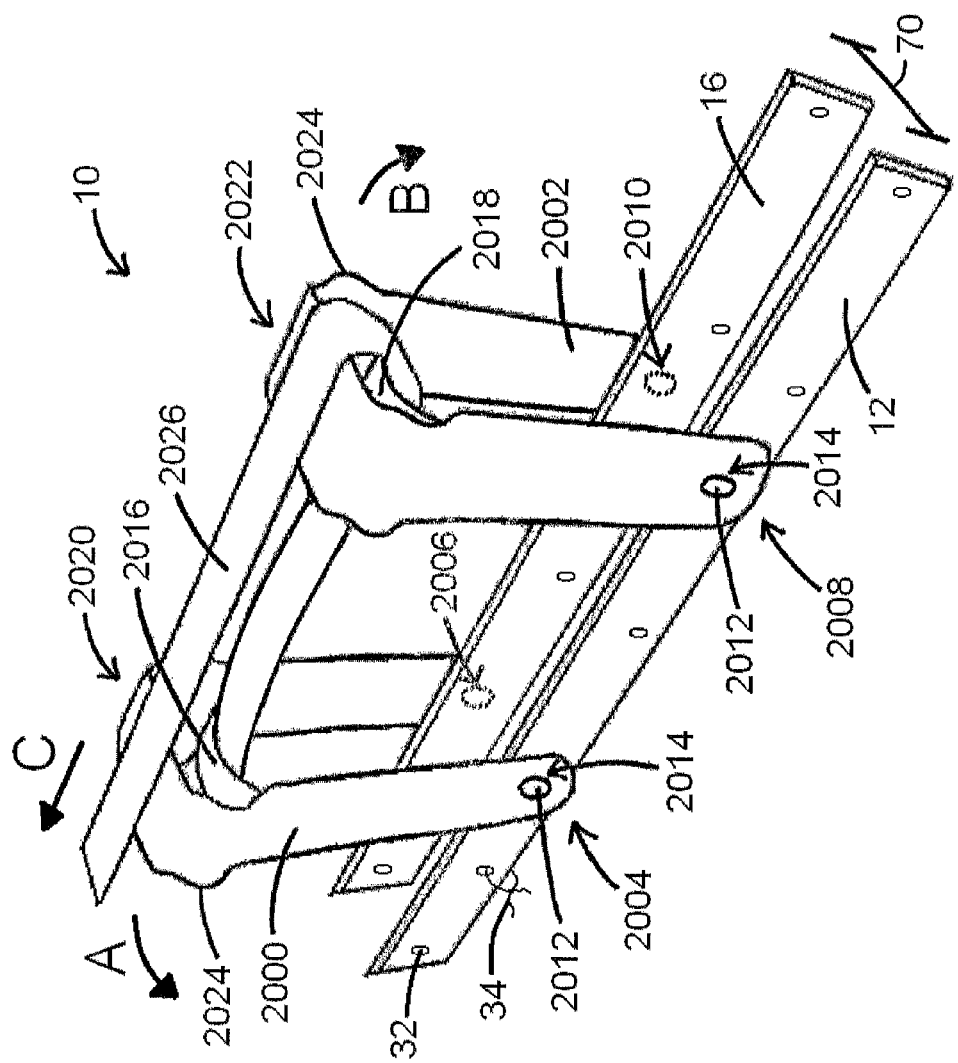
FIG. 20 shows a perspective view of at least another embodiment of a restraining device for restoring and/or supporting a tissue or organ of the present disclosure.
Figure 23:
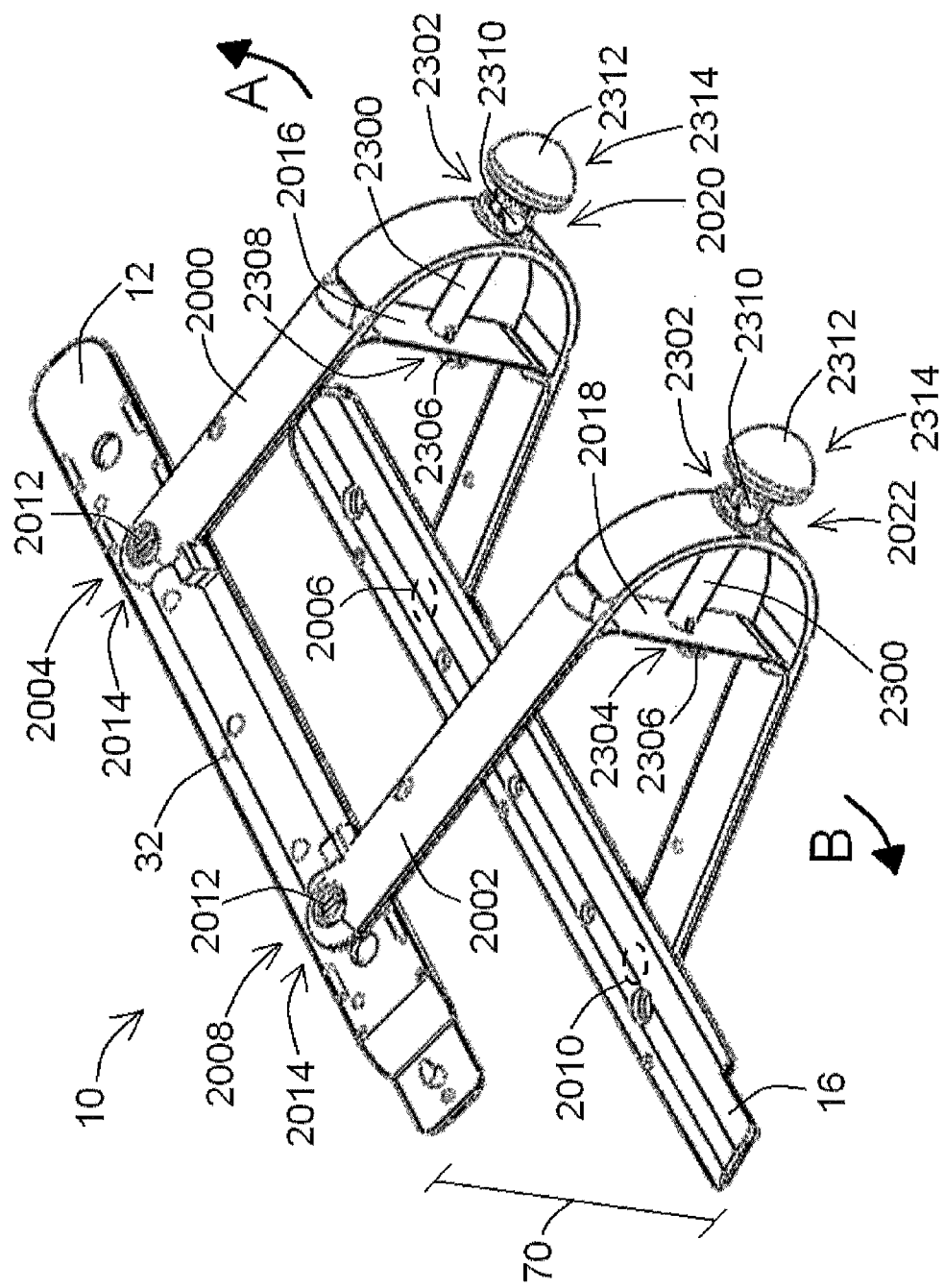
FIG. 23 shows a perspective view of at least another embodiment of a restraining device for restoring and/or supporting a tissue or organ of the present disclosure.

Additional embodiments of restraining devices 10 of the present disclosure are shown in FIGS. 20 and 23. As shown in the embodiments shown in FIGS. 20 and 23, restraining devices 10 comprise a first engaging component 12 and a second engaging component 16, such as those provided in various other embodiments herein. First engaging component 12 and second engaging component 16, in such an exemplary embodiment, are positioned relatively parallel to one another. A first swivel arm 2000 and a second swivel arm 2002 are pivotally connected to first engaging component 12 and second engaging component 16, so that first swivel arm 2000 engages first engaging component 12 at pivot point 2004 and engages second engaging component 16 at pivot point 2006, and so that second swivel arm 2002 engages first engaging component 12 at pivot point 2008 and engages second engaging component 16 at pivot point 2010. First swivel arm 2000 and second swivel arm 2002 may swivel in the directions shown in arrows A and B in FIGS. 20 and 23, noting that first swivel arm 2000 and second swivel arm 2002 may move in opposite directions, so that one moves in the direction of arrow A and the other moves in the direction of arrow B, or first swivel arm 2000 and second swivel arm 2002 may move in the same direction.

First engaging component 12 and/or second engaging component 16 may present studs 2012, as shown in FIGS. 20 and 23, whereby studs 2012 permit first swivel arm 2000 and/or second swivel arm 2002 to be engaged thereto and permit swiveling/rotation about the various pivot points. In at least one embodiment, studs 2012 have a bulbous component relatively larger than a non-bulbous portion, so that a first swivel arm 2000 and/or a second swivel arm 2002 presenting one or more apertures 2014 therethrough may engage studs 2012. Any number of other means to couple first swivel arm 2000 and/or second swivel arm 2002 to first engaging component 12 and/or second engaging component 16 may be used, such as pins, rivets, snaps, screws, and/or other fasteners or coupling means.

First swivel arm 2000 and second swivel arm 2002, as shown in FIGS. 20 and 23, may further comprise a first interconnection arm 2016 and a second interconnection arm 2018 positioned relative to bends 2020, 2022 of said arms. Bends 2020, 2022, as shown in FIGS. 20 and 23, are positioned in the relative middle (somewhere between the relative ends) of first swivel arm 2000 and a second swivel arm 2002, so that first swivel arm 2000 and second swivel arm 2002 form a relative "U-shape" within restraining device 10. First swivel arm 2000 and/or a second swivel arm 2002 may further comprise various additional curvatures 2024, such as shown in FIG. 20, such that bends 2020, 2022 and/or curvatures 2024 define a native U-shaped configuration as previously described.

An interior space 70 between the first engaging component 12 and the second engaging components 16, as shown in FIGS. 20 and 23, may change depending on various factors and/or configurations of restraining device 10. For example, and during insertion of an embodiment of a restraining device 10 such as shown in FIG. 20 or 23 through a laparoscopic port, first swivel arm 2000 and a second swivel arm 2002 may be relatively parallel to, or in the same relative plane as, first engaging component 12 and second engaging component 16, so that the interior space 70 is relatively small. After insertion, and after swiveling first swivel arm 2000 and a second swivel arm 2002 about first engaging component 12 and second engaging components 16, the interior space 70 may either stay the same or increase to facilitate placement of restraining device 10 about a stomach, for example. Furthermore, the use of a tape 2026 positioned about one or more of the first swivel arm 2000 and the second swivel arm 2002, as shown in FIG. 20, may further adjust the amount of interior space 70 between the first engaging component 12 and the second engaging components 16 depending on the amount of relative tension (pull) is applied to tape 2026. For example, if tape 2026 is positioned about one or more of the first swivel arm 2000, and the second swivel arm 2002 so that pulling tape 2026 in a direction shown by arrow C in FIG. 20 causes portions of tape 2026 to press against first interconnection arm 2016 and/or second interconnection arm 2018 causing the relative ends of each of first swivel arm 2000 and a second swivel arm 2002 to move toward each other, the amount of interior space 70 between first engaging component 12 and second engaging component 16 may be reduced. In such an embodiment, restraining device 10 could be inserted into a mammalian body, positioned around a bodily organ without applying pressure to said organ, and tape 2026 could be pulled so that the amount of interior space 70 is adjusted as desired for the particular application. In a bariatric application, for example, it is desired not to have portions of restrictive device 10 apply any pressure about the stomach, but tape 2026 could be pulled/adjusted so first engaging component 12 and second engaging component 16 properly engage the stomach and be sutured thereto as desired. Distention of the stomach, such as by the introduction of solid and/or liquid food or water into the stomach, would cause the stomach to exert a force/pressure against the first engaging component 12 and second engaging component 16, forming a first stomach portion 110 and a second stomach portion 112 as shown in FIGS. 4A and 4B referenced above and FIG. 21 referenced below.

In addition, and as shown in the exemplary embodiments of restraining devices 10 of the present disclosure shown in FIGS. 20 and 23, various portions of restraining device 10, such as the first engaging component 12, the second engaging component 16, the first swivel arm 2000, and/or the second swivel arm 2002 may have one or more suture apertures 32 defined therethrough to facilitate the placement of one or more sutures 34 (also referred to herein as strings 34) to couple restraining device 10 to a portion of a mammalian body, such as a stomach. In various embodiments, one or more of the relative ends of the first engaging component 12 and the second engaging component 16 may be rounded and/or tapered to improve overall patient comfort when a restraining device is positioned within the patient's body.

Figure 21:
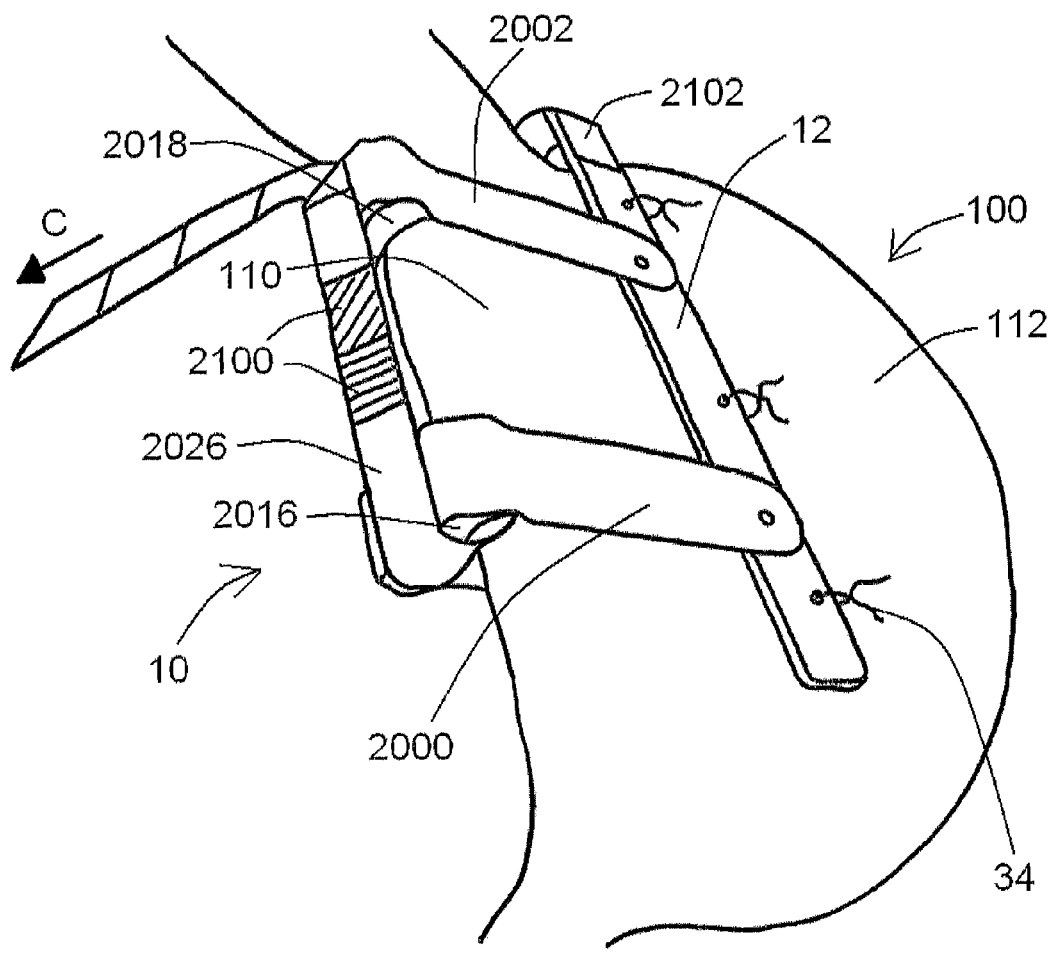
FIG. 21 shows an exemplary embodiment of a restraining device positioned about a stomach according to the present disclosure.

FIG. 21 shows an exemplary embodiment of a restraining device 10, such as shown in FIG. 20, positioned about a stomach. As shown in FIG. 21, device 10 may be positioned about stomach 100 similar to placement of restraining device 10 about stomach 100 as shown in FIG. 5B, so that the first engaging component 12 and the second engaging component 16 (not shown in FIG. 21) may engage opposite sides of stomach 100. Restraining device 10 may be secured to stomach 100 using one or more sutures 34 to couple restraining device 10 to stomach 100, and restraining device 100 may be further positioned about stomach 100 by way of adjusting tape 2026 positioned around restraining device 10. As shown in FIG. 21, tape 2026 is positioned about restraining device 10 so to engage first interconnection arm 2016 and second interconnection arm 2018, whereby pulling tape 2026 in a direction shown by arrow C would cause first engaging component 12 and second engaging component 16 to move closer to one another. Tape 2026 may have one or more detectable portions 2100 positioned/imprinted thereon, so that a user of restraining device 10 can "see" the adjustment of tape 2026 by way of fluoroscopy (if detectable portions 2100 are radioopaque), camera, or other means whereby portions of a device positioned within a body can be visualized, either directly or through some sort of technological means, to allow a user of such a device to adjust the same.

Furthermore, and as shown in FIG. 21, restraining device 10 may have a cover flap 2012 positioned thereon to assist maintaining the placement of restraining device 10 about stomach 100. Cover flap 2012, as shown in FIG. 21, may be ultimately coupled to first engaging component 12 and second engaging component 16 (not shown in FIG. 21), so that after restraining device 10 is positioned about a stomach 100, cover flap 2012 may be closed (initially secured to first engaging component 12 and closed by way of securing cover flap 2012 to second engaging component 16, or vice versa) about an upper portion of stomach 100.

As referenced above, restraining device 10 is positioned about stomach 100 so not to exert pressure upon stomach 100, but when stomach 100 becomes distended, stomach 100 exerts pressure/force upon first engaging component 12 and second engaging component 16 of restraining device 10.

Figure 22:
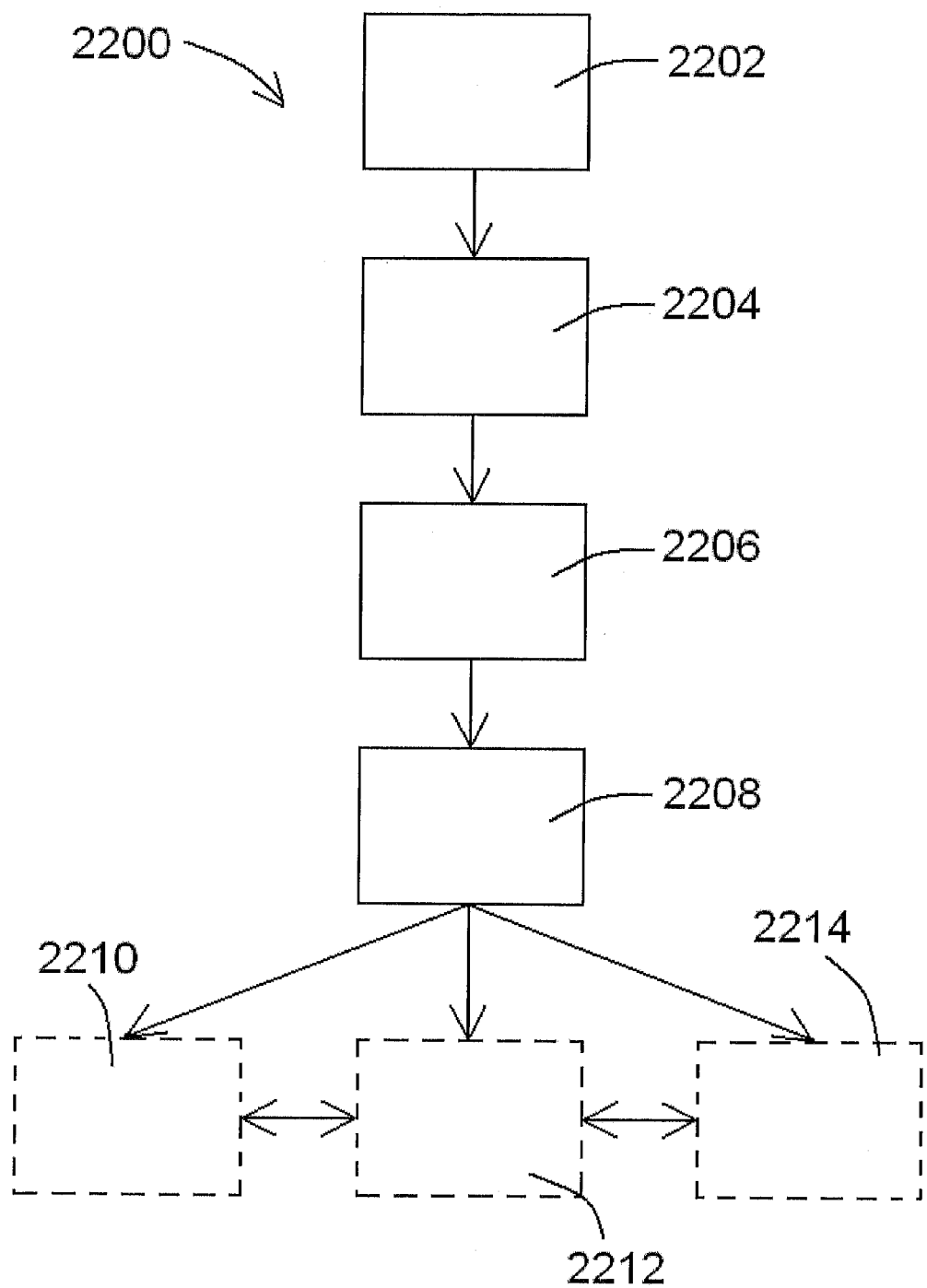
FIG. 22 shows steps of an exemplary method of inserting, delivering, and placing a restraining device about a targeted tissue according to the present disclosure.

Steps of a method for delivering and positioning an embodiment of a restraining device 10, such as the embodiment shown in FIGS. 20 and 21, are shown in FIG. 22. As shown in FIG. 22, exemplary method 2200 comprises the step of laparascopically inserting/advancing restraining device 10 into a patient's body (an exemplary insertion step 2202). In at least one embodiment, the restraining device 10 may be inserted through a 15 millimeter cannula under insufflation into the appropriate cavity of the patient's body. This may be achieved through use of an exemplary delivery device known in the art. At step 2202, first swivel arm 2000 and second swivel arm 2002 of restraining device 10 are swiveled/positioned in the substantially parallel position such that the overall diameter of the restraining device 10 is sufficiently narrow for insertion into the body.

At step 2204, restraining device 10 is advanced to a location adjacent to a targeted tissue, such as a stomach 100 (an exemplary advancement step 2204). At step 2206 (an exemplary swivel step), first swivel arm 2000 and second swivel arm 2002 of restraining device 10 are swiveled from a substantially parallel position to a substantially perpendicular position, separating the first and second engaging components 12, 16 from one another to a native interior space 70. Step 2206 may be performed using any number of standard laparoscopic tools known in the art useful to pull and grasp portions of a tissue or a device. In this manner, neither the proximal ends 13, 17 nor distal ends 14, 18 of the first and second engaging components 12, 16 of restraining device 10 are blocked by first swivel arm 2000 and second swivel arm 2002, and the first and second engaging components 12, 16 may be advanced over a targeted tissue, such as a stomach 100.

At step 2208, and under fluoroscopy, direct camera control or otherwise, restraining device 10 is positioned over the targeted tissue (an exemplary positioning step). In at least one embodiment, and at step 2206, the first side 12A of the first engaging component 12 is positioned adjacent to the desired surface of the targeted tissue and the first side 16A of the second engaging component 16 is positioned adjacent to an opposite side of the targeted tissue. As the first and second engaging components 12, 16 of the restraining device 10 are positioned adjacent to opposite sides of the targeted tissue, at this step 2208 the targeted tissue is positioned within the interior space 70 formed between the first and second engaging components 12, 16. Further, due to the configuration and composition of restraining device 10, restraining device 10 can remain within the patient's body for as long as the restoration or support treatment delivered thereby is desired.

After restraining device 10 is positioned about a targeted tissue (by way of performing positioning step 2208), method 2200 may further comprise the optional steps of securing one or more sutures to connect restraining device 10 to the targeted tissue (an exemplary suturing step 2210), and may further comprise the step of securing cover flap 2012 to further secure restraining device about the targeted tissue (an exemplary cover flap step 2212). In addition, and as shown in FIG. 22, method 2200 may further comprise the step of adjusting tape 2026 to control/adjust the interior space 70 between the first engaging component 12 and the second engaging component 16 whereby at least a portion of the targeted tissue is positioned therebetween (an exemplary tape adjustment step 2214).

In the exemplary embodiment of a restraining device 10, as shown in FIG. 23, restraining device 10 comprises one or more adjustment rods 2300 coupled to the first swivel arm 2000 and the second swivel arm 2002. In the embodiment shown in FIG. 23, for example, adjustment rods 2300 are coupled to first swivel arm 2000 and second swivel arm 2002 at or near bends 2020, 2022, and are further coupled to a first interconnection arm 2016 and a second interconnection arm 2018, respectively. As shown in FIG. 23, at in at least one embodiment, adjustment rods 2300 are coupled to first swivel arm 2000 and second swivel arm 2002 through swivel arm apertures 2302 defined therethrough, and are further coupled to first interconnection arm 2016 and second interconnection arm 2018 through interconnection arm apertures 2304 defined therethrough.

Figure 24:
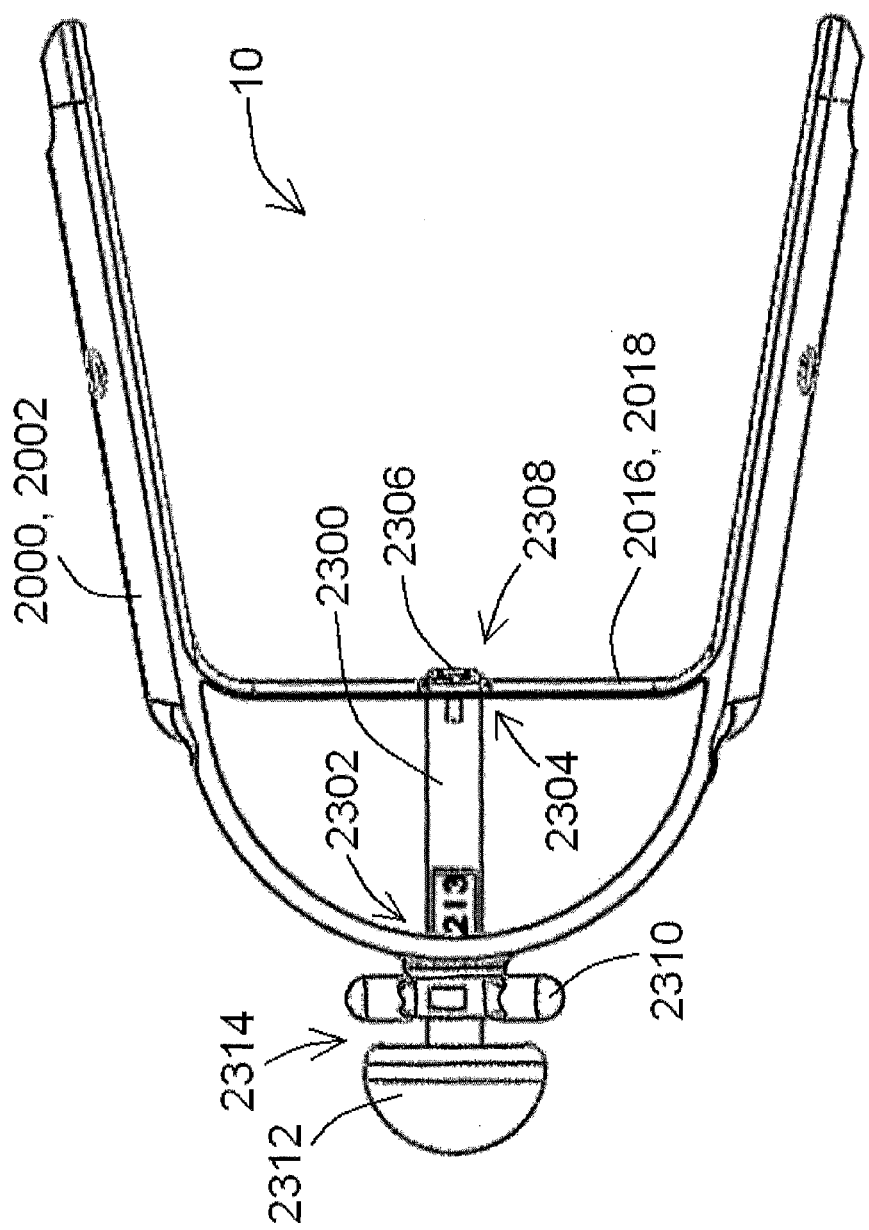
FIG. 24 shows a side view of the embodiment of a restraining device shown in FIG. 23.
Figure 25:
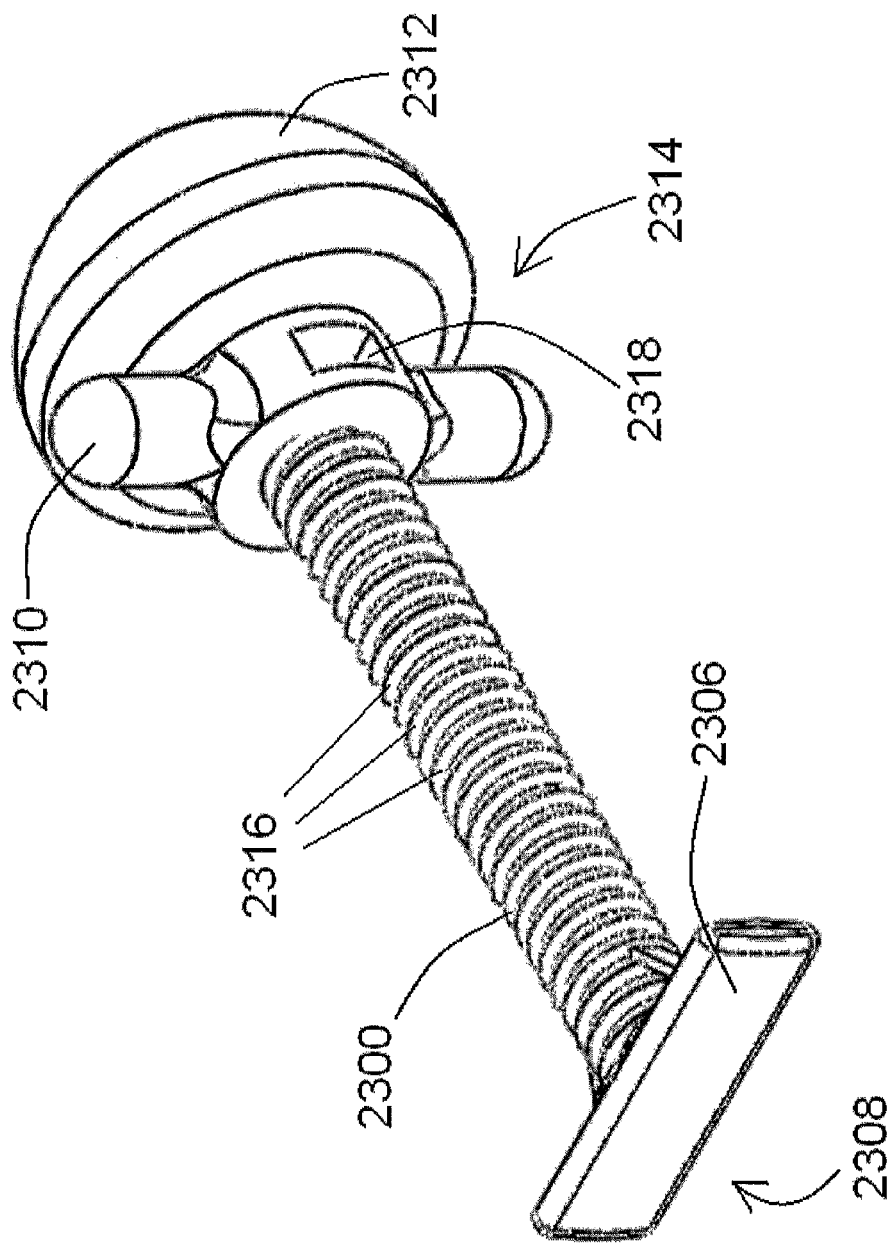
FIG. 25 shows a perspective view of an embodiment of an adjustment rod of the present disclosure.

Adjustment rods 2300, as shown in FIGS. 23 and 25, further comprise a bar 2306 coupled to adjustment rods 2300 at or near a distal end 2308 of adjustment rod 2300. Bar 2306, as shown in FIG. 24, is positioned distal to first interconnection arm 2016/second interconnection arm 2018, so that adjustment of a dial 2310 coupled to adjustment rod 2300 causes movement of first engaging component 12 and second engaging component 16 toward or away from one another. As shown in FIG. 24, first interconnection arm 2016 and second interconnection arm 2018, in various embodiments, may extend either completely or substantially along the length of first swivel arm 2000 and second swivel arm 2002 distal to first interconnection arm 2016 and second interconnection arm 2018, so that adjustment of dial 2310 facilitates movement of first swivel arm 2000 and second swivel arm 2002, thus facilitating movement of first engaging component 12 and second engaging component 16.

As shown in FIGS. 23-25, adjustment rod 2300 may further comprise a cap 2312 coupled thereto at or near a proximal end 2314 of adjustment rod 2300. Cap 2312, as shown in FIGS. 23-25, may prevent dial 2310 from disengaging adjustment rod 2300 so that when restraining device 10 is positioned within a body, dial 2310 remains upon restraining device 10. Cap 2312, in at least one embodiment, may be bulbous/rounded at one end for comfort when restraining device 10 is positioned within a body.

As shown in FIG. 24, dial 2310 may facilitate adjustment of device 10 by way of threads 2316 positioned along adjustment rod 2300. In such an embodiment, rotation of dial 2310 in a first direction would cause first engaging component 12 and second engaging component 16 to move toward one another, and rotation of dial 2310 in a second/opposite direction would cause first engaging component 12 and second engaging component 16 to move away from one another. As such, restraining device 10 may be positioned within a body about a stomach, for example, and be adjusted using dial 2310 so that restraining device 10 is optimally positioned about the stomach.

Figure 26:
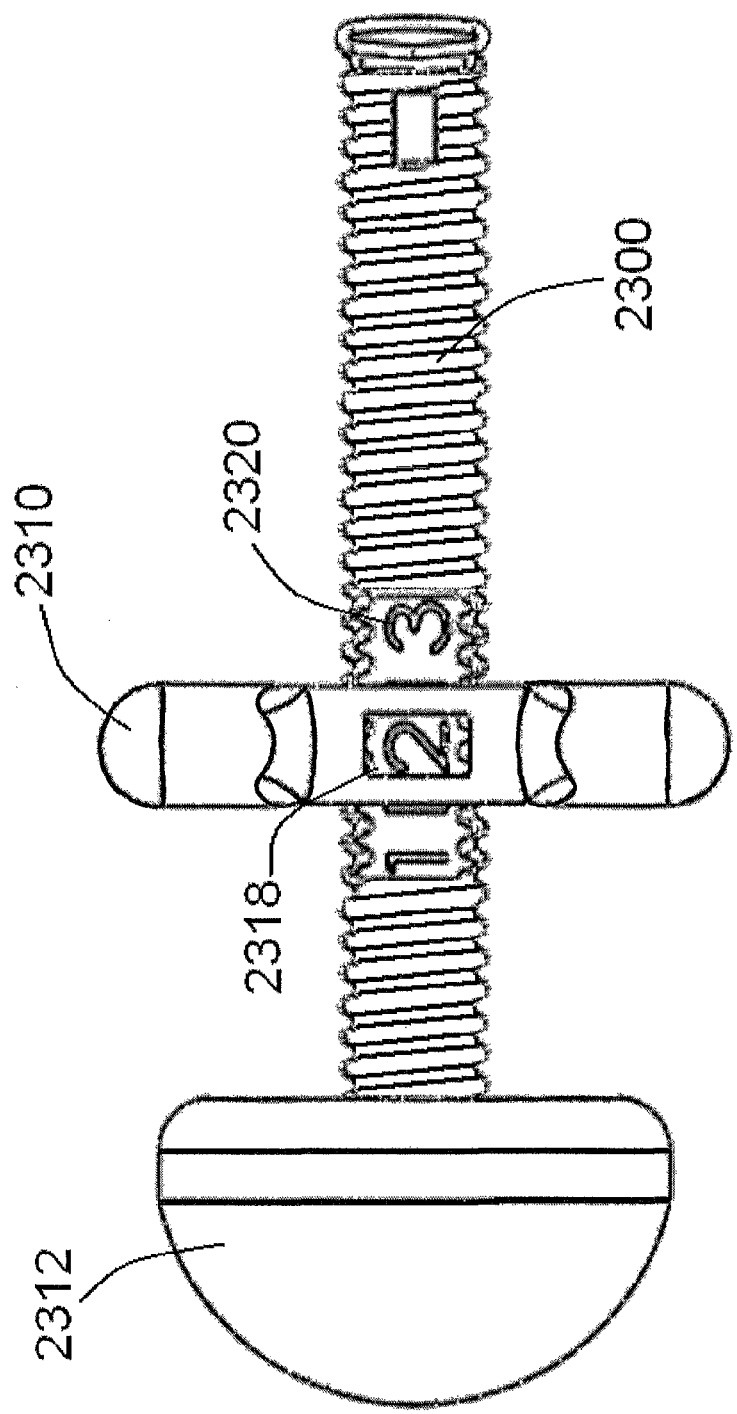
FIG. 26 shows a side view of the embodiment of an adjustment rod shown in FIG. 25.

As shown in the exemplary embodiments in FIGS. 25 and 26, dial 2310 may define a dial aperture 2318, whereby indicia 2320 upon adjustment rod 2300 may be viewed therethrough. As shown in FIG. 26, for example, as dial 2310 is rotated, one or more indicia 2320 may be visible through dial aperture 2318, so that a user of such an embodiment of a restraining device 10 of the present disclosure may identify a level of adjustment. Indicia 2320 may be one or more numbers, letters, lines and/or other indicia 2320 useful to identify a level of adjustment of restraining device 10.

Figure 27:
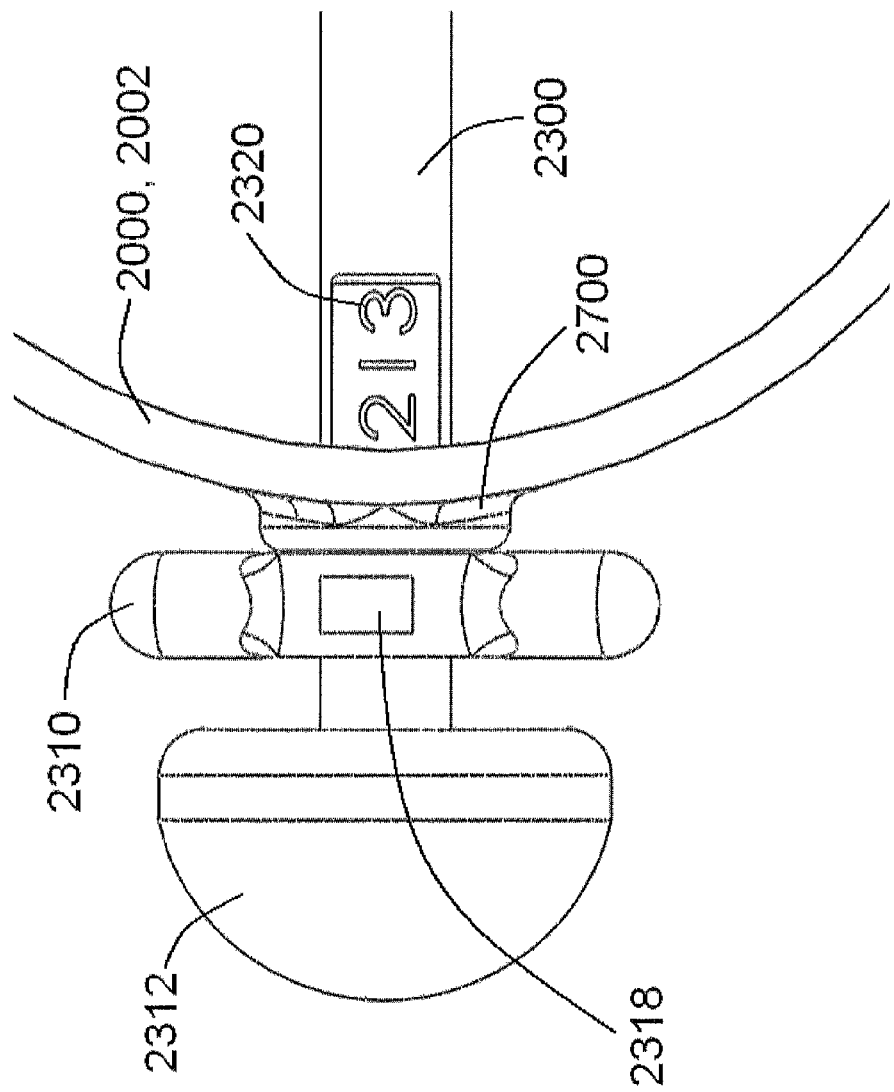
FIG. 27 shows a side view of an embodiment of an adjustment rod coupled to at least another component of an exemplary restraining device of the present disclosure.

As shown in FIG. 27, and in at least one embodiment of a restraining device 10 of the present disclosure, restraining device 10 further comprises at least one flange 2700 coupled to first swivel arm 2000 and/or second swivel arm 2002. Flange 2700 defines an aperture therethrough so that adjustment rod 2300 may fit therethrough, providing physical support for dial 2310 as dial 2310 engages said flange 2700.

Figure 28:
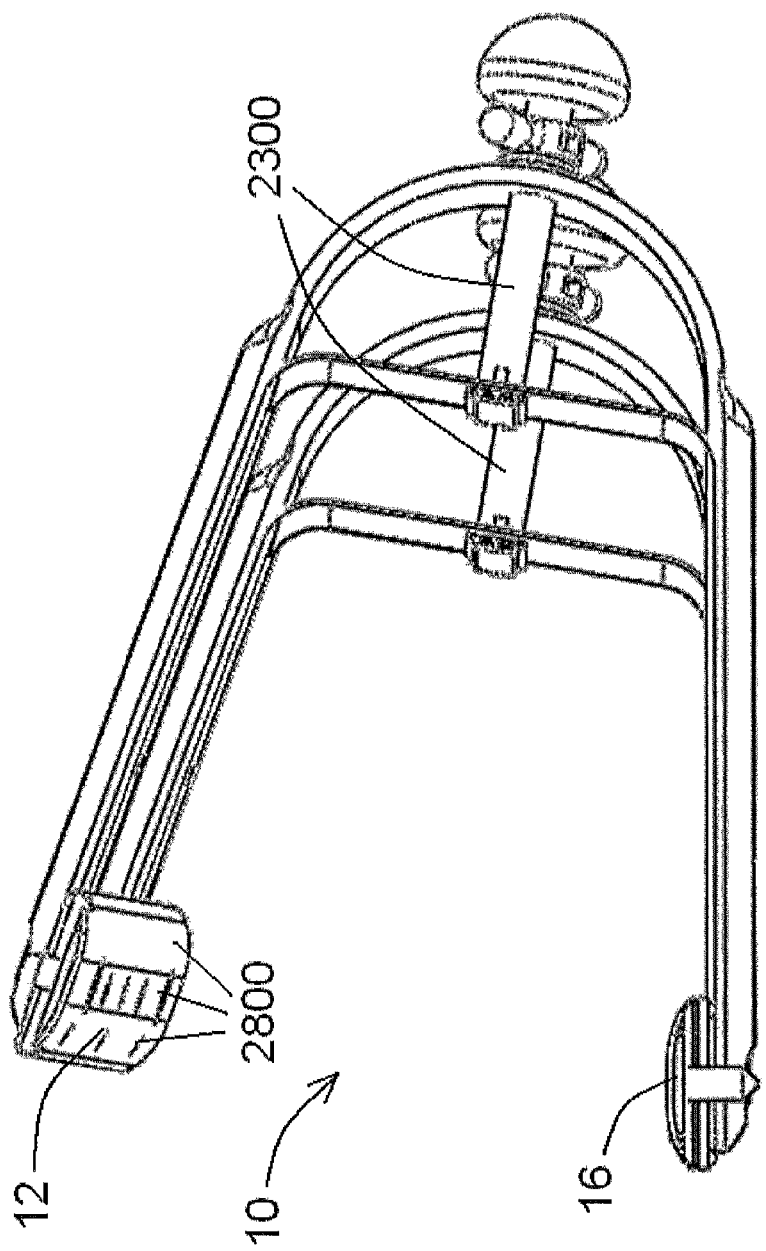
FIG. 28 shows another perspective view of the embodiment of a restraining device shown in FIG. 23.

An exemplary embodiment of a restraining device 10 of the present disclosure having adjustment rods 2300 is shown in FIG. 28. As shown in FIG. 28, first engaging component 12 and/or second engaging component 16 may define one or more facets 2800 along at least part of the length of said components 12, 16, whereby facets 2800 provide a generally arcuate profile as shown therein. Facets 2800 may further improve the overall comfort of restraining device 10 when it is positioned with a patient's body.

Figure 29:
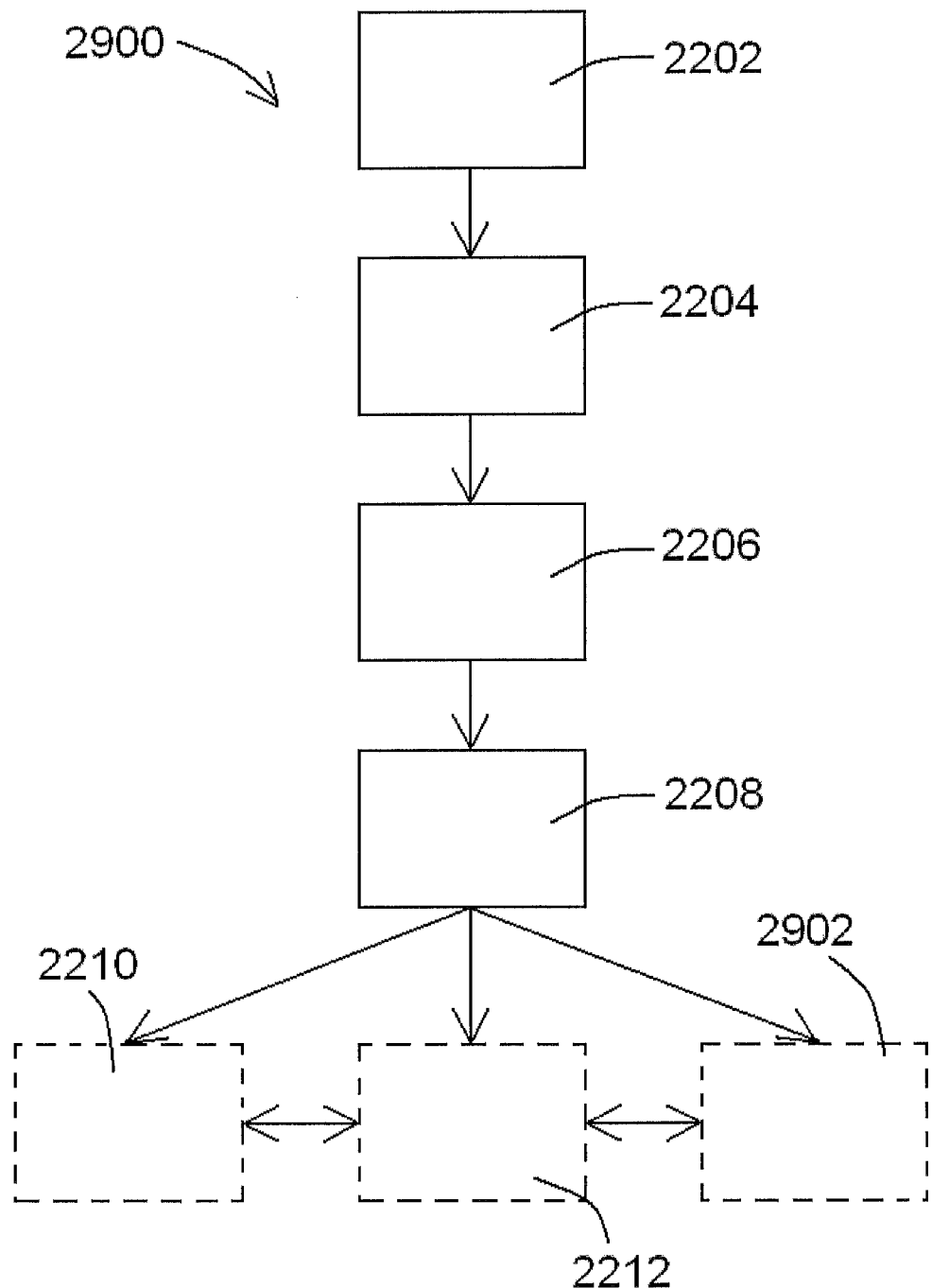
FIG. 29 shows steps of another exemplary method of inserting, delivering, and placing a restraining device about a targeted tissue according to the present disclosure.

Steps of a method for delivering and positioning an embodiment of a restraining device 10, such as the embodiment shown in FIG. 23, are shown in FIG. 29. As shown in FIG. 29, exemplary method 2900 comprises the step of laparoscopically inserting/advancing restraining device 10 into a patient's body (an exemplary insertion step 2202) as previously discussed herein. At step 2202, first swivel arm 2000 and second swivel arm 2002 of restraining device 10 are swiveled/positioned in the substantially parallel position such that the overall diameter of the restraining device 10 is sufficiently narrow for insertion into the body.

At step 2204, restraining device 10 is advanced to a location adjacent to a targeted tissue, such as a stomach 100 (an exemplary advancement step 2204). At step 2206 (an exemplary swivel step), first swivel arm 2000 and second swivel arm 2002 of restraining device 10 are swiveled from a substantially parallel position to a substantially perpendicular position, separating the first and second engaging components 12, 16 from one another to a native interior space 70 as previously discussed herein.

At step 2208, and under fluoroscopy, direct camera control or otherwise, restraining device 10 is positioned over the targeted tissue (an exemplary positioning step) as previously referenced herein. After restraining device 10 is positioned about a targeted tissue (by way of performing positioning step 2208), method 2900 may further comprise the optional steps of securing one or more sutures to connect restraining device 10 to the targeted tissue (an exemplary suturing step 2210), and regarding an embodiment of restraining device 10 of the present disclosure comprising a cover flap 2012, method 2900 may further comprise the step of securing cover flap 2012 to further secure restraining device about the targeted tissue (an exemplary cover flap step 2212). In addition, and as shown in FIG. 29, method 2900 may further comprise the optional step of rotating dial 2310 to control/adjust the interior space 70 between the first engaging component 12 and the second engaging component 16 whereby at least a portion of the targeted tissue is positioned therebetween (an exemplary dial adjustment step 2902).

Figure 30:
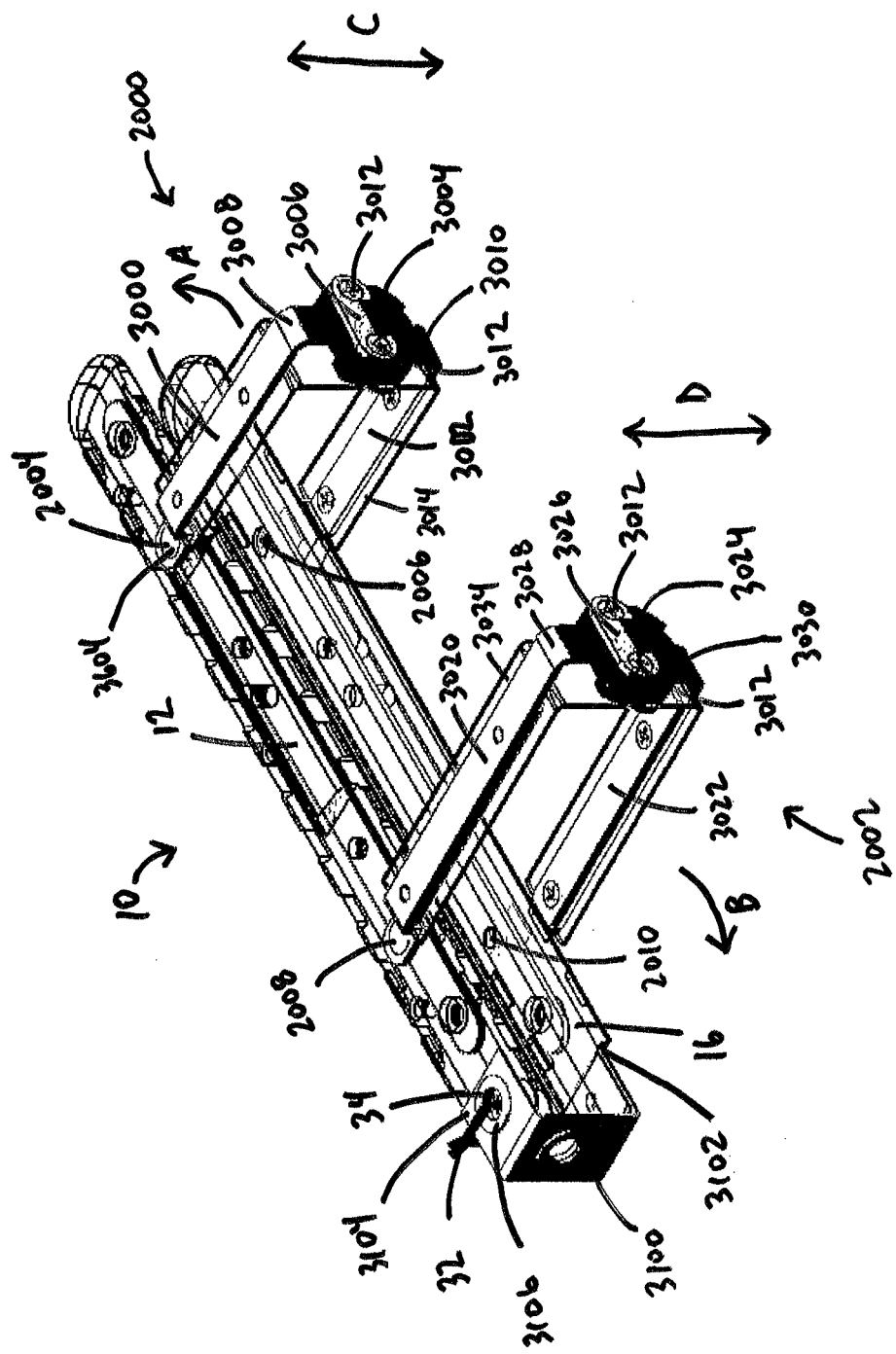
FIG. 30 shows a perspective view of an exemplary embodiment of a restraining device of the present disclosure in a relatively open configuration.
Figure 31:
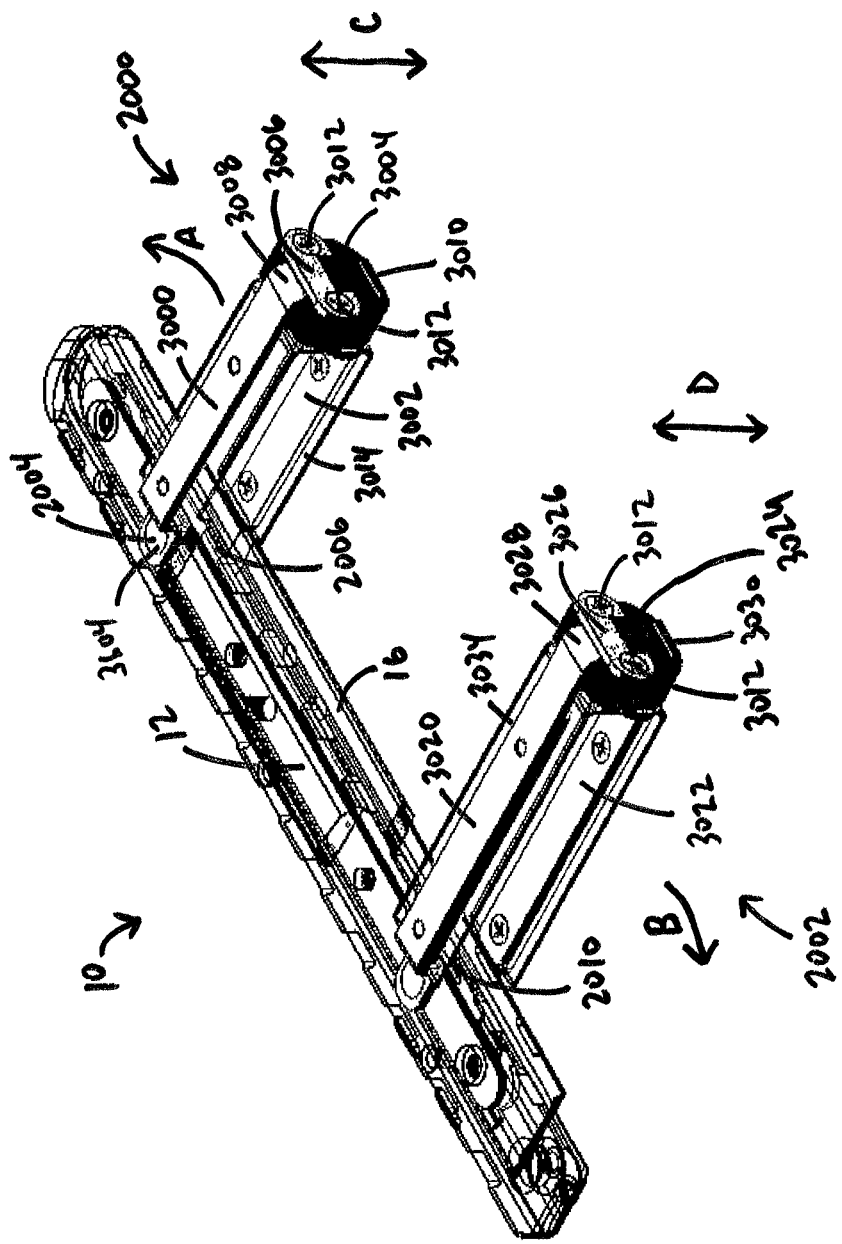
FIG. 31 shows a perspective view of an exemplary embodiment of a restraining device of the present disclosure in a relatively open configuration.

An additional embodiment of a restraining device 10 of the present disclosure is shown in FIGS. 30 and 31. As shown in FIGS. 30 and 31, restraining devices 10 each comprise a first engaging component 12 and a second engaging component 16, such as those provided in various other embodiments herein. First engaging component 12 and second engaging component 16, in such exemplary embodiments, are positioned relatively parallel to one another. A first swivel arm 2000 and a second swivel arm 2002 are pivotally connected to first engaging component 12 and second engaging component 16, so that first swivel arm 2000 engages first engaging component 12 at pivot point 2004 and engages second engaging component 16 at pivot point 2006, and so that second swivel arm 2002 engages first engaging component 12 at pivot point 2008 and engages second engaging component 16 at pivot point 2010. First swivel arm 2000 and second swivel arm 2002 may swivel in the directions shown in arrows A and B in FIGS. 30 and 31, noting that first swivel arm 2000 and second swivel arm 2002 may move in opposite directions, so that one moves in the direction of arrow A and the other moves in the direction of arrow B.

As shown in FIGS. 30 and 31, first swivel arm 2000 may comprise a first arm member 3000 and a second arm member 3002, and second swivel arm 2002 may comprise a first arm member 3020 and a second arm member 3022. First arm members 3000, 3020 and second arm members 3002, 3022 may each couple to a hub 3004, 3024 as shown in FIGS. 30 and 31. In at least one embodiment, and as shown in FIGS. 30 and 31, second arm members 3002, 3022 may be fixedly coupled to hubs 3004, 3024, and first arm members 3000, 3020 may slidingly engage said hubs 3004, 3024, whereby portions of first arm members 3000, 3020 are positioned between hubs 3004, 3024 and hub brackets 3006, 3026. First arm members 3000, 3020 may each have at least one bend 3008, 3028 therein, as shown in FIGS. 30 and 31, to facilitate said engagement of first arm members 3000, 3020 to hubs 3004, 3024. First arm members 3000, 3020, in at least one embodiment, are capable of movement relative to hubs 3004, 3024 in the directions shown in arrows C and D in FIGS. 30 and 31, whereby first arm members 3000, 3020 move in a first direction until they contact hubs 3004, 3024, for example, and move in a second direction until arm flanges 3010, 3030 of first arm members 3000, 3020 contact hub brackets 3006, 3026, for example. First arm members 3000, 3020 and second arm members 3002, 3022 may be referred to as "fixed arms" if they are fixed to one of hubs 3004, 3024, and may be referred to as "expandable arms" if they are coupled to hubs 3004, 3024 by way of hub brackets 3006, 3026 to facilitate movement relative thereto.

In at least one embodiment of an exemplary restraining device 10 of the present disclosure, and as shown in FIGS. 30 and 31, hub brackets 3006, 3026 may be coupled to hubs 3004, 3024 by way of one or more fasteners 3012, such as one or more screws, pins, rivets, and the like. Similarly, second arm members 3002, 3022 may be coupled to hubs 3004, 3024 by way of one or more fasteners 3012. In at least one embodiment, first arm members 3000, 3020 and/or second arm members 3002, 3022 are comprised of stainless steel (such as 316LVM, or implant-grade stainless steel) hubs 3004, 3024 are comprised of one or more polyaryletherketones (PEEKs), and hub brackets 3006, 3026 are also comprised of stainless steel. First engaging component 12 and second engaging component 16 may, in at least one embodiment, comprise stainless steel which may then be coated/overmolded with a biocompatible polymer, such as polyurethane (PX205, for example) or tecothane (TT-1075D-M, for example).

In various embodiments of restraining devices 10 of the present disclosure, restraining devices 10 may comprise one or more pads 3014, 3034 coupled to first arm members 3000, 3020 and/or second arm members 3002, 3022. Said pads 3014, 3034 may comprise any number of biocompatible polymers and/or other materials that are suitable for contacting an organ, such as a stomach, and which may provide some sort of cushioning effect. In at least one embodiment, pads 3014, 3034 may be comprised of a biocompatible polymer such as carbothane (such as PC-3595A), for example, and may be coupled to first arm members 3000, 3020 and/or second arm members 3002, 3022 using one or more fasteners 3012. In at least one embodiment, fasteners 3012, as referenced herein, may be comprised of stainless steel.

Regarding the exemplary embodiment of restraining device 10 shown in FIGS. 30 and 31, restraining device is shown in an open configuration in FIG. 30 and in a closed configuration in FIG. 31. As shown in FIG. 31, an exemplary restraining device 10 of the present disclosure may comprise a strap 3100 coupled thereto at first engaging component 12 and second engaging component 16. In at least one embodiment, strap 3100 is fixedly coupled to one or both of first engaging component 12 and second engaging component 16, and in another embodiment, strap is removably coupled to one or both of first engaging component 12 and second engaging component 16 by way of one or more sutures 32 (such as a 2-0 silk suture, for example), as shown in FIG. 31. As shown in the embodiment of restraining device 10 in FIG. 31, a first end 3102 of strap 3100 is fixedly coupled to second engaging component 16, and a second end 3104 of strap 3100 is removably coupled to first engaging component 12 by way of suture 32. In practice, suture 32 may not be positioned within suture aperture(s) 34 defined within one or more components of restraining device 10 until after restraining device 10 has been inserted into a mammalian body. In at least one embodiment, one or more suture apertures 34 defined within one or more components of restraining device 10 may comprise/define one or more eyelets 3106, whereby said eyelets 3106 provide additional reinforcement/strength, and may also provide a more smooth, rounded contour than suture apertures 34 so not to cause unintended wear, and potential breakage, of one or more sutures 32 positioned therethrough. In at least one embodiment, strap 3100 comprises carbothane (PC-3595A), and eyelets 3106 are comprised of nickel. In at least another embodiment, strap 3100, or portions thereof, may be radiopaque.

Figure 32:
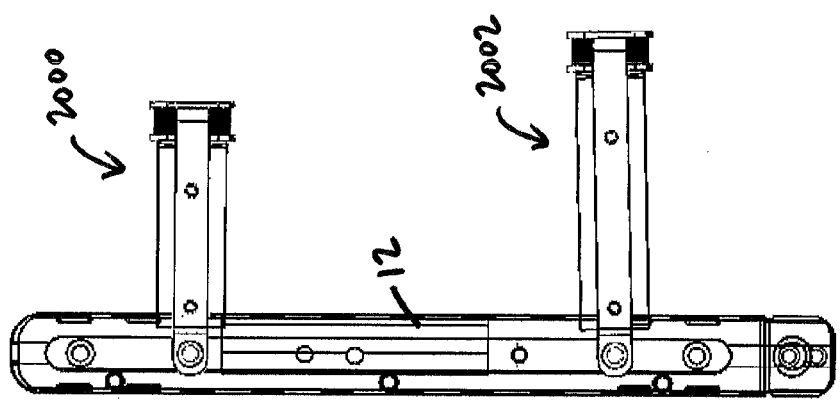
FIGS. 32 and 33 show top views of an exemplary embodiment of a restraining device of the present disclosure.
Figure 33:
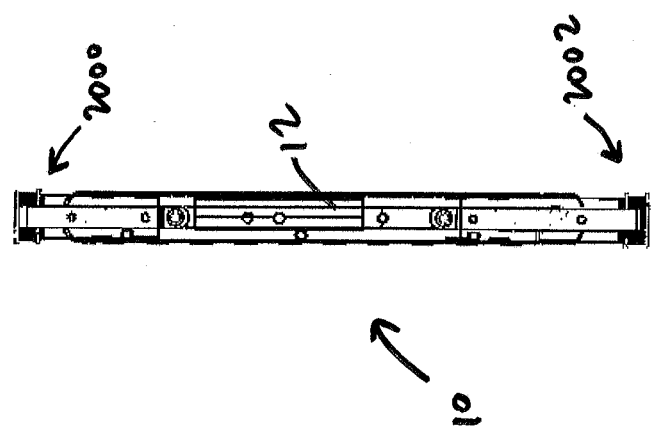
Figure 40:
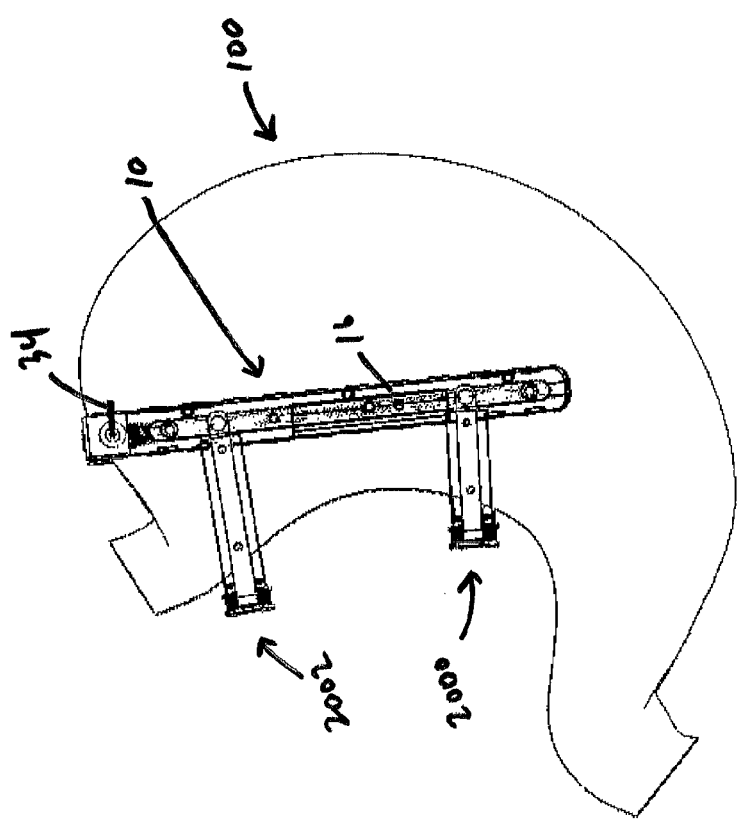
FIGS. 40, 41, and 42 show exemplary embodiments of restraining devices of the present disclosure positioned about a stomach.
Figure 41:
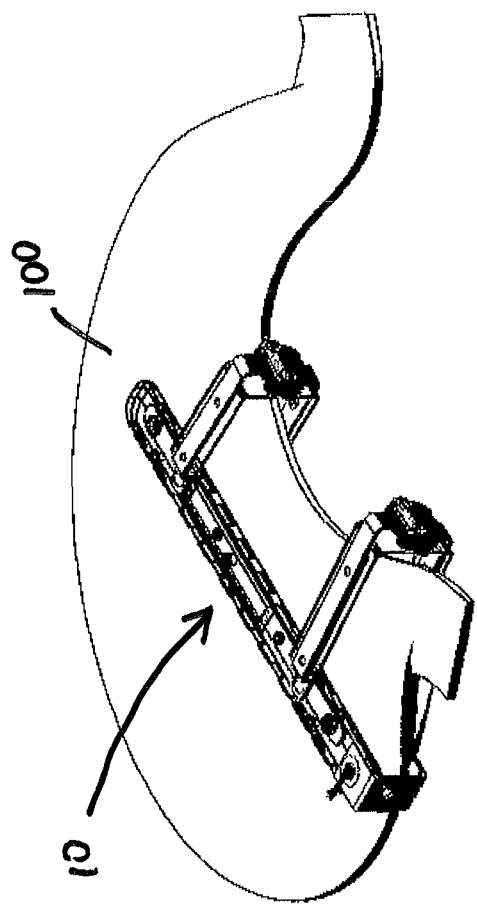
Figure 42:
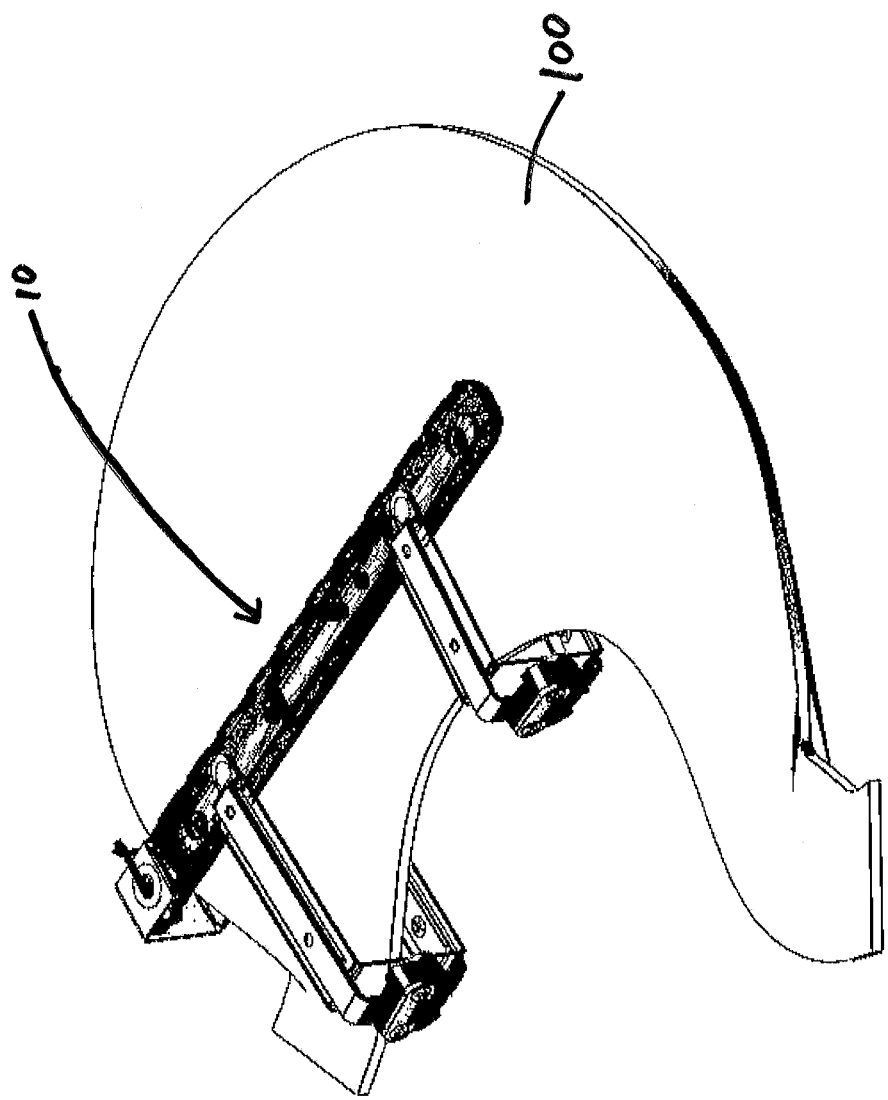

FIGS. 32 and 33 show top views of exemplary restraining devices 10 of the present disclosure. As shown in FIG. 32, restraining device 10 is shown with first swivel arm 2000 and second swivel arm 2002 in a positioned whereby said arms 2000, 2002 are at least substantially perpendicular to first engaging component 12. As shown in FIG. 32, and in at least one embodiment of a restraining device 10 of the present disclosure, first swivel arm 2000 is relatively shorter than second swivel arm 2002, whereby such a configuration allows for placement of restraining device 10 about a stomach, for example, as shown in FIGS. 40, 41, and 42.

Figure 34:
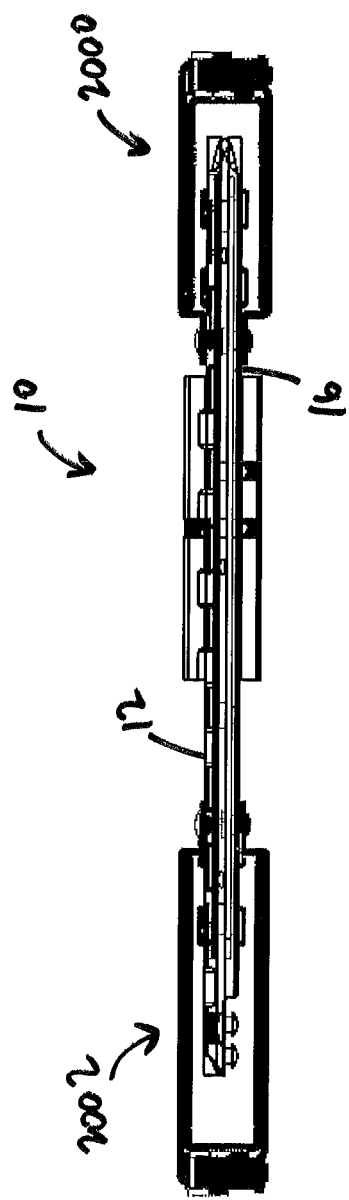
FIG. 34 shows a side view of an exemplary embodiment of a restraining device of the present disclosure in a relatively closed configuration.
Figure 35:
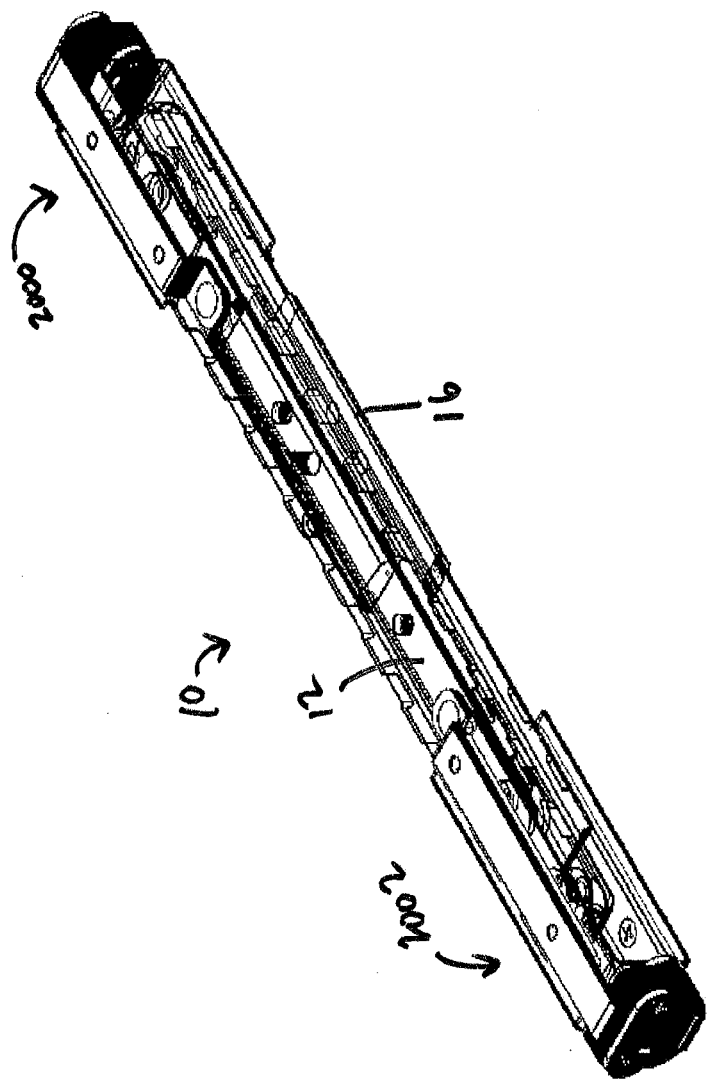
FIG. 35 shows a perspective view of an exemplary embodiment of a restraining device of the present disclosure in a relatively closed configuration.

FIG. 33 shows an exemplary restraining device 10 whereby first swivel arm 2000 and second swivel arm 2002 share a common linear axis with first engaging component 12. In the configuration shown in FIG. 33, for example, restraining device 10 may fit within a bodily laparoscopic port for eventual swiveling of arms 2000, 2002 and placement of restraining device 10 about an organ. FIG. 34 shows a front view of an exemplary restraining device 10 of the present disclosure in a similar configuration as shown in FIG. 33, and FIG. 35 shows a perspective view of restraining device 10 in the same configuration.

Figure 36:
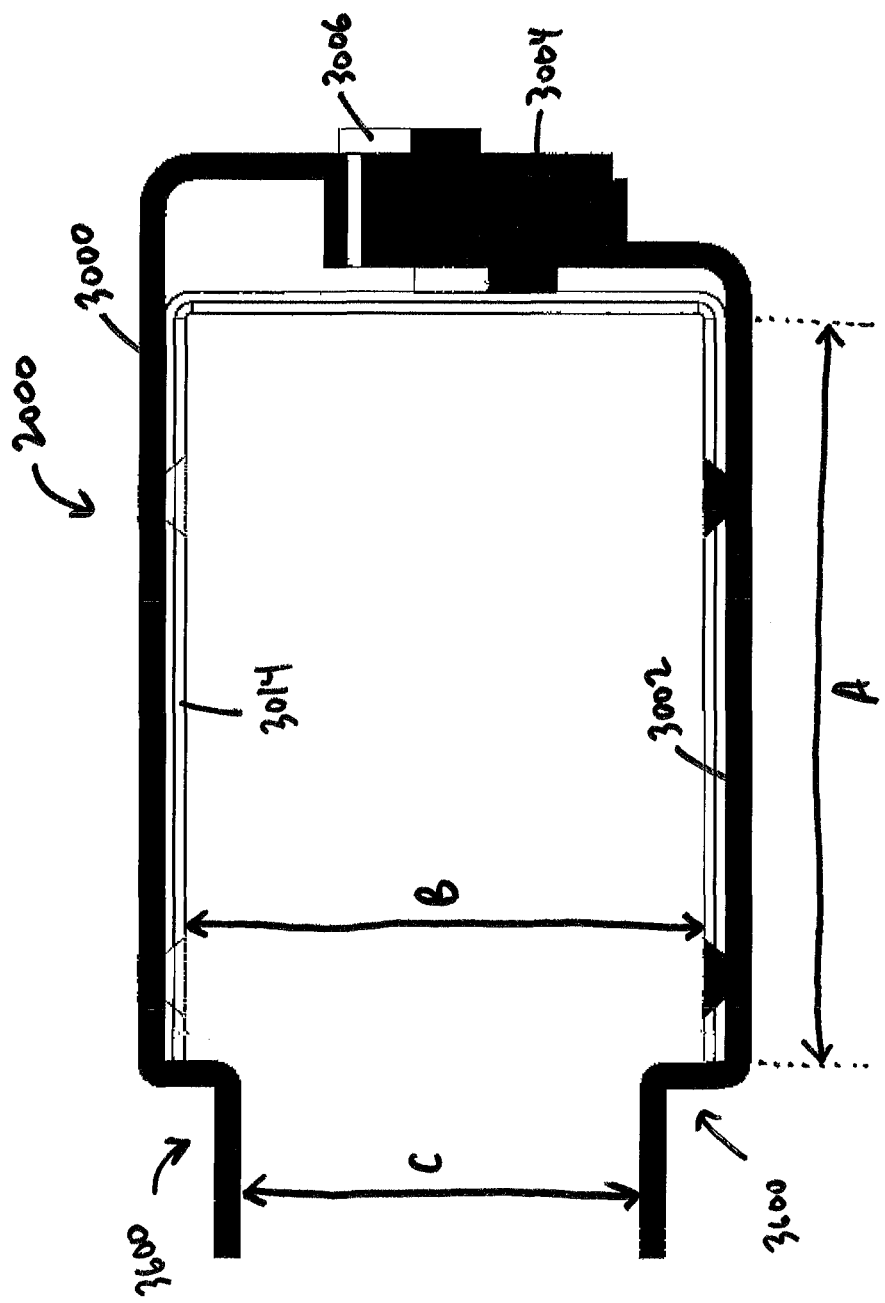
FIG. 36 shows a side view of an exemplary swivel arm of the present disclosure.
Figure 37:
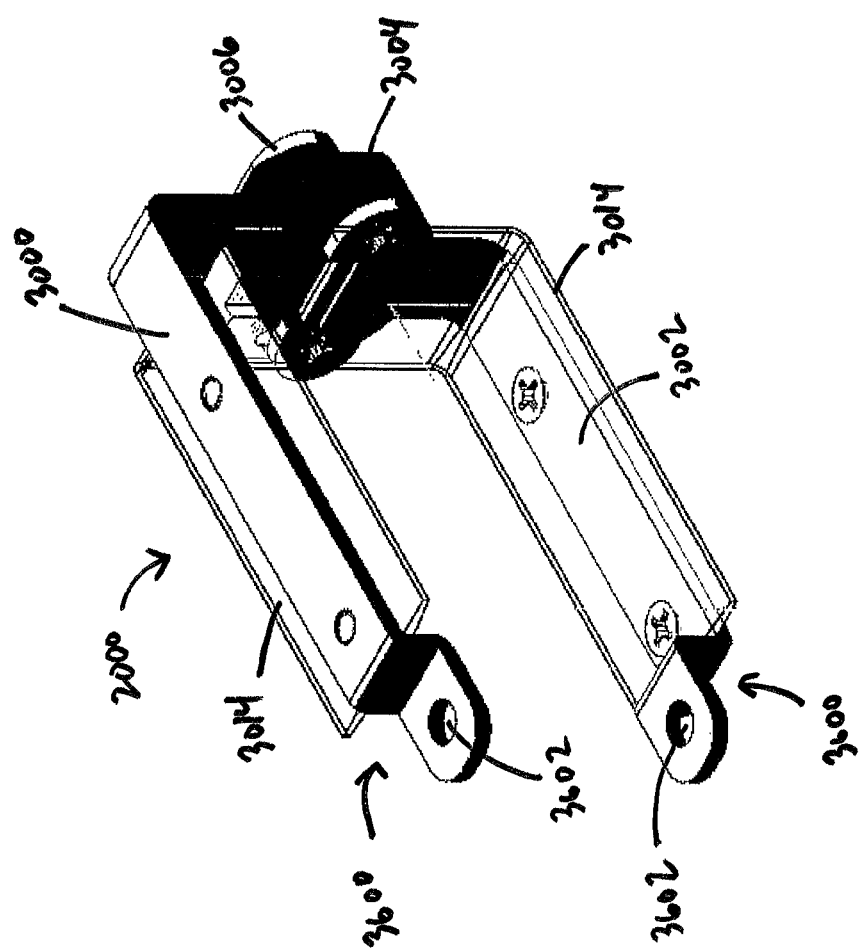
FIG. 37 shows a perspective view of an exemplary swivel arm of the present disclosure.

FIGS. 36 and 37 show a side view and a perspective view, respectively, of an exemplary first swivel arm 2000 of the present disclosure. In at least one embodiment, and as shown in FIG. 36, first swivel arm 2000 has an interior length (as indicated by arrow A in the figure) of about 26.5 mm, and has an expanded interior height (as indicated by arrow B in the figure) of about 19.1 mm. In other embodiments, the interior length and interior height may be greater or lesser than those shown in the figure.

As shown in FIGS. 36 and 37, an exemplary first swivel arm 2000 may have one or more distal arm flanges 3600, which, in at least one embodiment, are bent relatively down/up and then out, as shown in the figures, so that exemplary first swivel arm 2000 may engage first engaging component 12 and second engaging component 16 while maintaining integrity of first swivel arm 2000 and/or providing additional clearance for an organ positioned therebetween. In at least one embodiment, and as shown in FIG. 36, distal arm flanges 3600 result in an expanded flange height (as indicated by arrow C in the figure) of less than the expanded interior height. The relative distal ends of first swivel arm 2000, which may themselves comprise distal arm flanges 3600, may comprise one or more arm apertures 3602 configured to receive, for example, one or more rivets 3604 (as shown in FIGS. 30 and 31) therethrough to couple first swivel arm 2000 to a first engaging component 12 and a second engaging component 16. In at least one embodiment, rivets 3604 are comprised of stainless steel. In at least another embodiment, another type of fastener 3012, as described herein, aside from a rivet 3604 may be used.

Figure 38:
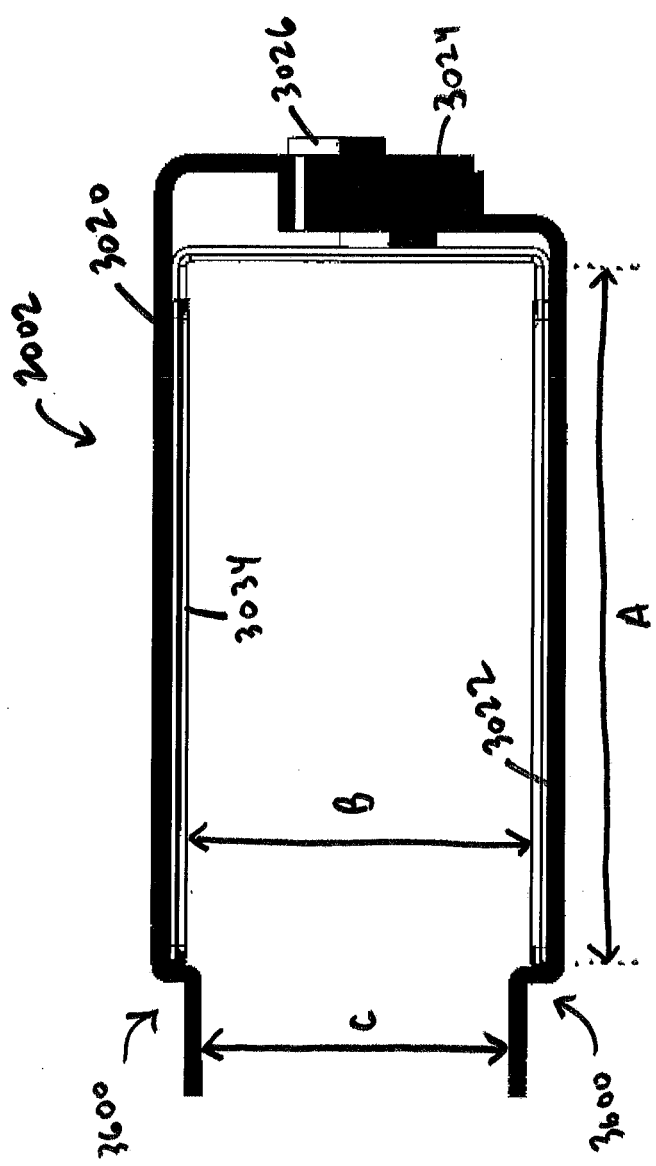
FIG. 38 shows a side view of another exemplary swivel arm of the present disclosure.
Figure 39:
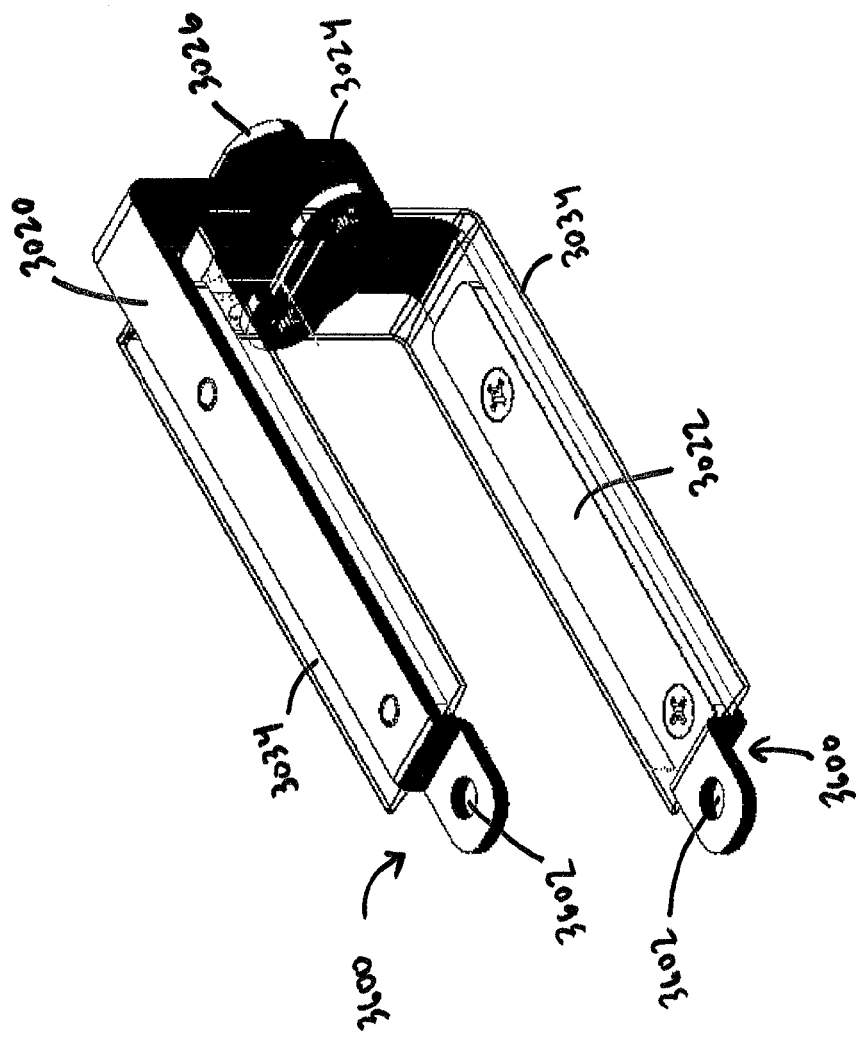
FIG. 39 shows a perspective view of another exemplary swivel arm of the present disclosure.

FIGS. 38 and 39 show a side view and a perspective view, respectively, of an exemplary second swivel arm 2002 of the present disclosure. In at least one embodiment, and as shown in FIG. 38, second swivel arm 2002 has an interior length (as indicated by arrow A in the figure) of about 37 mm, and has an expanded interior height (as indicated by arrow B in the figure) of about 18 mm. In other embodiments, the interior length and interior height may be greater or lesser than those shown in the figure.

As shown in FIGS. 38 and 39, an exemplary second swivel arm 2002 may also have one or more distal arm flanges 3600, which, in at least one embodiment, are bent relatively down/up and then out, as shown in the figures, so that exemplary second swivel arm 2002 may engage first engaging component 12 and second engaging component 16 while maintaining integrity of second swivel arm 2002 and/or providing additional clearance for an organ positioned therebetween. In at least one embodiment, and as shown in FIG. 38, distal arm flanges 3600 result in an expanded flange height (as indicated by arrow C in the figure) of less than the expanded interior height. The relative distal ends of second swivel arm 2002, which may themselves comprise distal arm flanges 3600, may comprise one or more arm apertures 3602 configured to receive, for example, one or more rivets 3604 (as shown in FIGS. 30 and 31) therethrough to couple second swivel arm 2002 to a first engaging component 12 and a second engaging component 16.

FIG. 40 shows an exemplary embodiment of a restraining device 10, such as shown in FIGS. 30 and 31, positioned about a stomach. As shown in FIG. 40, device 10 may be positioned about stomach 100 similar to placement of restraining device 10 about stomach 100 as shown in FIGS. 5B and 21, for example, so that the first engaging component 12 (not shown in FIG. 40) and the second engaging component 16 may engage opposite sides of stomach 100. Restraining device 10 may be secured to stomach 100 using one or more sutures 34 to couple restraining device 10 to stomach 100, or one or more sutures 34 may be positioned within suture aperture(s) 34 within strap 3100 and one or both of first engaging first engaging component 12 and second engaging component 16 to secure restraining device 100 about a stomach 100. FIGS. 41 and 42 show additional views of an exemplary restraining device 10 positioned about a stomach 100.

The various embodiments of restraining devices 10 described herein provide numerous benefits over the devices and systems of the prior art. An exemplary restraining device 10 may be inserted laparoscopically and/or endoscopically, is minimally invasive, completely reversible and available for chronic placement without the risk of complications. Furthermore, use of a restraining device 10 to treat and/or support a targeted tissue or organ produces a reduced amount of negative side effects than the procedures of the prior art for similar indications. While embodiments of restraining devices 10 are presented with respect to specific anatomy and treatment examples, the various restraining devices 10 and methods 300 may be expanded for use in treating any organ, limb or body structure that would benefit from reshaping, restoring, or added support provided through a reversible, easy to use and easy to implement technique for chronic placement.

Prior art focuses on creating a restrictive line through "clamps" to mimic the gastric sleeve. The disclosure of the present application provides various loosely-fitting restraints (to prevent migration) and to affect motility of the stomach. The contractility or motility curve of the gastric tissue is substantially attenuated by an external restraint (as discussed below), thus affecting the movement of bolus through the stomach. Hence, the food volume will remain in the pouch longer and lead to earlier distension which affects neuroactivity and mechanosensory elements of satiety. Hence, the principle of the restraining devices 10 of the present disclosure is based on flow (motility) unlike previous art that focuses on restrictive which risks migration and erosion.

As described herein, placement of exemplary restraining devices 10 through the lower curvature can be easily implemented as opposed to procedures which approach the greater curvature where the liver and diaphragm are in the proximity. Furthermore, various clips, clamps, or perforated plates known in the art which transverse the stomach (as opposed to sleeve) can lead to substantial remodeling of the fundus which would lead to weight regain after a period of time. As such, the various connectors of the disclosure of the present application operate to prevent overall stretch of stomach and hence prevent remodeling. The stretch that leads to mechanosensory satiety in the restraining devices of the present disclosure occurs locally between the restraining springs or bars while still restraining the overall pouch. No such global containment of the gastric tissue is known in the prior art. Finally, various clips, clamps, or perforated plates known in the art would exert significant local stresses on the tissue which can lead to erosion or migration as the substantially restricted stomach would attempt to distend. Conversely, the first engaging component 12 and the second engaging component 16 of the restraining devices 10 of the present disclosure distribute the stress more uniformly over the plate and only restrain a relatively small pouch rather than a more substantial portion of the stomach transversely.

While various embodiments of implantable restraining devices, systems, and methods for using the same have been described in considerable detail herein, the embodiments are merely offered by way of non-limiting examples of the disclosure described herein. It will therefore be understood that various changes and modifications may be made, and equivalents may be substituted for elements thereof, without departing from the scope of the disclosure. Indeed, this disclosure is not intended to be exhaustive or to limit the scope of the disclosure.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. Other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

The invention claimed is:

1. An implantable restraining device, comprising:
a first engaging component and a second engaging component at least substantially parallel to one another;
a first swivel arm, comprising:
a first fixed arm,
a first expandable arm, and
a first hub,
wherein the first fixed arm is pivotally connected to the first engaging component at or near a first fixed arm first end and is coupled to the first hub at or near a first fixed arm second end, and wherein the first expandable arm is pivotally connected to the second engaging component at or near a first expandable arm first end and is connected to the first hub at or near a first expandable arm second end by way of a first hub bracket;
a second swivel arm, comprising:
a second fixed arm,
a second expandable arm, and a second hub,
wherein the second fixed arm is pivotally connected to the first engaging component at or near a second fixed arm first end and is coupled to the second hub at or near a second fixed arm second end, and wherein the second expandable arm is pivotally connected to the second engaging component at or near a second expandable arm first end and is connected to the second hub at or near a second expandable arm second end by way of a second hub bracket; and a first strap positioned at a first end of the first engaging component and at a first end of the second engaging component and fixedly coupled to one of the first end of the first engaging component or the first end of the second engaging component by way of at least one suture, the first strap configured to limit movement of the first engaging component and the second engaging component when the first strap is coupled to the first engaging component and the second engaging component;

wherein the first expandable arm and the second expandable are capable of movement relative to the first hub and the second hub respectively so that a distance between the first engaging component and the second engaging component may change relative to movement of the first expandable arm and the second expandable arm.

2. The device of claim 1, wherein the first swivel arm is capable of rotation in a first direction, and wherein the second swivel arm is capable of rotation in an opposing second direction.

3. The device of claim 2, wherein the first swivel arm and the second swivel arm are capable of rotation so that the first swivel arm, the second swivel arm, the first engaging component, and the second engaging component share a common linear axis.

4. The device of claim 2, wherein the first swivel arm and the second swivel arm are capable of rotation so that the first swivel arm and the second swivel arm are substantially or fully perpendicular to the first engaging component and the second engaging component.

5. The device of claim 1, wherein the first fixed arm is relatively shorter than the second fixed arm, and wherein the first expandable arm is relatively shorter than the second expandable arm.

6. The device of claim 1, further comprising:
a first arm flange at or near the first expandable arm second end, the first arm flange configured to limit expansion of the first expandable arm relative to the first fixed arm; and
a second arm flange at or near the second expandable arm second end, the second arm flange configured to limit expansion of the second expandable arm relative to the second fixed arm.

7. The device of claim 1, wherein the device is sized and shaped to fit within a laparoscopic bodily port.

8. The device of claim 1, wherein the first strap has at least one suture aperture defined therethrough, and wherein at least one of the first engaging component and the second engaging component has at least one plate aperture defined therethrough, the at least one suture aperture and the at least one plate aperture configured to permit a suture to be placed therethrough to couple the first strap to either the first engaging component or the second engaging component.

9. The device of claim 1, further comprising:
a first pad coupled to one or both of the first fixed arm and the first expandable arm; and
a second pad coupled to one or both of the second fixed arm and the second expandable arm;
wherein the first pad and the second pad are configured to engage at least a portion of a mammalian bodily organ positioned therebetween.

10. The device of claim 1, wherein the first engaging component and the second engaging component are configured to engage a targeted tissue therebetween when the first swivel arm and the second swivel arm are in a configuration relatively perpendicular to the first engaging component and the second engaging component.

11. The device of claim 1, wherein the first engaging component, the second engaging component, the first swivel arm, and the second swivel arm each comprise a material suitable to resist corrosion selected from the group consisting of polyurethane, polyethylene, polytetrafluoroethylene, polyaryletherketone, carbothane, tecothane, nitinol, silastic, titanium, and stainless steel.

12. The device of claim 1, wherein each of the first engaging component and the second engaging component define one or more facets along at least part of a length of said engaging components, said facets providing a generally arcuate profile of said engaging components.

13. The device of claim 1, wherein each of the first engaging component and the second engaging component comprise a configuration chosen from a straight bar configuration, a curved configuration, or a circular configuration.

14. The device of claim 1, wherein the first engaging component and the second engaging component are flexible or semi-flexible.

15. The device of claim 1, wherein the device does not apply any meaningful pressure against a stomach when positioned upon portions of the stomach.

16. An implantable restraining device, comprising:
a first engaging component and a second engaging component at least substantially parallel to one another;
a first swivel arm, comprising:
a first fixed arm,
a first expandable arm, and
a first hub,
wherein the first fixed arm is pivotally connected to the first engaging component at or near a first fixed arm first end and is coupled to the first hub at or near a first fixed arm second end, and wherein the first expandable arm is pivotally connected to the second engaging component at or near a first expandable arm first end and is connected to the first hub at or near a first expandable arm second end by way of a first hub bracket;
a second swivel arm, comprising:
a second fixed arm,
a second expandable arm, and
a second hub,
wherein the second fixed arm is pivotally connected to the first engaging component at or near a second fixed arm first end and is coupled to the second hub at or near a second fixed arm second end, and wherein the second expandable arm is pivotally connected to the second engaging component at or near a second expandable arm first end and is connected to the second hub at or near a second expandable arm second end by way of a second hub bracket; and
a first strap positioned at one or both of a first end of the first engaging component and at a first end of the second engaging component and fixedly coupled to one of the first end of the first engaging component or the first end of the second engaging component by way of at least one suture, the first strap configured to limit movement of the first engaging component and the second engaging component when the first strap is coupled to the first engaging component and the second engaging component;

wherein the first expandable arm and the second expandable are capable of movement relative to the first hub and the second hub respectively so that a distance between the first engaging component and the second engaging component may change relative to movement of the first expandable arm and the second expandable arm; and wherein the first swivel arm is capable of rotation in a first direction so that the first swivel arm, the second swivel arm, the first engaging component, and the second engaging component share a common linear axis, and wherein the second swivel arm is capable of rotation in an opposing second direction so that the first swivel arm and the second swivel arm are substantially or fully perpendicular to the first engaging component and the second engaging component.

17. The device of claim 16, wherein the first swivel arm is capable of rotation in a first direction, and wherein the second swivel arm is capable of rotation in an opposing second direction.

18. The device of claim 16, further comprising:
a first pad coupled to one or both of the first fixed arm and the first expandable arm; and
a second pad coupled to one or both of the second fixed arm and the second expandable arm;
wherein the first pad and the second pad are configured to engage at least a portion of a mammalian bodily organ positioned therebetween.

19. A method for restoring a targeted tissue, the method comprising the steps of:
inserting an implantable restraining device into a body cavity of a mammalian body, the implantable restraining device comprising:
a first engaging component and a second engaging component at least substantially parallel to one another;
a first swivel arm, comprising:
a first fixed arm,
a first expandable arm, and
a first hub,
wherein the first fixed arm is pivotally connected to the first engaging component at or near a first fixed arm first end and is coupled to the first hub at or near a first fixed arm second end, and wherein the first expandable arm is pivotally connected to the second engaging component at or near a first expandable arm first end and is connected to the first hub at or near a first expandable arm second end by way of a first hub bracket;
a second swivel arm, comprising:
a second fixed arm,
a second expandable arm, and
a second hub,
wherein the second fixed arm is pivotally connected to the first engaging component at or near a second fixed arm first end and is coupled to the second hub at or near a second fixed arm second end, and wherein the second expandable arm is pivotally connected to the second engaging component at or near a second expandable arm first end and is connected to the second hub at or near a second expandable arm second end by way of a second hub bracket; and
a first strap positioned at a first end of the first engaging component and at a first end of the second engaging component and fixedly coupled to one of the first end of the first engaging component or the first end of the second engaging component by way of at least one suture, the first strap configured to limit movement of the first engaging component and the second engaging component when the first strap is coupled to the first engaging component and the second engaging component;
wherein the first expandable arm and the second expandable are capable of movement relative to the first hub and the second hub respectively so that a distance between the first engaging component and the second engaging component may change relative to movement of the first expandable arm and the second expandable arm;
advancing the implantable restraining device to a location within the mammalian body adjacent to a targeted tissue;
swiveling the first swivel arm and the second swivel arm so that the first swivel arm and the second swivel arm are substantially perpendicular to the first engaging component and the second engaging component; and
positioning the first engaging component and the second engaging component over the targeted tissue such that at least a portion of the targeted tissue is positioned therebetween, wherein when the targeted tissue expands in a direction between the first engaging component and the second engaging component, the targeted tissue exerts a force upon the first engaging component and the second engaging component so that the first expandable arm moves relative to the first hub and so that the second expandable arm moves relative to the second hub.

20. The method of claim 19, wherein the targeted tissue is a stomach, and wherein expansion of the stomach, with said device positioned thereon, functionally divides the stomach into a first stomach portion and a second stomach portion.

* * * * *